US010154785B2

(12) United States Patent
Sachse et al.

(10) Patent No.: US 10,154,785 B2
(45) Date of Patent: Dec. 18, 2018

(54) DEVICES AND SYSTEMS FOR FLUORESCENCE IMAGING OF TISSUE

(71) Applicant: UNIVERSITY OF UTAH RESEARCH FOUNDATION, Salt Lake City, UT (US)

(72) Inventors: Frank B. Sachse, Salt Lake City, UT (US); Robert Hitchcock, Sandy, UT (US); Chao Huang, Ogden, UT (US); Aditya K. Kaza, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 83 days.

(21) Appl. No.: 14/373,014

(22) PCT Filed: Jan. 18, 2013

(86) PCT No.: PCT/US2013/022247
§ 371 (c)(1),
(2) Date: Jul. 17, 2014

(87) PCT Pub. No.: WO2013/109957
PCT Pub. Date: Jul. 25, 2013

(65) Prior Publication Data
US 2015/0119708 A1    Apr. 30, 2015

Related U.S. Application Data

(60) Provisional application No. 61/587,963, filed on Jan. 18, 2012, provisional application No. 61/587,936, filed on Jan. 18, 2012.

(51) Int. Cl.
*A61B 5/00* (2006.01)
*G01N 21/64* (2006.01)
(Continued)

(52) U.S. Cl.
CPC .......... *A61B 5/0071* (2013.01); *A61B 5/0044* (2013.01); *A61B 5/0068* (2013.01);
(Continued)

(58) Field of Classification Search
CPC ... A61B 5/0062; A61B 5/0064; A61B 5/0068; A61B 5/0071; A61B 2562/0238;
(Continued)

(56) References Cited

U.S. PATENT DOCUMENTS

| 5,252,494 A | * | 10/1993 | Walt | ............. | G01N 21/7703 |
| | | | | | 385/123 |
| 5,312,337 A | * | 5/1994 | Flaherty | ............ | A61M 39/0208 |
| | | | | | 285/278 |

(Continued)

FOREIGN PATENT DOCUMENTS

EP    13738529.0    1/2013

OTHER PUBLICATIONS

Extended European Search Report issued by the European Patent Office dated Aug. 27, 2015 for EP 13738529.0, filed on Jan. 18, 2013 and published as EP 2804523 on Nov. 26, 2014 (Applicant—University of Utah Research Foundation // Inventor—Sache, et al.) (7 pages).

(Continued)

*Primary Examiner* — Patricia Park
*Assistant Examiner* — Nate S Sunwoo
(74) *Attorney, Agent, or Firm* — Ballard Spahr LLP

(57) ABSTRACT

A system and method for fluorescence imaging of tissue in vivo and in situ, e.g., for minimally invasive diagnosis of patients. A fluorescent imaging system is provided that has a dye carrier coupled to the distal end of a probe containing a fiber optics bundle, which allows for the introduction of at least one fluorescent dye therein the dye carrier into a portion of the tissue of interest of a subject or patient when (Continued)

the dye carrier is selectively brought into contact with the portion of the tissue of interest. The resulting fluorescence images permit the acquisition of diagnostic information on the progression of diseases at cellular/tissue level in patients.

25 Claims, 60 Drawing Sheets

(51) Int. Cl.
*A61K 49/00* (2006.01)
*A61B 5/02* (2006.01)
*A61M 5/00* (2006.01)

(52) U.S. Cl.
CPC ......... *A61B 5/0084* (2013.01); *A61B 5/02028* (2013.01); *A61B 5/4887* (2013.01); *A61K 49/0054* (2013.01); *A61K 49/0073* (2013.01); *A61M 5/007* (2013.01); *G01N 21/6456* (2013.01); *A61B 2562/0233* (2013.01); *A61B 2576/023* (2013.01); *G01N 2021/6423* (2013.01); *G01N 2021/6439* (2013.01); *G01N 2021/6463* (2013.01); *G01N 2021/6484* (2013.01)

(58) Field of Classification Search
CPC .......... A61B 2562/16; A61B 2562/223; A61K 49/0017; A61K 49/0019; A61K 49/0021; A61K 49/005; A61K 49/0073
See application file for complete search history.

(56) References Cited

U.S. PATENT DOCUMENTS

| | | |
|---|---|---|
| 5,678,550 A | 10/1997 | Bassen et al. |
| 2006/0015070 A1* | 1/2006 | Howell ................. A61B 90/39 604/164.13 |
| 2006/0245087 A1* | 11/2006 | Tearney ............... G02B 21/006 359/819 |
| 2008/0019657 A1* | 1/2008 | Maitland ............. G02B 6/0008 385/140 |
| 2008/0051632 A1* | 2/2008 | Ito ........................ A61B 1/0607 600/114 |
| 2008/0193995 A1* | 8/2008 | Tajima .................. G01N 35/10 435/174 |
| 2011/0301438 A1* | 12/2011 | Sachse ................ A61B 5/0068 600/301 |

OTHER PUBLICATIONS

Extended European Search Report and Written Opinion dated Nov. 28, 2016 by the European Patent Office for EP Application No. 16184962.5, which was filed on Jan. 18, 2013 and published as 3114989 on Jan. 11, 2017 (Applicant—University of Utah Research Foundation) (6 Pages).

Communication pursuant to Article 94(3) EPC dated Dec. 16, 2016 by the European Patent Office for EP Application No. 09805257.4, which was filed on Aug. 4, 2009 and published as 2324362 on May 25, 2011 (Applicant—University of Utah Research Foundation) (2 Pages).

* cited by examiner

100

Tissue

10 Fluorescence Imaging Device

30 Optical Fibers

60 Lens

40 Processor

Fluorescence Image

| Material (n=3) | Initial Weight (mg) | Amount Absorbed (mg) | Max Line# Recorded | Initial Intensity | Decay Rate (lines) |
|---|---|---|---|---|---|
| PU | 2.6 ± 0.1 | 65.6 ± 6.1 | 1 | N/A | N/A |
| High density PU | 14.8 ± 2.7 | 71.8 ± 3.9 | 1 | N/A | N/A |
| PES | 2.6 ± 0.4 | 63.5 ± 4.3 | 1 | N/A | N/A |
| PU/1% Agar | 61.9 ± 2.0 | 37.1 ± 3.5 | 14 | 781.9 ± 245.7 | 1.92 |
| PU/3% Agar | 63.5 ± 3.4 | 30.8 ± 6.1 | 13 | 1057.9 ± 26.3 | 2.65 |
| PU/5% Agar | 70.2 ± 4.5 | 31.3 ± 3.8 | 9 | 890.4 ± 217.9 | 4.58 |

| | Length (μm) | Width (μm) | Height (μm) | Volume (μm³) | Surface Area (μm²) | Myocyte Volume Fraction |
|---|---|---|---|---|---|---|
| Non-Stimulated (NS) Samples n=7, segmented cells n=64 | 58.8 ± 21.8 | 13.0 ± 2.7 | 10.1 ± 2.5 | 2647 ± 790 | 1400 ± 381 | 0.19 ± 0.06 |
| Stimulated (S) Samples n=7, segmented cells n=58 | 81.5 ± 19.7 | 11.3 ± 2.0 | 8.6 ± 1.6 | 2968 ± 1296 | 1775 ± 585 | 0.34 ± 0.14 |
| Postnatal Day 12 (P12) Rats n=5, segmented cells n=41 | 72.0 ± 10.9 | 11.5 ± 1.6 | 9.1 ± 1.3 | 3167 ± 783 | 1732 ± 344 | 0.90 ± 0.06 |
| Adult Rats n=7, segmented cells n=51 | 120.1 ± 31.3 | 29.4 ± 5.9 | 19.6 ± 3.3 | 26916 ± 11550 | 7431 ± 2555 | 0.91 ± 0.04 |

FIG. 33A

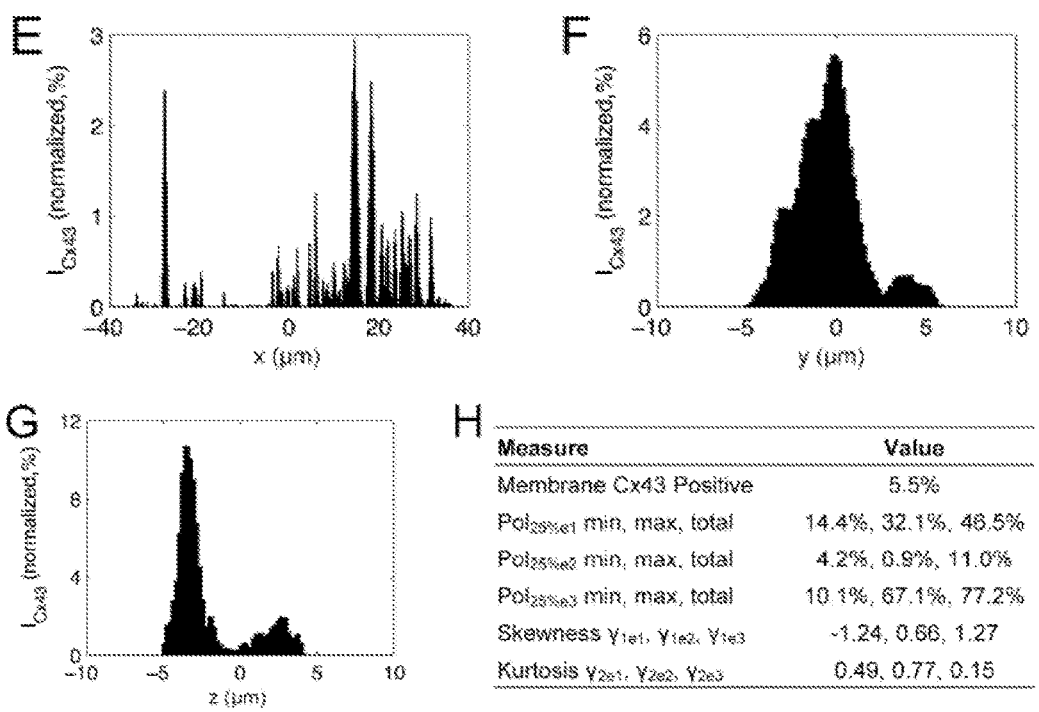
FIG. 34, continued

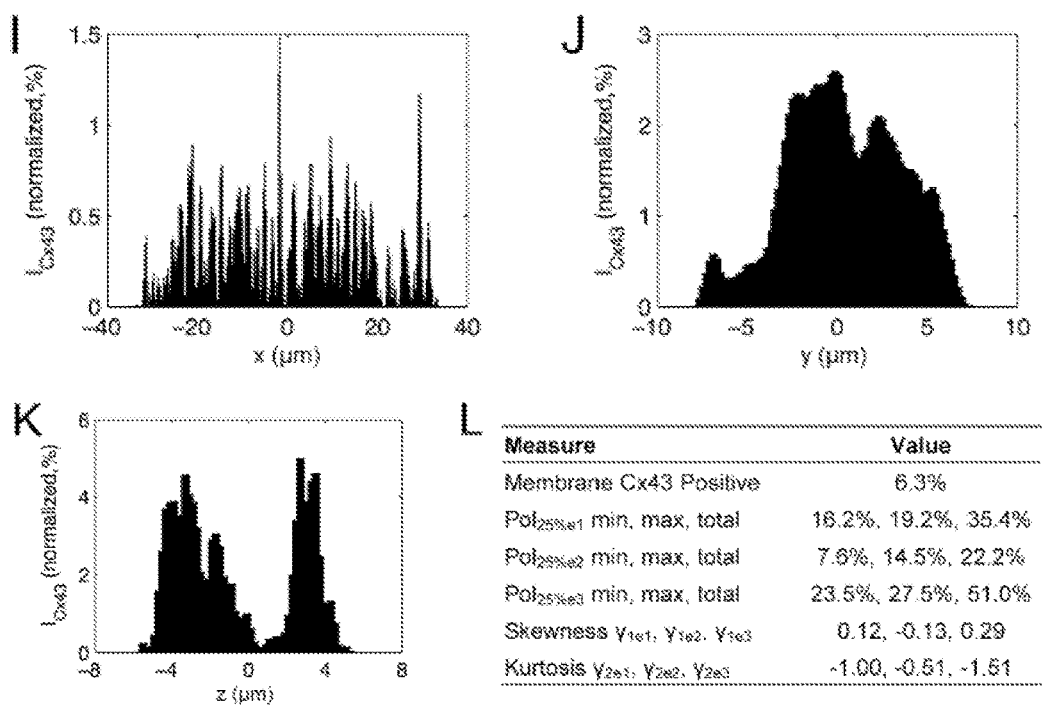
FIG. 34, continued

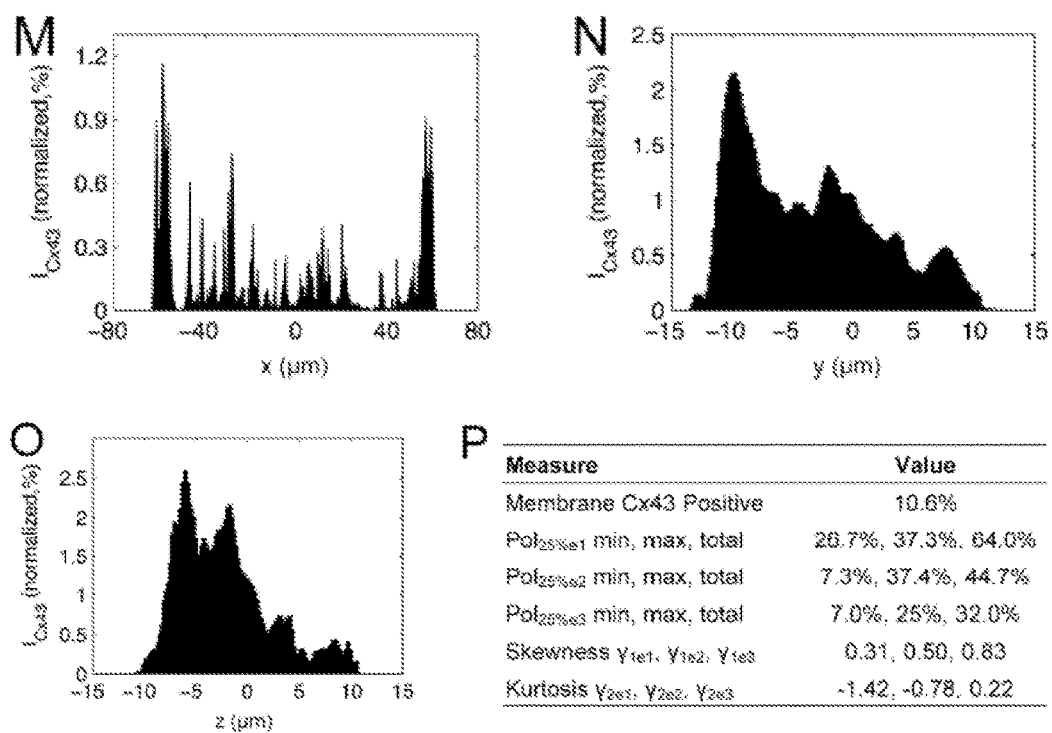
FIG. 34, continued

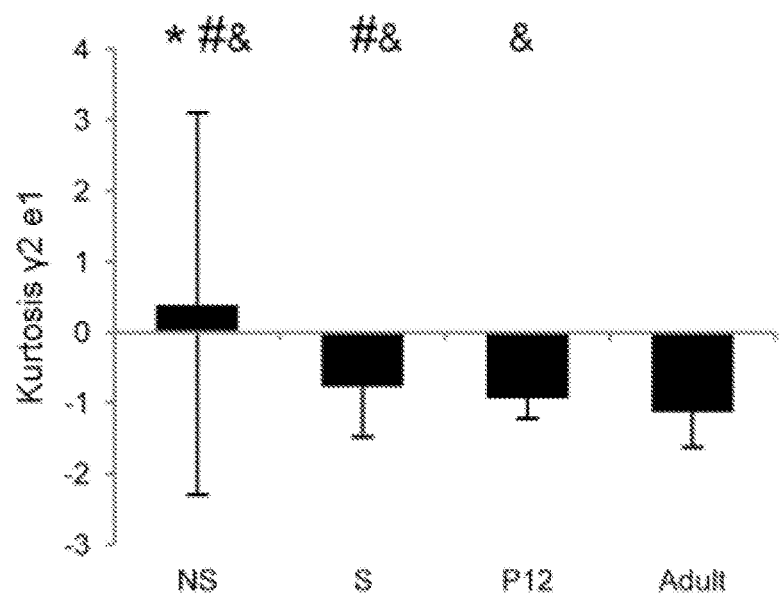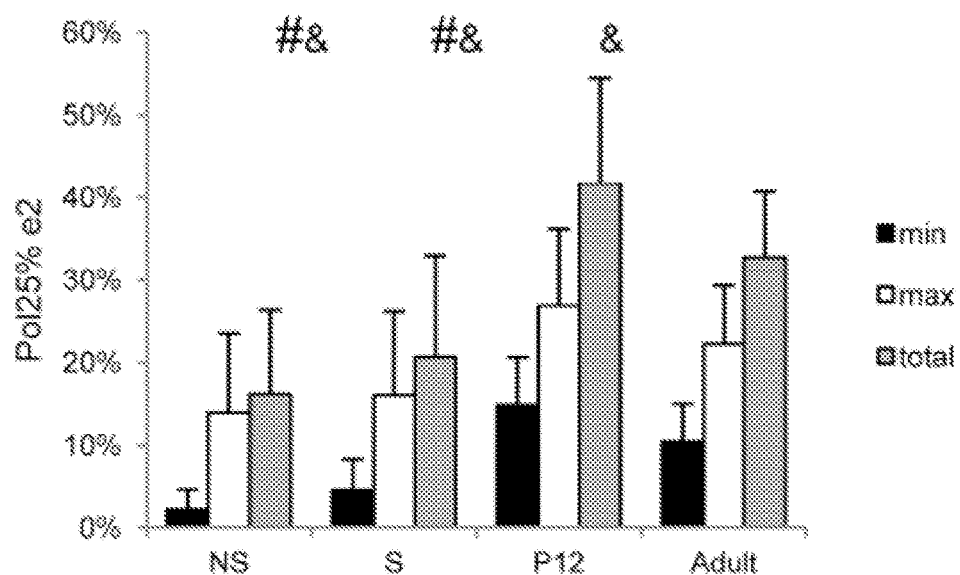
FIG. 36, continued

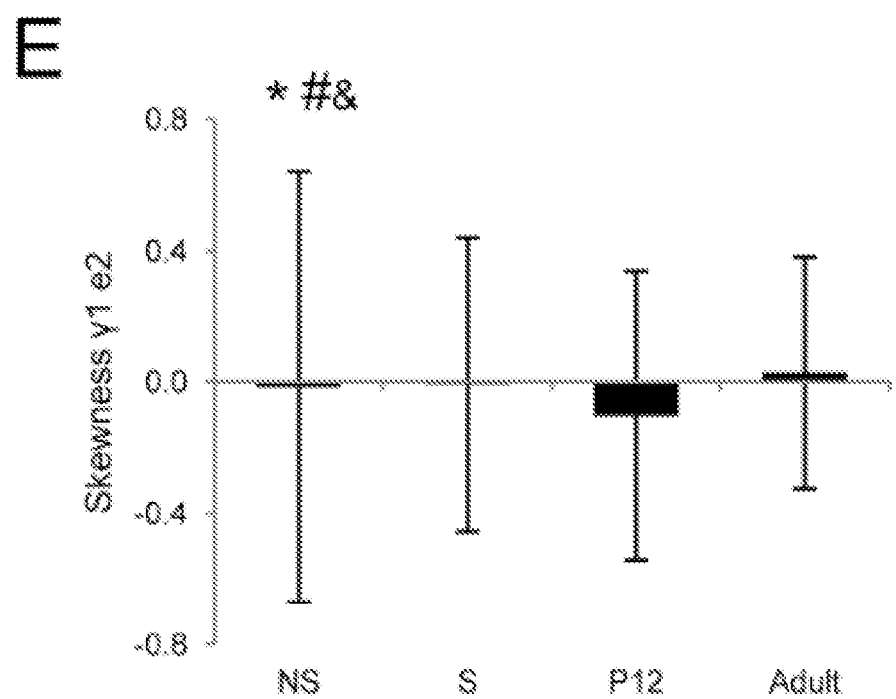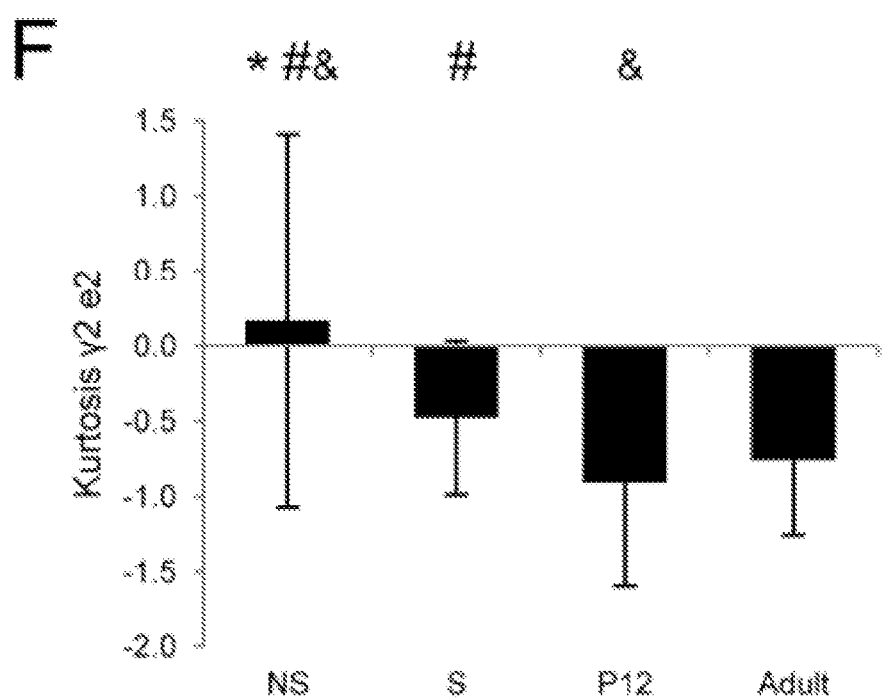
FIG. 36, continued

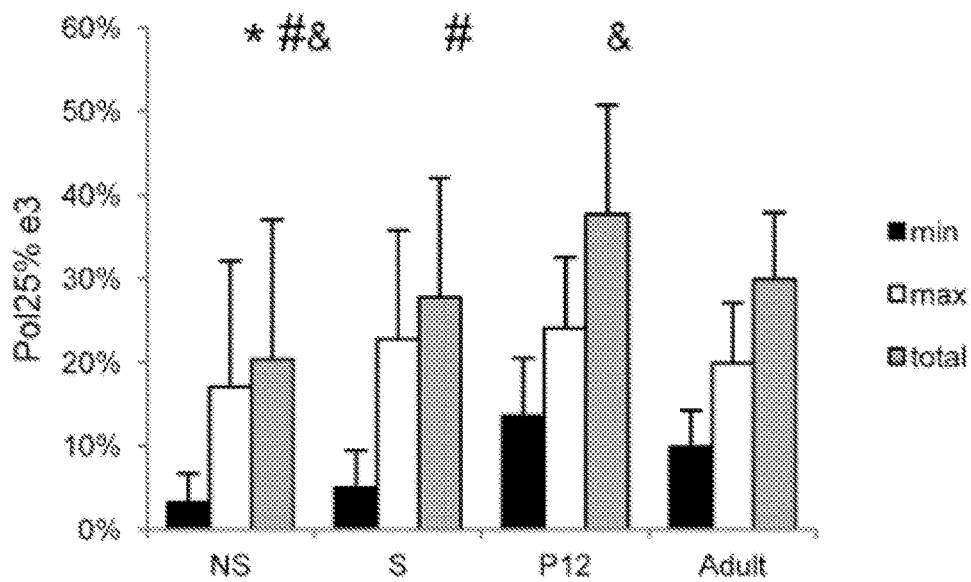
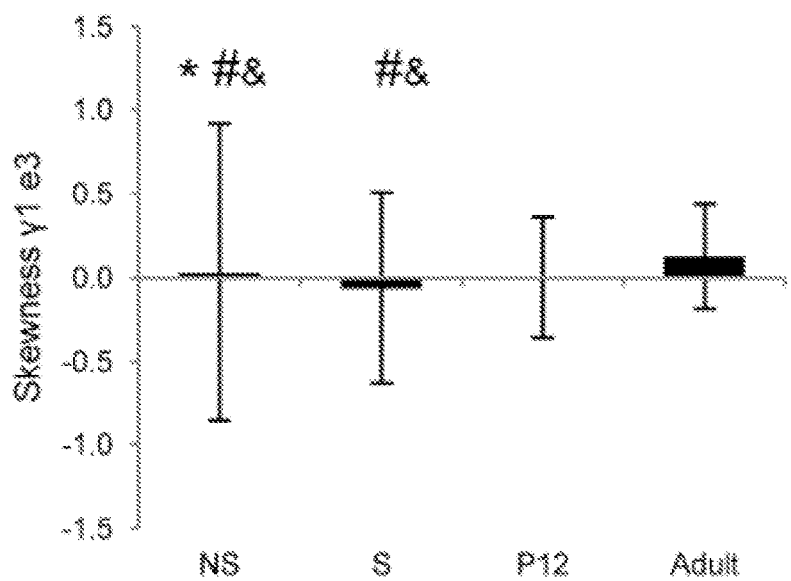
FIG. 36, continued

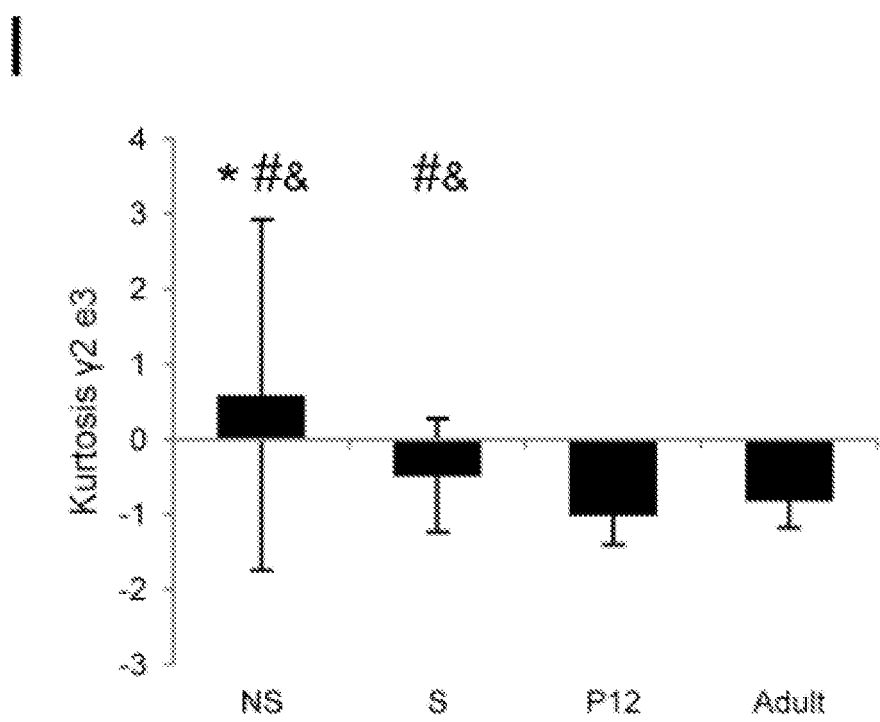
FIG. 36, continued

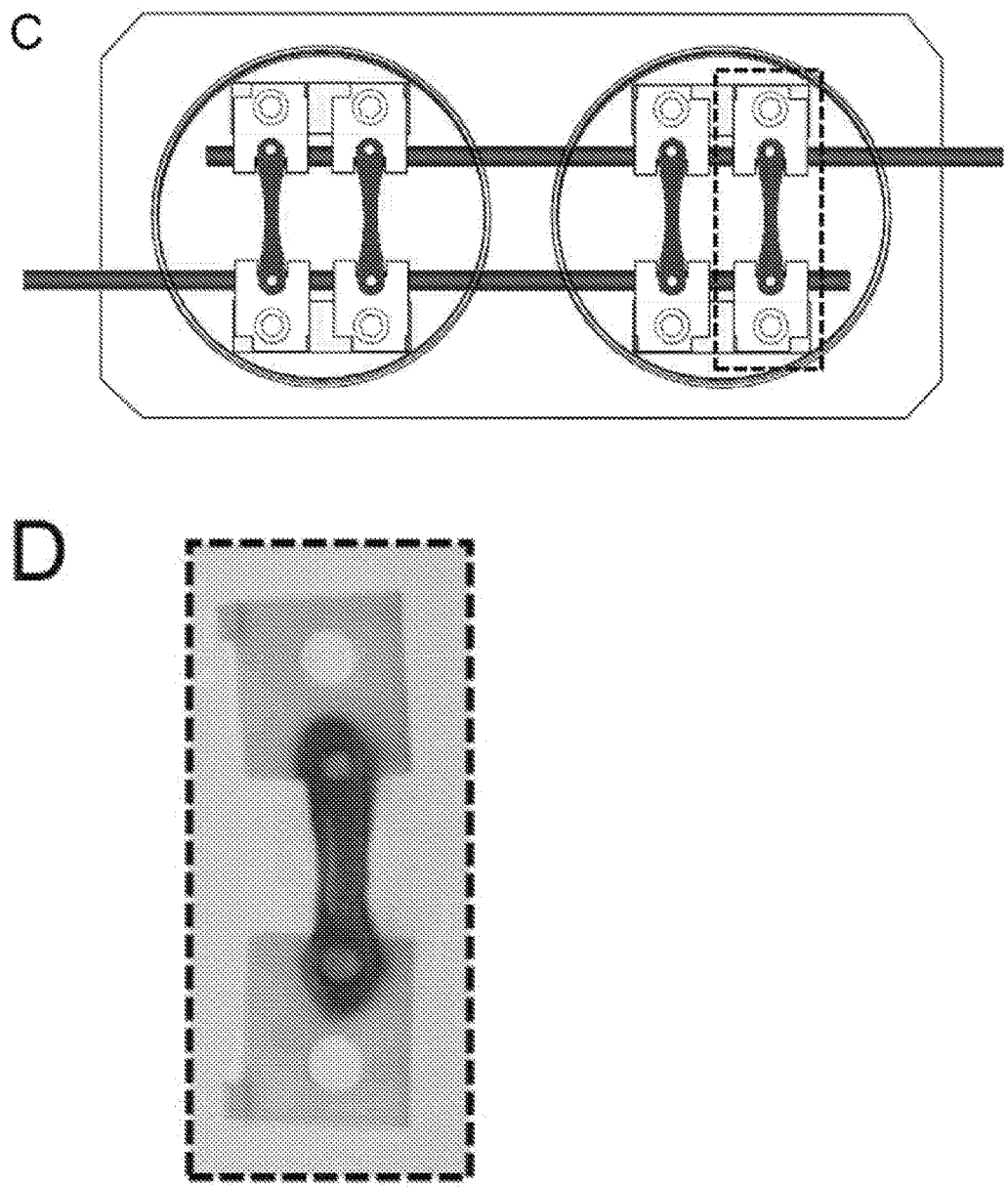
FIG. 37, continued

DEVICES AND SYSTEMS FOR FLUORESCENCE IMAGING OF TISSUE

CROSS-REFERENCE TO RELATED APPLICATIONS

This application is a National Phase Application of International Application No. PCT/US2013/022247, filed Jan. 18, 2013, which claims the benefit of the filing date of U.S. Provisional Patent Application No. 61/587,936, filed on Jan. 18, 2012, and U.S. Provisional Patent Application No. 61/587,963, filed on Jan. 18, 2012, each of which is incorporated herein by reference in its entirety.

FIELD

This invention generally relates to fluorescence imaging of tissues and, more particularly, to devices and methods for applying fluorescent dye to a tissue of a subject for purposes of developing a fluorescence image of the tissue for use in tissue discrimination and disease diagnosis.

BACKGROUND

Fluorescence Imaging

Currently, magnetic resonance (MR), ultrasonic (US) and computer tomographic (CT) imaging techniques are major tools for clinical diagnosis of diseases and evaluation of therapeutic interventions. Microscopic imaging techniques, for instance, those based on fluorescent dyes constitute an effective and complementary approach for acquiring microstructural information that can be used to discriminate among tissue types, study the progression of diseases in tissue and cells, and evaluate potential treatment options for such diseases.

Fluorescence microscopy is an indispensable tool in cell biology because the fluorescence labelling of proteins, molecules and spaces enables the study of structures and functions in biologic specimens. Typically, fluorescence microscopy has not been used to examine tissue in situ because of the need for close association between microscope instrumentation and the imaged tissue, toxic or expensive fluorescent dyes for image contrast, and relatively long image acquisition times. Despite these challenges, fluorescence microscopy techniques have been shown to provide valuable diagnostic information for various disease states. Studies with biopsy specimens suggest that fluorescence imaging can provide useful diagnostic information about the presence of precancerous lesions; confocal images of normal and dysplastic cervical biopsy specimens obtained with a confocal reflectance microscope showed a strong correlation between nuclear morphologic features extracted from fluorescence images and histopathologic diagnosis.

Fluorescent microscopy techniques include confocal microscopy that allows creation of high resolution images and differ from conventional optical microscopy in that they use a condenser lens to focus illuminating light of specific wavelengths from a light source, e.g., a laser, into a very small, diffraction limited spot within a specimen, and an objective lens to focus the light emitted from that spot onto a small pinhole in an opaque screen. A detector, which is capable of quantifying the intensity of the light that passes through the pinhole at any instant, is located behind the screen. Because only light from within the illuminated spot is properly focused to pass through the pinhole and reach the detector, any stray light from structures above, below, or to the side of the illuminated spot are filtered out. The image resolution is therefore greatly enhanced as compared to other conventional tissue imaging approaches.

In a scanning confocal microscopic imaging system, a coherent image is built up by scanning point by point over the desired field of view and recording the intensity of the light emitted from each spot, as small spots are illuminated at any one time. Scanning can be accomplished in several ways, including for example and without limitation, via laser scanning. Confocal microscopic imaging system are commercially available through entities such as Carl Zeiss, Nikon, Leica, and Olympus, including, for example and without limitation, a Zeiss LSM 5 Duo, a Leica FCM1000, and the like. An exemplary confocal microscopic imaging system is described in U.S. Pat. No. 6,522,444 entitled "Integrated Angled-Dual-Axis Confocal Scanning Endoscopes," which is assigned to Optical Biopsy Technologies, Inc.

The ability to obtain fluorescence images of normal and diseased tissue in situ is limited by the ability to bring the tissue of interest in close proximity to the objective lens of the microscope. Fluorescence microscopic imaging systems incorporating either a solitary optical fiber or a fiber optic imaging bundle are needed to facilitate in situ imaging of less accessible organ sites. Similarly, miniaturized fluorescent microscopic systems allow for imaging of organs and tissues in situ. However, a major obstacle for application of fluorescence microscopic imaging techniques is related to the introduction of fluorescent dyes into biological tissue. Commonly, introduction of dye is performed by infusion or systemic needle injection. Disadvantages of these methods include, for example, the high dosages of the dye(s) required for imaging, wash-out (release of the dye(s) by the tissue), and inhomogeneous distribution of the fluorescent dye.

Imaging of Cardiac Tissue

Quantity, density, and morphology of cardiac cells vary significantly during development, amongst species, for each cardiac tissue and in heart disease. Many diseases, such as hypertrophy, atrophy, infarction, and ischemia, are known to be associated with alterations in cell geometry and density. For instance, in cardiac hypertrophy, human epicardial left ventricular myocytes have been shown to increase in length, width, area, and volume by approximately 9%, 28%, 39%, and 78%, respectively, and rabbit right ventricular myocytes are known to increase in length and width by approximately 7.5% and 36%, respectively. In atrophic hearts, left ventricular myocytes decrease in volume by 50%-75%, with little change in myocyte length. Cardiac diseases are also known to alter the extracellular environment. Following myocardial infarction, fibrosis (excessive deposition of extracellular matrix mediated by fibroblasts) occurs not only in the infarcted region, but in the surrounding regions as well. Furthermore, early stages of ischemia are known to decrease the extracellular resistance, which is indicative of reduced interstitial space.

A more comprehensive understanding of these pathologic cellular and tissue alterations could allow the recently developed fiber-optics confocal systems and optical imaging techniques to provide a new set of diagnostic tools in cardiology.

In previous studies, pathologic alterations of cardiac microstructure have been characterized ex vivo with confocal microscopy. However, the application of confocal microscopy requires that fluorescent dye for labeling of proteins or structures is available in sufficient concentration in the region of interest. Dye delivery is commonly a time-consuming immunochemistry procedure, requiring excision, fixation, and sectioning of tissue as well as cell membrane disruption. In particular, in vivo dye delivery is an unresolved issue that impedes the application of fiber-optics confocal imaging in these studies.

Image data from both living and fixed tissue specimens have been used to develop models that describe physical and physiological properties of cardiac tissue. For instance, models that describe mechanical and electrophysiological properties in normal and diseased cells and tissues have been developed. Most of these models do not directly account for the detailed tissue microstructure, but describe tissue properties with lumped parameters or homogenization approaches. A small number of models have been introduced, which are based on an analytical description of microstructure or on two-dimensional microscopic images.

Cardiac tissue can be viewed as a composite material comprised of fluids and cells, including myocytes, fibroblasts, endothelial, vascular smooth muscle, and neuronal cells. Myocytes occupy most of the volume in cardiac tissue and are responsible for cardiac contraction. The (interstitial) space between cardiac cells is filled with fluid and an interconnected extracellular matrix comprised mostly of collagen and capillary vessels.

Myocytes in ventricular and atrial tissue exhibit a microstructural organization that underlies physical and physiological properties, such as electrical conductivity and electrical wave velocity, respectively. Other components of the heart have differing micro-structural arrangements, such as the strand like fibers of the Purkinje system.

There are several complications associated with heart surgery, including dysfunction of sino-atrial and atrio-ventricular conduction pathways. These complications require chronic cardiac rhythm management using implantable pacemakers. Despite the complexity and individual variations in cardiac conductive pathways, tissue discrimination during surgery is currently limited to the use of anatomic landmarks, and accurate surgical intervention is challenging and risky. One of the perioperative complications that can be induced during these procedures is complete heart block that is purportedly associated with interruption of cardiac conduction pathways.

Therefore, what is needed in the art are fluorescence imaging systems and methods that achieve in vivo imaging and microstructural characterization of tissues while avoiding high dosages of fluorescent dye(s), undesired wash-out, and inhomogeneous distribution of fluorescent dye(s) within the tissue. There is a further need in the art for systems and methods of producing detailed images of tissue microstructure in real time during the performance of surgical procedures. There is still a further need in the art for systems and methods of identifying conductive pathways within a tissue to avoid damage to such conductive pathways during a surgical procedure.

SUMMARY

The present invention relates to a fluorescence imaging device that is configured for use within a fluorescence microscopic imaging system, including conventional confocal imaging systems, miniaturized fluorescence imaging systems and those that transmit and obtain images through fiber-optics. The fluorescence imaging device is adapted for the study of tissue at locations within a body wherein one or more fluorescent dyes are selectively introduced into the tissue region under observation.

In one aspect, the fluorescence imaging device includes a probe defining a central bore and having an outer surface, a distal end, an opposed proximal end, and a longitudinal axis extending between the distal end and the proximal end of the probe. The distal end of the probe defines a distal tip configured for contact with a selected tissue of a subject. The probe includes image transmission means, such as a fiber-optic bundle, positioned within the central bore of the probe and placed in communication with a light source. The probe further includes a lens positioned within the central bore of the probe proximate the distal tip of the probe.

In another aspect, the fluorescence imaging device includes a dye carrier comprising at least one fluorescent dye. The dye carrier has a bottom surface configured to contact the tissue of the subject. The dye carrier is coupled to at least a portion of the outer surface of the probe such that the bottom surface of the dye carrier is substantially flush with the distal tip of the probe. The dye carrier is configured to selectively dispense the fluorescent dye(s) into the tissue of the subject.

In a further aspect, the invention relates to a fluorescence imaging system including means for dispensing a fluorescent dye into a selected region of a cardiac tissue. The system can also include a light source that transmits light to the selected region of the cardiac tissue. Additionally, the system can include means for receiving emitted light from the fluorescent dye within the cardiac tissue. Further, the system can include a processor in operative communication with the means for receiving emitted light from the fluorescent dye. The processor processes the received emitted light from the fluorescent dye and (1) generates a fluorescence image of the selected region of the cardiac tissue and (2) characterizes the micro-structure of the selected region of the cardiac tissue. Optionally, the processor can identify conductive tissue in the selected image region. Methods of using the disclosed system are also provided.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

FIG. 2 depicts the transmission of light to a selected tissue region, whereas FIG. 3 depicts the generation of an image of the tissue region.

FIG. 9 is an exemplary experimental setup for confocal imaging of cardiac tissue.

FIG. 10 is a schematic view of an exemplary experimental and processing method for confocal imaging.

FIG. 11 is an image taken during an exemplary experiment with a fiber-optics confocal microscopy system (LeicaFCM 1000) showing (a) M/30 confocal microprobe with hydrogel carrier loaded with dye; (b) Image of atrial tissue acquired with fiber-optics confocal microscopy system and the modified microprobe. Scale: 5 mm in (a) and 50 μm in (b).

FIG. 12 depicts exemplary raw XY images from a three-dimensional stack of atrial tissue. The images are from the (a) epicardial surface and a depth of (b) 10 μm, (c) 20 μm, and (d) 30 μm into the myocardium. Scale: 50 μm in (a) applies to (a)-(d).

FIG. 13 depicts exemplary raw XY images from a three-dimensional stack of ventricular tissue. The images are from the (a) endocardial surface and a depth of (b) 10 μm, (c) 20 μm, and (d) 30 μm into the myocardium. Also shown are (e) a zoomed view of region marked by white box in (c) and (f) a processed image from region marked by whitebox in (c). The arrows indicate cross-sections of transverse tubules. Scales: 50 μm in (a) applies to (a)-(d), 2 μm in (e) applies also to (f).

FIG. 14 depicts an exemplary segmentation of a single cardiac myocyte in (a) XY, (b) XZ and (c) YZ images of atrial tissue. Also shown in (d) is a three-dimensional model of a myocyte created by manual segmentation and thresholding. Scale: 20 μm applies to (a)-(c).

FIG. 15 is a three-dimensional model of atrial tissue shown (a) from an epicardial surface, (b) in fiber direction, and (c) from lateral side. Also shown in (d) is a model overlaid with exemplary confocal images in three orthogonal planes. The model includes 17 complete myocytes and 21 partial myocytes. Scale: 50 μm applies to (a)-(c).

FIG. 16 is a three-dimensional model of ventricular tissue shown from the endocardial surface. The model includes 11 complete myocytes and 11 partial myocytes. Scale: 50 μm.

FIG. 25 depicts a cross-sectional side view of packaging showing the attachment of a probe to a dye carrier in the left-most chamber defined by the packaging. The two right-hand chambers are shown with unused dye carriers and are therefore configured for attachment to the imaging probe.

FIG. 26 is a top-view of exemplary packaging for storing and/or discarding dye carriers. As shown, the two left-hand chambers have not been used and are ready to be loaded on the imaging probe. The right-most chamber is depicted as having a used dye carrier that has been removed and is no longer available for re-use due to the retention latch and retention lip as shown.

FIG. 27 depicts the detachment of a dye carrier from an imaging probe as described herein. As depicted, the detachment of the dye carrier is facilitated by removal features that are integral to the dye carrier and/or the packaging for the dye carrier.

DETAILED DESCRIPTION

Figure 1A:
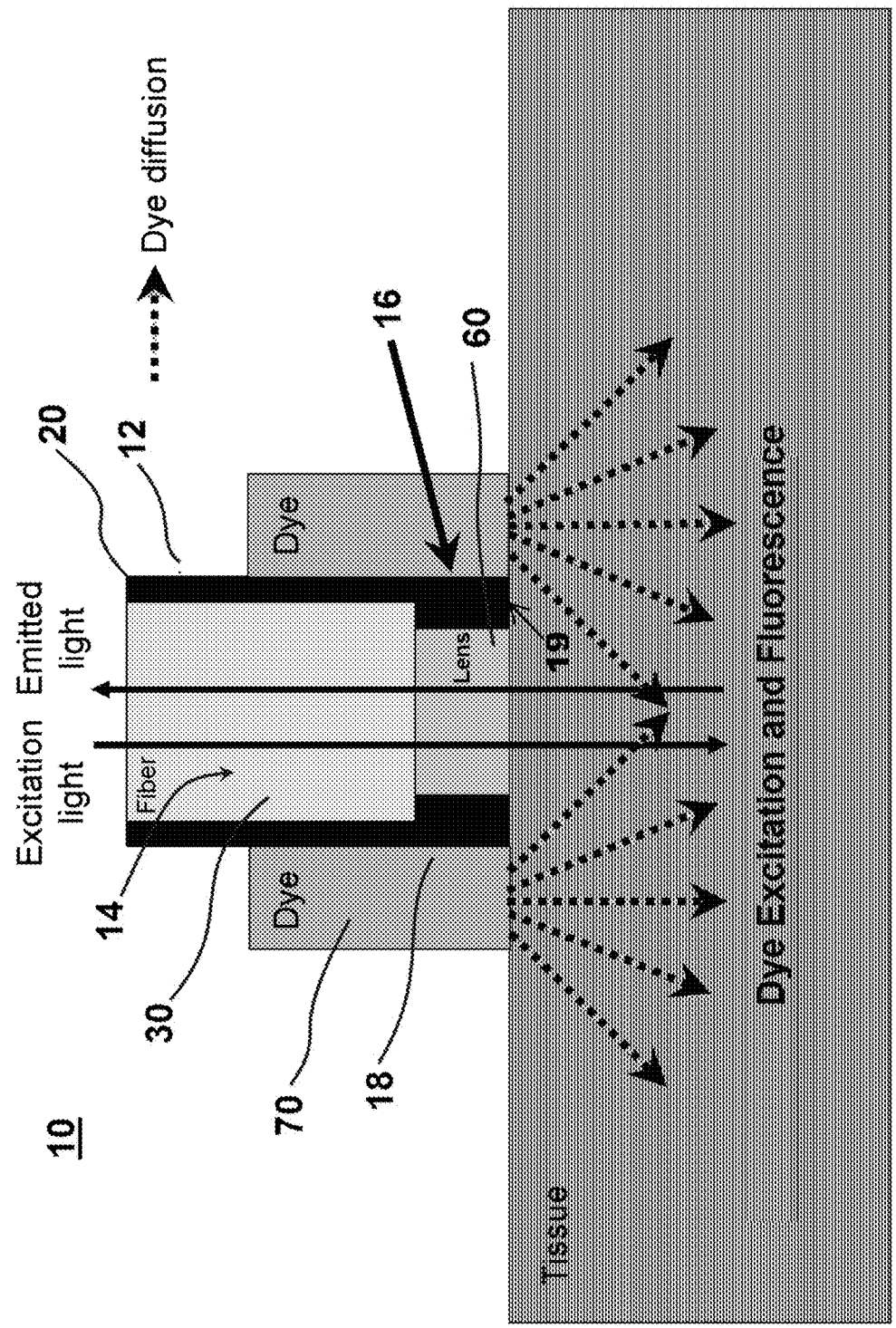
FIGS. 1A-1C show schematic views of exemplary fluorescence imaging devices having a probe and a dye carrier coupled to the outer surface of the probe such that a bottom surface of the dye carrier is substantially flush with a distal tip of the probe, as described herein. In operation, when the dye carrier is positioned in contact with a tissue of interest, dye diffuses from the dye carrier into portions of the tissue of interest. Diffusion underlies the release of dye from the carrier and dye transport in the tissue of interest. Excitation and emitted light is transmitted through the image transmission means and the dye carrier.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a dye," can include two or more such dyes unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

By a "subject" is meant an individual. The term subject can include humans and can also include small or laboratory animals as well as primates. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

As used herein and without limitation, "tissue" can refer to an aggregate of cells of a particular kind, together with their intercellular substances, that forms a solid or fluid material, whether native or produced in vitro. In one aspect, at least one portion of the selected tissue of the subject must be accessible to the device. In one exemplary non-limiting aspect, the selected tissue can be cardiac tissue. Other tissues suitable for use with this invention include, for example and without limitation, pulmonary, gastrointestinal, urogynecologic, endocrine, neural and vascular tissue.

Figure 1B:
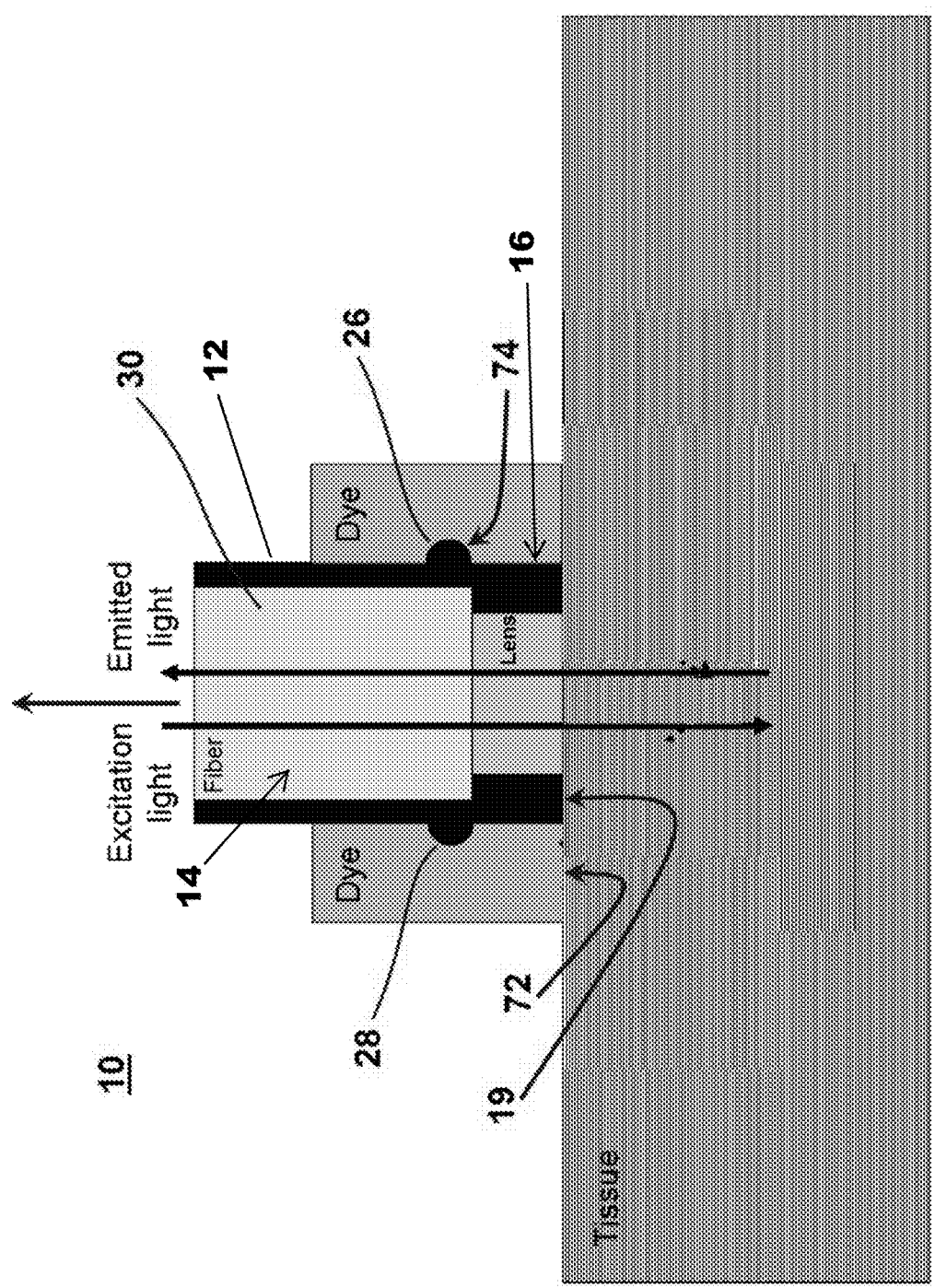
Figure 1C:
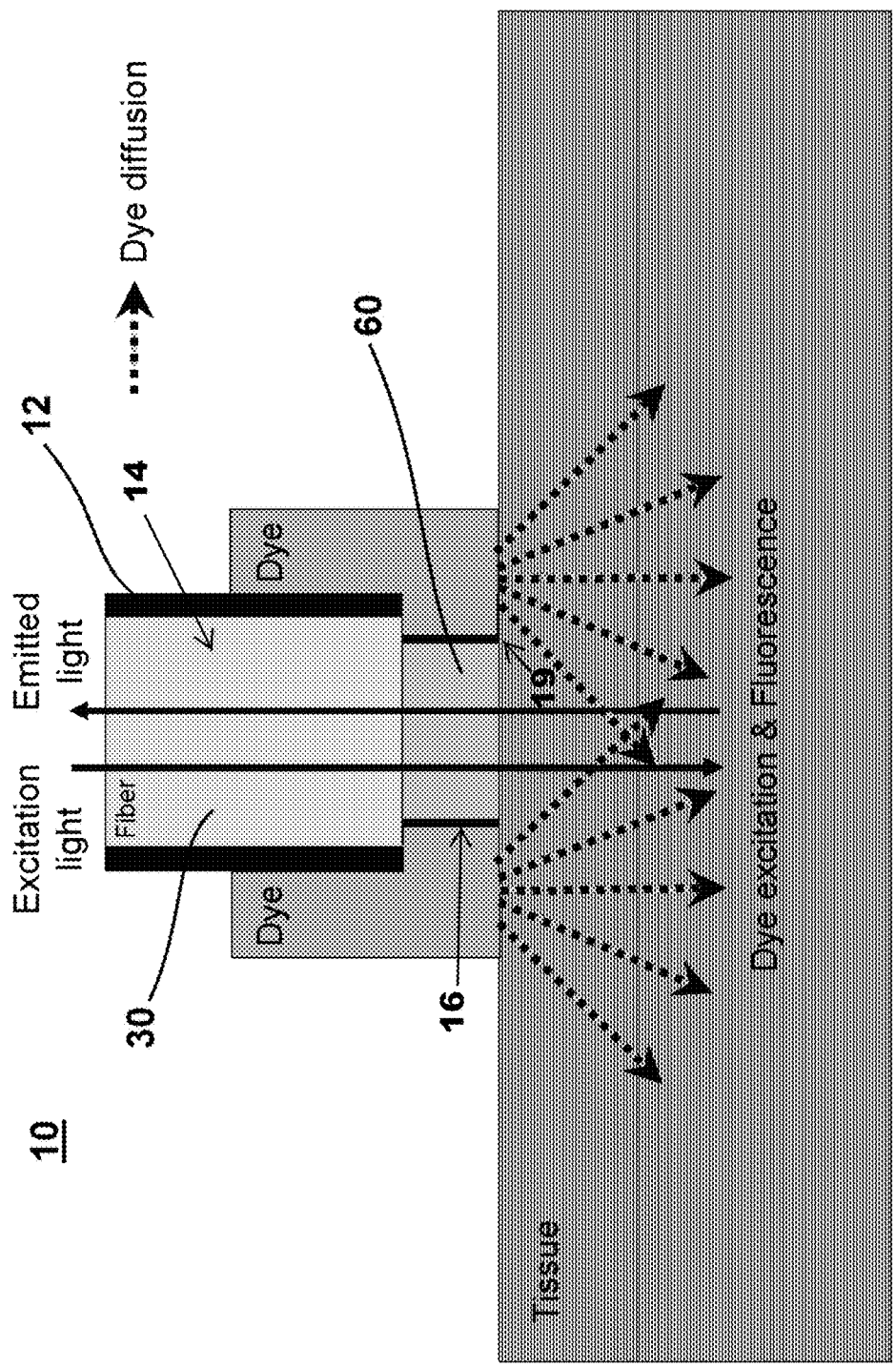

Referring to FIGS. 1A-1C, a fluorescence imaging device 10 is provided for use with a conventional confocal microscopic imaging system that is configured to produce a fluorescence image of a portion of a selected tissue of a subject. In one aspect, and as described in more detail below, the fluorescence microscopic imaging system 100 can comprise a processor 40. In a further aspect, the fluorescence imaging device 10 can comprise a probe 12 and a dye carrier 70.

Figure 2:
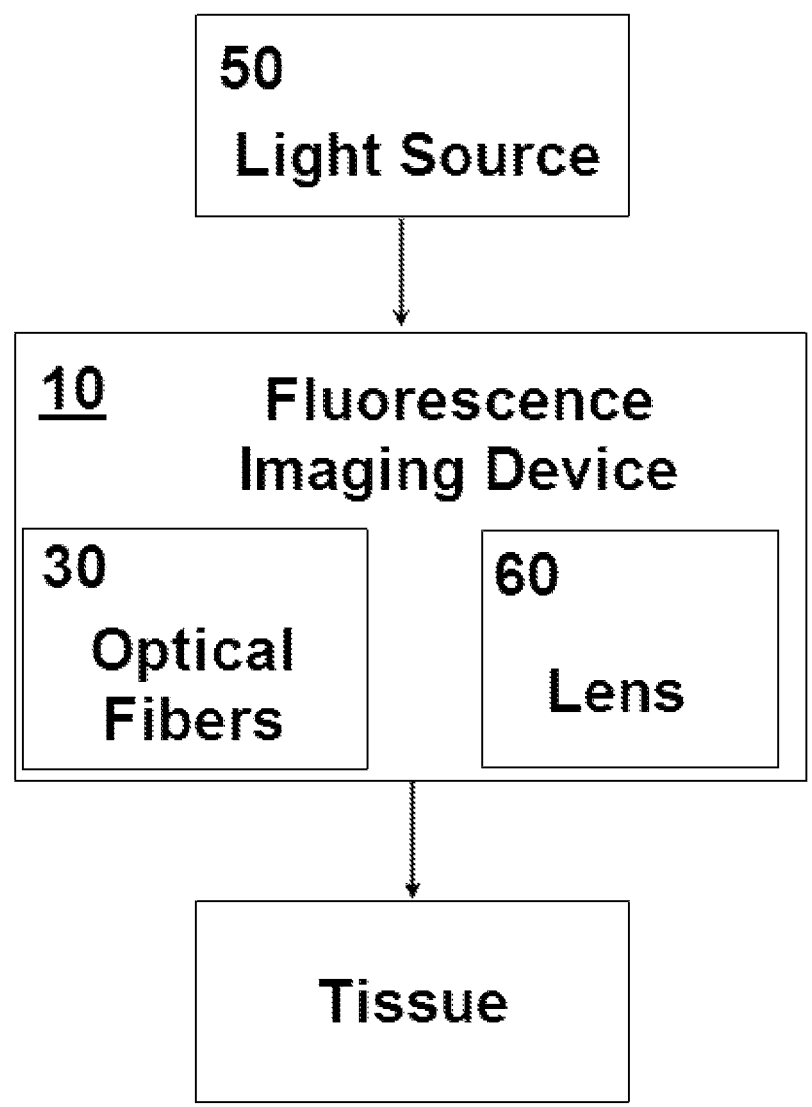
FIGS. 2-3 show schematic diagrams of the interaction between the various components of an exemplary fluorescence imaging system as described herein.

In one aspect, the probe 12 of the fluorescence imaging device 10 can have an outer surface 16, a distal end 18, an opposed proximal end 20, and a longitudinal axis 32 extending between the distal end and the proximal end of the probe. The distal end 18 of the probe 12 can define a distal tip 19 that is configured to contact the selected tissue of the subject. Optionally, the probe 12 can define a central bore 14. In another aspect, the probe 12 can comprise image transmission means. In this aspect, the image transmission means can be positioned therein the central bore 14 of the probe 12. Alternatively, it is contemplated that the image transmission means can be secured thereto a portion of the outer surface 16 of the probe 12. In a further aspect, and with reference to FIG. 2, the image transmission means can be configured for operative communication with a light source 50, such as, for example and without limitation, a laser, a single light emitting diode (LED), an array of LEDs, and the like. In one aspect, the probe 12 can have a longitudinal length, and the outer surface 16 of the probe can define an outer diameter of the probe. In an additional aspect, the probe 12 can comprise an objective lens 60 positioned therein the central bore 14 of the probe proximate the distal tip 19 of the probe.

In an exemplary aspect, the image transmission means can comprise a fiber-optic bundle 30 positioned therein the central bore 14 of the probe 12. In this aspect, it is contemplated that the objective lens 60 can be positioned therein the central bore 14 of the probe 12 such that the objective lens and the fiber-optic bundle have a common longitudinal axis substantially parallel to the longitudinal axis 32 of the probe. In another exemplary aspect, it is contemplated that the common longitudinal axis of the objective lens 60 and the fiber-optic bundle 30 can be substantially aligned with the longitudinal axis 32 of the probe 12.

Although exemplarily described herein as a fiber-optic bundle 30, it is contemplated that the image transmission means of the probe 12 can comprise any conventional mechanism for transmitting an image from the objective lens 60 to an image processing system, including any known image-transmitting liquids or solids. In exemplary aspects, the image transmission means can comprise at least one of, for example and without limitation, a clear rod, a single wire, a plurality of wires, a microscopic camera, and the like.

In another aspect, the dye carrier 70 of the fluorescence imaging device 10 can comprise at least one fluorescent dye and have a bottom surface 72 configured to contact the selected tissue of the subject. In this aspect, as shown in FIGS. 1A-1C, the dye carrier 70 can be coupled thereto at least a portion of the outer surface 16 of the probe 12 such that the bottom surface 72 of the dye carrier is substantially flush with the distal tip 19 of the probe. However, in exemplary aspects, it is contemplated that the bottom surface 72 of the dye carrier 70 can extend slightly beyond the distal tip 19 of the probe 12 such that the dye carrier can contact the selected tissue without the distal tip of the probe contacting the selected tissue. It is further contemplated that the dye carrier 70 can be coupled thereto the outer surface 16 of the probe 12 using any conventional means, including, for example and without limitation, a biocompatible adhesive. In a further aspect, the dye carrier 70 can be configured to selectively dispense the at least one fluorescent dye into the selected tissue of the subject. It is contemplated that, due to the described positioning of the dye carrier 70 around the outer surface 16 of the probe 12, there is direct transmission of light between the lens 60 and fiber optic bundle 30 of the probe and the selected tissue—the dye carrier is spaced from the central bore 14 such that the dye carrier does not interfere with the light transmission and, consequently, decrease the quality or accuracy of any confocal images of the selected tissue that are produced. It is further contemplated that the shape of the bottom surface 72 of the dye carrier 70 can be formed in such a way to prevent the interference with the light transmission. It is further contemplated that, due to the described positioning of the dye carrier 70 around the outer surface 16 of the probe 12, the at least one fluorescent dye can be dispensed in an area of the selected tissue significantly larger than the portion of the selected tissue to which light can be applied at a given time. In exemplary aspects, the at least one fluorescent dye can comprise at least one of Alexa, Texas Red, FITC, Oregon Green, Rhodamine Green, Lucifer yellow, Fluo 3, Fluo 4, di-8-Anepps, and the like.

In various aspects, the dye carrier 70 can have a longitudinal axis. In one aspect, as shown in FIGS. 1A-1C, it is contemplated that the dye carrier 70 can extend circumferentially around at least a portion of the outer surface 16 of the probe 12 such that the longitudinal axis of the dye carrier is substantially aligned with the longitudinal axis 32 of the probe. Alternatively, it is contemplated that the dye carrier 70 can be coupled to the outer surface 16 such that the probe 12 and the dye carrier are positioned in a side-by-side configuration and the longitudinal axis of the dye carrier is substantially parallel to the longitudinal axis 32 of the probe.

In an exemplary aspect, and with reference to FIGS. 24A-24D, the dye carrier 70 can comprise an outer casing 76 configured to receive the at least one fluorescent dye. In this aspect, the outer casing 76 can comprise a polymer wall 78 having a thickness ranging from about 0.05 mm to about 0.5 mm. It is contemplated that different regions of the casing 76 can have different thicknesses in order to permit the casing to perform different or complementary functions. In another aspect, it is contemplated that the casing 76 can surround the dye carrier 70 and be configured to protect the dye carrier from inadvertent contact with the user or the selected tissue to be imaged. During the manufacturing process, the dye carrier 70 can be assembled to the casing 76, with dye being added to the carrier by means of (a) liquid immersion or (b) application of the dye by an applicator nozzle or tube directly onto the dye carrier. In this step, the dye carrier 70 wicks the dye into the carrier such that the carrier serves as a reservoir for the dye. It is contemplated that the dye can be selectively introduced to the carrier 70 such that the carrier is saturated, oversaturated or undersaturated with the dye.

Figure 24A:
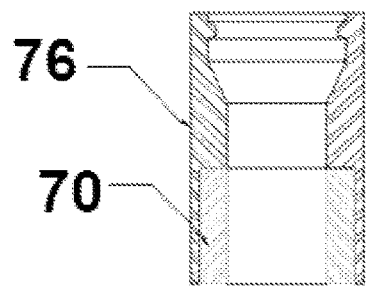
Figure 24B:
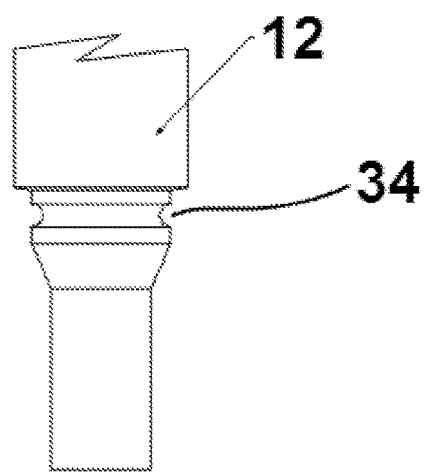
Figure 24C:
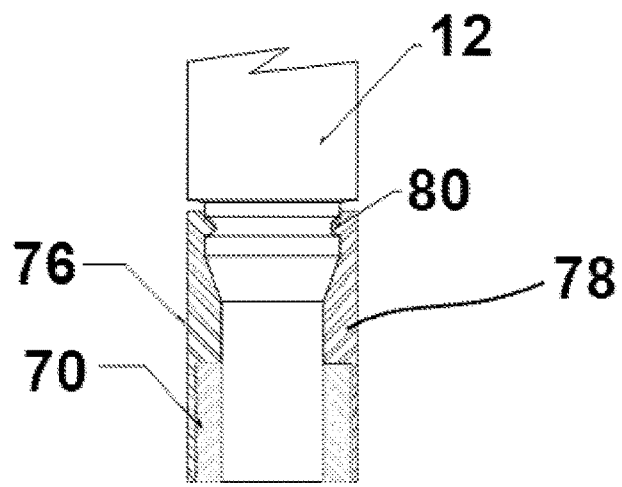
Figure 24D:
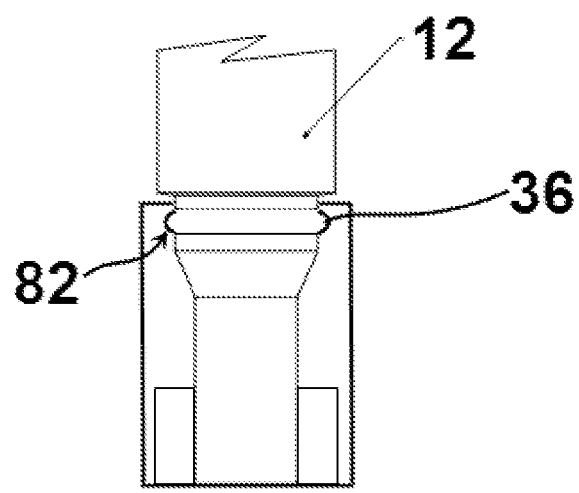

In a further aspect, the casing 76 can comprise an attachment means configured for engagement with the probe 12. In this aspect, it is contemplated that the attachment means can include conventional frictional, mechanical, and/or adhesive attachment means. In an exemplary aspect, and as shown in FIGS. 24A-24C, the attachment means can comprise one or more inwardly extending protrusions 80, and the distal end 18 of the probe 12 can define one or more engagement portions 34 that are configured to complementarily receive the one or more protrusions. Alternatively, in another exemplary aspect, and as shown in FIG. 24D, the attachment means can comprise one or more recessed portions 82, and the distal end 18 of the probe 12 can define one or more protrusions 36 that are configured for complementary receipt therein the recessed portions of the casing 76. The purpose of the engagement is to securely affix the carrier 70 to the distal end 18 of the probe 12. It is contemplated that secure and determinate fixation can position the dye carrier 70 in a desired location with respect to the probe tip 19 and also prevent inadvertent removal of the dye carrier.

Figure 25:
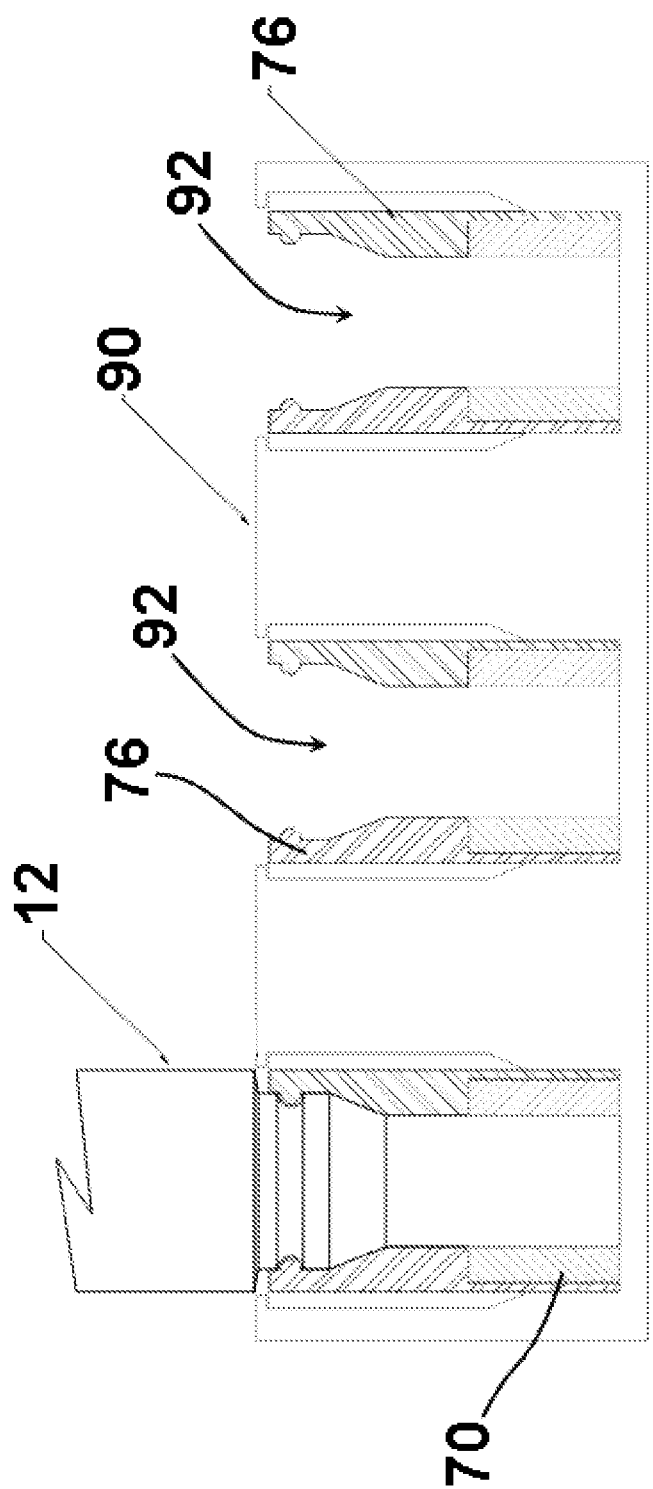
FIGS. 25-27 display exemplary packaging for storing and/or discarding dye carriers as described herein.
Figure 26:
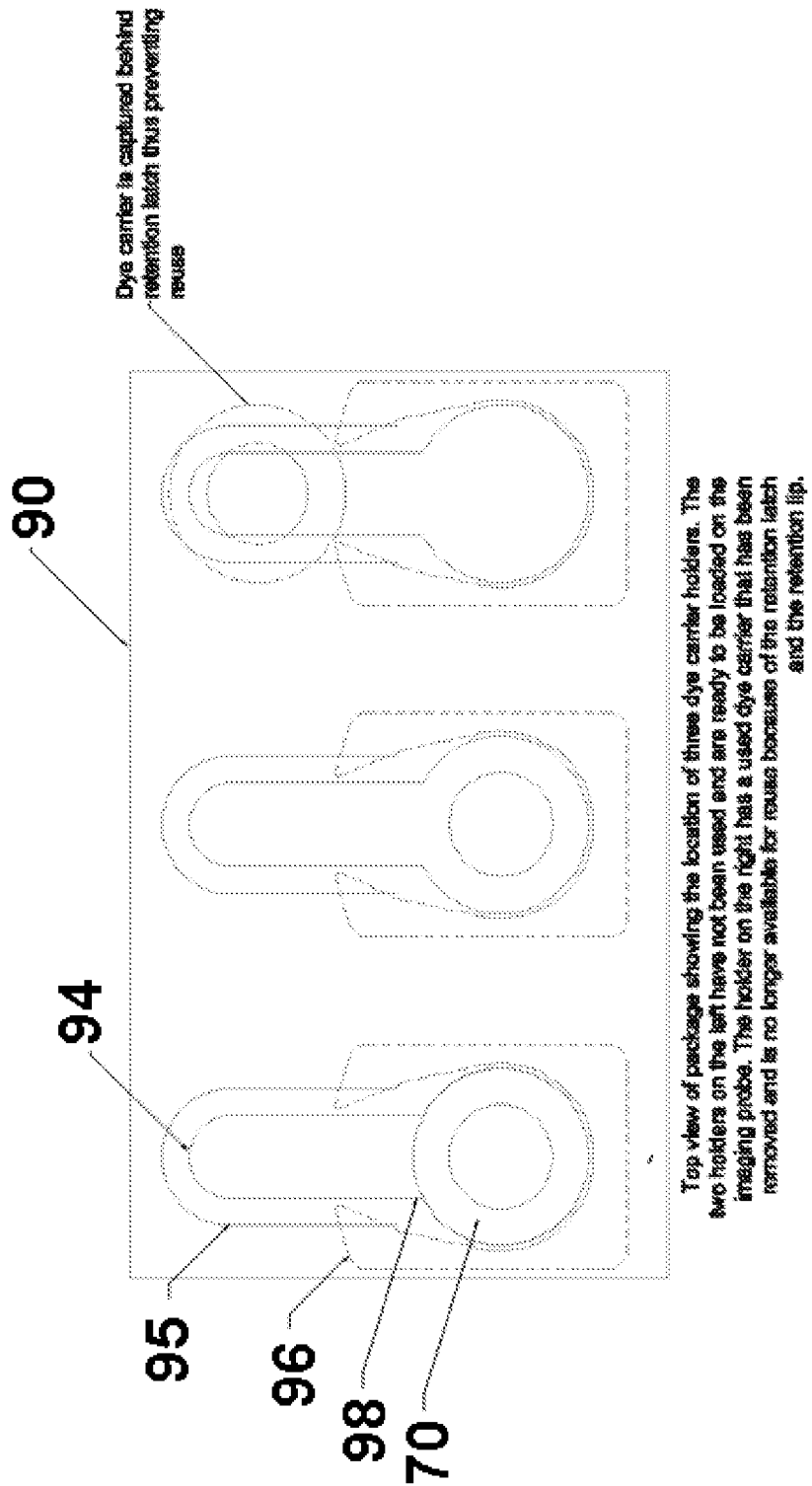
Figure 27:
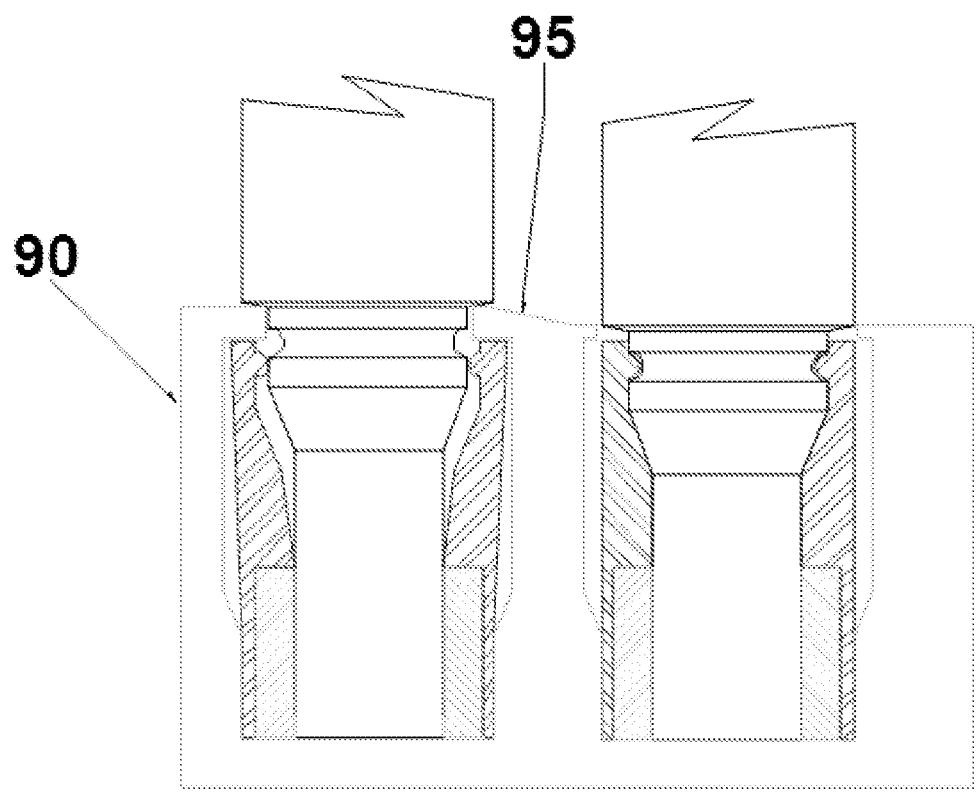

Optionally, in various aspects, as shown in FIGS. 25-27, the dye carrier assembly, which consists of at least the dye carrier 70 and the casing 76, can be provided within packaging 90 such that the carrier assembly is configured to resist attachment to, or detachment from, the distal end 18 of the probe 12 without use of the packaging. In these aspects, the packaging 90 can be required for attachment of the carrier 70, thereby ensuring correct handling and attachment of the carrier to the distal end 18 of the probe 12. Additionally, it is contemplated that the use of the packaging 90 to remove the carrier 70 can help ensure that carrier inventory is managed during the performance of a surgical procedure, thereby reducing the chance of inadvertent carrier removal. It is further contemplated that the packaging 90 can define at least one chamber 92 configured to receive a corresponding dye carrier 70 for storage, either before or after usage.

In another exemplary aspect, as shown in FIG. 27, the chambers 92 of the packaging 90 can each comprise at least one retention element 94. In one aspect, the retention element 94 can be configured to secure a respective dye carrier within the packaging 90, such as, for example and without limitation, a retention element that extends over at least a portion of a top surface of the dye carrier 70 such that the dye carrier cannot be removed without contacting the retention element. In this aspect, it is contemplated that the at least one retention element 94 can be configured for selective rotation such that, when each retention element proximate a selected dye carrier is rotated to an open position, the selected dye carrier can be removed from the packaging 90. It is further contemplated that after use of a dye carrier 70, the dye carrier can be returned to its respective chamber 92 within the package, and the at least one retention element 94 can be a removal feature 95 used to promote removal of the dye carrier as the probe 12 is withdrawn from the packaging. In another exemplary aspect, as shown in FIG. 26, the retention element 94 can be configured to receive or otherwise engage a used dye carrier 70 such that the dye carrier will not be re-used during a surgical procedure. In this aspect, it is contemplated that the packaging 90 can further comprise a latch 96 operatively positioned relative to the retention element 94 such that when a used dye carrier 70 is engaged with the retention element, the used dye carrier is further retained by the latch. It is further contemplated that the packaging 90 can cooperate with the latch 96 to define a slot 98 configured to receive a dye carrier 70 in an operative position in which the dye carrier is ready for engagement with the probe 12. In exemplary aspects, the latch 96 can project inwardly relative to the chamber 92, and a portion of the chamber can extend beyond the latch relative to slot 98. In these aspects, it is contemplated that the probe 12 can be used to advance the carrier 70 from the slot 98 through the latch 96 and into a retained position on an opposed end of the chamber from the slot. It is further contemplated that the latch 96 can be biased inwardly such that, after the probe 12 advances the carrier 70 through the latch, the latch returns to a closed position in which the carrier cannot pass back through the latch to return to the slot 98 of the chamber 90. It is contemplated that the at least one retention element 94 can comprise a lip defined by the packaging and vertically positioned relative to the carrier 70 such that the lip is configured to receive the probe 12 with the carrier being positioned underneath the lip. It is further contemplated that such an arrangement can permit removal of the probe 12 from the packaging 90 and detachment of the probe from the dye carrier 70 while the dye carrier is retained by the lip and the latch 96.

In an additional aspect, it is contemplated that the packaging 90 for a plurality of dye carriers 70 can be a cassette configured to provide an individual dye carrier among the plurality of dye carriers for use with a probe 12 as described herein.

In exemplary aspects, the casing 76 surrounds the carrier 70 and limits the dispensing of the dye to a distal portion of the carrier where it is in contact with the tissue. In these aspects, the carrier 70 also serves to prevent inadvertent contact between the user and the carrier or between the tissue and the carrier. It is contemplated that the dye within the dye carrier 70 can be released to the surface of the selected tissue by placing the carrier in contact with the selected tissue. The dye solution can be distributed onto the adjacent tissue surface according to physical mechanisms such as, for example and without limitation, wetting, capillary forces, diffusion and convection. In a further aspect, it is contemplated that the carrier 70 can also serve as a grip for the user to enhance feel and ease of handling. In this aspect, it is contemplated that the carrier 70 can be shaped for complementary receipt of at least a portion of a user's hand.

It is contemplated that the casing 76 can be a separate component from the dye carrier 70. Alternatively, it is contemplated that the casing 76 can be formed from the outer surface of the carrier 70 by coating, comolding, embossing, thermoforming or other equivalent processes such that the casing is integral to the outer portion of the carrier.

In a further aspect, the light transmission means is in communication with a light source 50 that is configured for selective generation of light at a desired wavelength. As one skilled in the art will appreciate, this allows for light of selected wavelengths to be selectively transmitted down the light transmission means and through the objective lens 60. In a further aspect, it is contemplated that the objective lens 60 can be configured to gather and focus reflected light from the selected tissue of the subject to produce an image of the selected tissue.

In a further aspect, the fluorescence imaging device 10 can comprise a means for positioning a portion of the dye carrier 70 in contact with the selected tissue of the subject to selectively diffuse the at least one fluorescent dye into the selected tissue. It is contemplated that any conventional apparatus or system for positioning a surgical device within or proximate a body of a subject can be used with the fluorescence imaging device 10. It is further contemplated that the at least one fluorescent dye can be configured to diffuse into the selected tissue up to a selected depth, such as, for example and without limitation, up to about 1 mm. Optionally, in an another aspect, it is contemplated that the means for positioning a portion of the dye carrier in contact with the selected tissue can comprise a means for steering the probe within the subject to position the dye carrier against the selected tissue. In this aspect, it is contemplated that the means for steering the probe can be configured to position the bottom surface of the dye carrier against a desired region of the selected tissue of the subject. In various aspects, the means for steering the probe can be manual, including, for example, conventional surgical tools. Alternatively, it is contemplated that the means for steering the probe can be computerized. In an exemplary aspect, the means for steering the probe comprise one or more conventional computerized micro-manipulators.

In one exemplary aspect, the dye carrier 70 can comprise a polymer foam, such as, for example and without limitation, a polyurethane (PU) or a polyester foam. In another exemplary aspect, the dye carrier can comprise a hybrid material comprising an open-cell foam filled at least partially with a hydrogel. Exemplary hydrogels include, for example and without limitation, agar, agarose, and the like. Loading of the foam with a hydrogel can be achieved by heating the hydrogel dissolved in water beyond its melting point and soaking the foam in the heated hydrogel-water mixture. It is contemplated that the at least one florescent dye can be suspended in a conventional buffer solution such that the at least one florescent dye in its buffer solution can be diffused therein at least a portion of the foam or hybrid material at a predetermined desired concentration. In one example, the at least one fluorescent dye and its buffer solution can comprise at least 95% of the dye carrier by weight. In various other exemplary aspects, it is contemplated that the at least one fluorescent dye and its buffer solution can optionally comprise at least 10% of the dye carrier by weight, at least 50% of the dye carrier by weight, or at least 75% of the dye carrier by weight. In a further aspect, the dye carrier can further comprise at least one conjugated agent, such as, for example and without limitation, an antibody. In this aspect, it is contemplated that each conjugated agent can be conjugated to a selected biomarker. It is further contemplated that the at least one conjugated agent can comprise a first conjugated agent conjugated to a first biomarker and a second conjugated agent conjugated to a second biomarker that is different from the first biomarker. It is still further contemplated that the dye carriers described herein, including the dye carriers described herein as comprising at least one conjugated agent, can be configured for use with fluorescent imaging systems comprising light sources that are configured to generate light at multiple wavelengths.

Loading of the dye carrier, as well as the diffusive properties of the dye carrier, can be controlled by the material properties of the dye carrier, including, for example and without limitation, the porosity of the polymer foam and the concentration of the hydrogel constituents. The properties of the dye carrier, including, for example and without limitation, the foam material, the foam porosity, the hydrogel type, the percent solids within the hydrogel, and the additives in the foam, dye carrier or dye, can be selected to adjust the functions of the dye carrier, including wicking, reservoir and delivery.

Figure 1D:
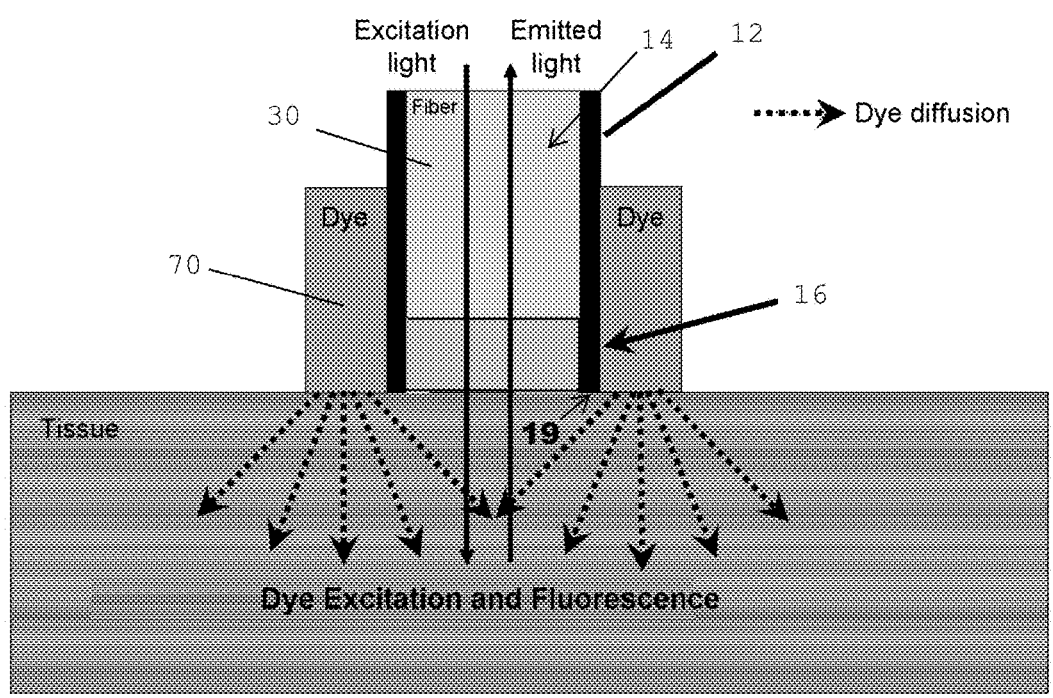

In an additional aspect, as shown in FIG. 1D, the central bore 14 of the probe 12 can have a substantially constant diameter (corresponding to an inner diameter of the probe) along the longitudinal length of the probe. Alternatively, it is contemplated that the central bore 14 of the probe 12 can have a variable diameter along the longitudinal length of the probe. In one aspect, as shown in FIGS. 1A-1C, it is contemplated that the diameter of the central bore 14 of the probe 12 can be reduced proximate the distal tip 19 of the probe. In this aspect, as shown in FIG. 1A, it is contemplated that the outer diameter of the probe 12 can remain substantially constant along the longitudinal length of the probe. Alternatively, as shown in FIG. 1C, it is contemplated that the outer diameter of the probe 12 can vary along the longitudinal length of the probe; for example, it is contemplated that the outer diameter of the probe can be reduced proximate the distal tip 19 of the probe (corresponding to the portion of the probe where the diameter of the central bore 14 is reduced).

In a further aspect, as shown in FIG. 1B, the outer surface 16 of the probe 12 can define one or more protrusions 26 proximate the distal end 18 of the probe. In this aspect, it is contemplated that the dye carrier 70 can comprise one or more channels 74 configured to receive corresponding protrusions 26 of the probe. It is contemplated that the one or more protrusions 26 of the probe can be configured to engage the dye carrier 70 such that the dye carrier is detachably secured thereto the probe 12. In one aspect, the one or more protrusions 26 can comprise a rim 28 extending circumferentially around the probe 12 along at least a portion of the outer surface 16 of the probe. In another aspect, it is contemplated that the one or more protrusions 26 can comprise a plurality of spaced protrusions positioned substantially equidistant from the distal tip of the probe.

In another exemplary aspect, the dye carrier 70 can be formed from a hydrogel having an area configured for contact with the selected tissue of the subject ranging from between about 1 to about 28 mm². In another exemplary aspect, a hydrogel dye carrier can comprise about 5% agar and about 95% water. In still another exemplary aspect, prior to application of a formed hydrogel dye carrier to the selected tissue, it is contemplated that between about 0.1 to about 0.5 mg of a fluorescent dye, such as, for example and without limitation, dextran conjugated Alexa 488 and dextran conjugated Texas Red (both from Invitrogen), in its conventional buffer solution can be loaded on the hydrogel dye carrier and allowed to diffuse into the dye carrier for about 1 min.

As one skilled in the art will appreciate, the devices, systems, and methods described herein rely on fluorescence as an imaging mode, primarily due to the high degree of sensitivity afforded by the fluorescence imaging technique coupled with the ability to specifically target structural components and dynamic processes in chemically fixed as well as living cells and tissues. Many fluorescent probes have been constructed around synthetic aromatic organic chemicals designed to bind with a biological macromolecule (for example, a protein or nucleic acid) or to localize within a specific structural region, such as the cytoskeleton, mitochondria, Golgi apparatus, endoplasmic reticulum, and nucleus. Other fluorescent probes are employed to monitor dynamic processes and localized environmental variables, including concentrations of inorganic metallic ions, pH, reactive oxygen species, and membrane potential. Fluorescent dyes are also useful in monitoring cellular integrity (live versus dead and apoptosis), endocytosis, exocytosis, membrane fluidity, protein trafficking, signal transduction, and enzymatic activity. Despite the numerous advances made in fluorescent dye synthesis during the past few decades, there is very little solid evidence about molecular design rules for developing new fluorochromes, particularly with regard to matching absorption spectra to available fluorescence laser excitation wavelengths. As a result, the number of fluorophores that have found widespread use in fluorescence microscopy is a limited subset of the many thousands that have been discovered.

Fluorophores chosen for fluorescence imaging applications generally are selected to exhibit an excitability, intensity of emitted lights, and signal persistence sufficient for the instrument to obtain image data that does not suffer from excessive photobleaching artifacts and low signal-to-noise ratios. In widefield fluorescence microscopy, excitation illumination levels are easily controlled with neutral density filters, and the intensity can be reduced (coupled with longer emission signal collection periods) to avoid saturation and curtail irreversible loss of fluorescence. Excitation conditions in confocal microscopy are several orders of magnitude more severe, however, and restrictions imposed by characteristics of the fluorophores and efficiency of the microscope optical system become the dominating factor in determining excitation rate and emission collection strategies.

In fluorescence microscopy, excitation of the fluorophores with a focused laser beam at high power densities increases the emission intensity up to the point of dye saturation, a condition having parameters that are dictated by the excited state lifetime. In the excited state, fluorophores are unable to absorb another incident photon until they emit a lower-energy photon through the fluorescence process. When the rate of fluorophore excitation exceeds the rate of emission decay, the molecules become saturated and the ground state population decreases. As a result, a majority of the laser energy passes through the specimen undiminished and does not contribute to fluorophore excitation. Balancing fluorophore saturation with laser light intensity levels helps to achieve a desired signal-to-noise ratio in fluorescence imaging applications.

The number of fluorescent probes currently available for fluorescence microscopy runs in the hundreds, with many dyes having absorption maxima closely associated with common laser spectral lines. An exact match between a particular laser line and the absorption maximum of a specific probe is not always possible, but the excitation efficiency of lines near the maximum is usually sufficient to produce a level of fluorescence emission that can be readily detected. For example, in FIG. 8 the absorption spectra of two common probes are illustrated, along with the most efficient laser excitation lines. The green spectrum is the absorption profile of fluorescein isothiocyanate (FITC), which has an absorption maximum of 495 nanometers. Excitation of the FITC fluorophore at 488 nanometers using an argon-ion laser produces an emission efficiency of approximately 87 percent. In contrast, when the 477-nanometer or the 514-nanometer argon-ion laser lines are used to excite FITC, the emission efficiency drops to only 58 or 28 percent, respectively. One skilled in the art will appreciate that, in this example, the 488-nanometer argon-ion (or krypton-argon) laser line is the most efficient source for excitation of this fluorophore.

Figure 8:
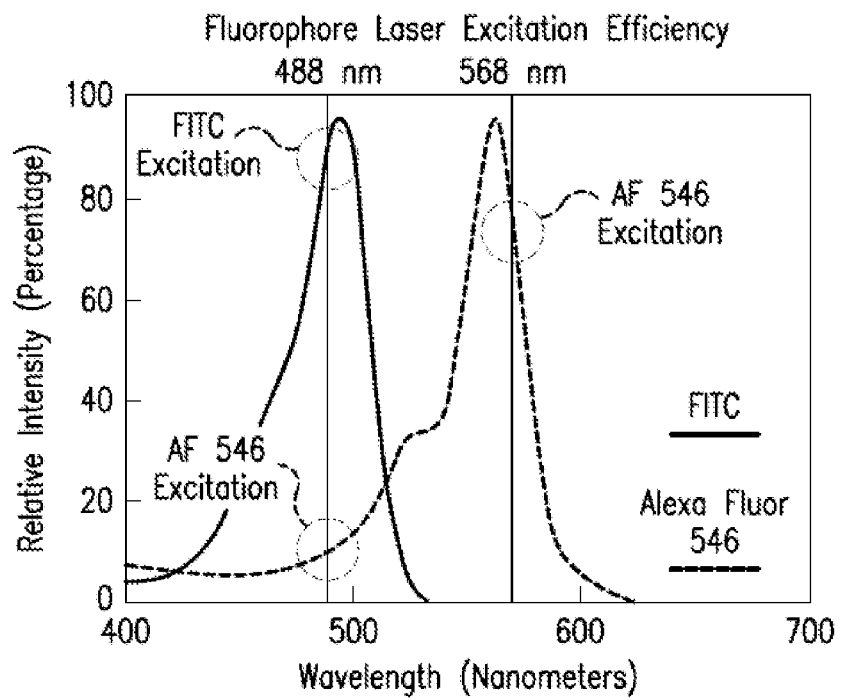
FIG. 8 shows the absorption profile of fluorescein isothiocyanate (FITC) in green and the absorption profile of Alexa Fluor 546 in red.

The red spectrum in FIG. 8 is the absorption profile of Alexa Fluor 546, a bi-sulfonated alicyclic xanthene (rhodamine) derivative with a maximum extinction coefficient at 556 nanometers, which is designed specifically to display increased quantum efficiency at significantly reduced levels of photobleaching in fluorescence experiments. The most efficient laser excitation spectral line for Alexa Fluor 546 is the yellow 568-nanometer line from the krypton-argon mixed gas ion laser, which produces an emission efficiency of approximately 84 percent. The next closest laser spectral lines, the 543-nanometer line from the green helium-neon laser and the 594-nanometer lines from the yellow helium-neon laser, excite Alexa Fluor 546 with an efficiency of 43 and 4 percent, respectively.

Instrumentally, and as one skilled in the art will appreciate, fluorescence emission collection of the fluorescence microscopic imaging system can be optimized by careful selection of objectives, detector aperture dimensions, dichromatic and barrier filters, as well as maintaining the optical train in precise alignment. In most cases, low magnification objectives with a high numerical aperture should be chosen for the most demanding imaging conditions because light collection intensity increases as the fourth power of the numerical aperture, but only decreases as the square of the magnification. However, resolution can be improved with high magnification objectives. Generally, it is appropriate to focus on restrictions imposed by the physical properties of the fluorophores themselves.

The choice of fluorescent probes for fluorescence microscopy generally should address the specific capabilities of the instrument to excite and detect fluorescence emission in the wavelength regions made available by the light source and detectors. Although the light sources used in fluorescence microscopy produce discrete lines in the ultraviolet, visible, and near-infrared portions of the spectrum, the location of these spectral lines does not always coincide with absorption maxima of popular fluorophores. In fact, it is not necessary for the laser spectral line to correspond exactly with the fluorophore wavelength of maximum absorption, but the intensity of fluorescence emission is regulated by the fluorophore extinction coefficient at the excitation wavelength (as discussed above). The most popular lasers for confocal microscopy are air-cooled argon and krypton-argon ion lasers, the new blue diode lasers, and a variety of helium-neon systems. Collectively, these lasers are capable of providing excitation at ten to twelve specific wavelengths between about 400 and 650 nanometers.

In a further aspect, the fluorescent dyes for the devices, methods, and systems described herein can be selected based on their molecular weight. Studies have shown that fluorescent dyes having a given molecular weight may not be able to diffuse through particular tissues of interest. For example, Andries and Brutsaert demonstrated that fluorescent dyes that are conjugated to dextran with a molecular weight of 40 kDa did not diffuse through either endocardial endothelium or capillary endothelium, but those with 10 kDa did diffuse easily. Thus, it is desirable to select a molecular weight fluorescent dye that can be introduced and/or diffused into the tissue on interest within a desired time period. See Andries U, Brutsaert DL. Endocardial endothelium in the rat: junctional organization and permeability. Cell Tissue Res. 1994 September; 277(3):391-400.

In exemplary aspects, it is contemplated that introduction of fluorescent dyes that have a molecular weight of between about 3 to about 10 kDa via a dye carrier can be quasi instantaneously available for tissue imaging. In various exemplary aspects, it is further contemplated that the molecular weight of the at least one fluorescent dye can optionally be less than 40 KDa, less than 20 Kda, or less than 10 Kda.

As exemplarily discussed above, the at least one fluorescent dye can comprise an Alexa Fluor dye. The Alexa Fluor dyes produced by Molecular Probes (Alexa Fluor is a registered trademark of Molecular Probes) are sulfonated rhodamine derivatives that exhibit higher quantum yields for more intense fluorescence emission than spectrally similar probes, and have several additional improved features, including enhanced photostability, absorption spectra matched to common laser lines, pH insensitivity, and a high degree of water solubility. The resistance to photobleaching of Alexa Fluor dyes is high enough that even when subjected to irradiation by high-intensity laser sources, fluorescence intensity generally remains stable for some periods of time even in the absence of antifade reagents. This feature enables the water soluble Alexa Fluor probes to be readily utilized for both live-cell and tissue section investigations, as well as in traditional fixed preparations.

As one skilled in the art will appreciate, the Alexa Fluor dyes are available in a broad range of fluorescence excitation and emission wavelength maxima, ranging from the ultraviolet and deep blue to the near-infrared regions. Alphanumeric names of the individual dyes are associated with the specific excitation laser or arc-discharge lamp spectral lines for which the probes are intended. For example, Alexa Fluor 488 is designed for excitation by the blue 488-nanometer line of the argon or krypton-argon ion lasers, while Alexa Fluor 568 is matched to the 568-nanometer spectral line of the krypton-argon laser. Several of the Alexa Fluor dyes are specifically designed for excitation by either the blue diode laser (405 nanometers), the orange/yellow helium-neon laser (594 nanometers), or the red helium-neon laser (633 nanometers). Other Alexa Fluor dyes are intended for excitation with traditional mercury arc-discharge lamps in the visible (Alexa Fluor 546) or ultraviolet (Alexa Fluor 350, also useful with high-power argon-ion lasers), and solid-state red diode lasers (Alexa Fluor 680). Because of the large number of available excitation and emission wavelengths in the Alexa Fluor series, multiple labelling experiments can often be conducted exclusively with these dyes.

Alexa Fluor dyes are commercially available as reactive intermediates in the form of maleimides, succinimidyl esters, and hydrazides, as well as prepared cytoskeletal probes (conjugated to phalloidin, G-actin, and rabbit skeletal muscle actin) and conjugates to lectin, dextran, streptavidin, avidin, biocytin, and a wide variety of secondary antibodies. In the latter forms, the Alexa Fluor fluorophores provide a broad palette of tools for investigations in immunocytochemistry, neuroscience, and cellular biology. The conjugated forms of Alexa Fluor dyes can mediate dye transport and uptake. The family of probes has also been extended into a series of dyes having overlapping fluorescence emission maxima targeted at sophisticated confocal microscopy detection systems with spectral imaging and linear unmixing capabilities. For example, Alexa Fluor 488, Alexa Fluor 500, and Alexa Fluor 514 are visually similar in color with bright green fluorescence, but have spectrally distinct emission profiles. In addition, the three fluorochromes can be excited with the 488 or 514-nanometer spectral line from an argon-ion laser and are easily detected with traditional fluorescein filter combinations. In multispectral (x-y-l; referred to as a lambda stack) confocal imaging applications, optical separation software can be employed to differentiate between the similar signals. The overlapping emission spectra of Alexa Fluor 488, 500, and 514 can be segregated into separate channels and differentiated using pseudocolor techniques when the three fluorophores are simultaneously combined in a triple label investigation.

Fluorophores designed to probe the internal environment of living cells have been widely examined by a number of investigators, and many hundreds have been developed to monitor such effects as localized concentrations of alkali and alkaline earth metals, heavy metals (employed biochemically as enzyme cofactors), inorganic ions, thiols and sulfides, nitrite, as well as pH, solvent polarity, and membrane potential. These probes bind to the target ion with a high degree of specificity to produce the measured response and are often referred to as spectrally sensitive indicators. Ionic concentration changes are determined by the application of optical ratio signal analysis to monitor the association equilibrium between the ion and its host. The concentration values derived from this technique are largely independent of instrumental variations and probe concentration fluctuations due to photobleaching, loading parameters, and cell retention. One fluorphore that has been approved for human use is Fluorescite® which is supplied as a 10% solution of fluorescein sodium in saline and is used as an injectable intravenous agent for diagnostic purposes.

Figure 3:
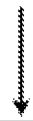
Figure 3:
Figure 3:

As noted above, and with reference to FIGS. 2-3, a fluorescence microscopic imaging system 100 can include a processor 40 that is coupled to a control subsystem and a display, if needed. A memory is coupled to the processor. The memory can be any type of computer memory, and is typically referred to as random access memory "RAM," in which the system software, and image reconstruction software resides. The fluorescence microscopic imaging system's controls the acquisition and processing of the received emitted light and allows the fluorescence microscopic imaging system to display a two-dimensional or three-dimensional fluorescence image, as desired. In one aspect, the system software and image reconstruction software, can comprise one or more modules to acquire, process, and display data from the fluorescence microscopic imaging system. The software comprises various modules of machine code, which coordinate the fluorescence microscopic imaging subsystems.

Data is acquired from emitted light of the excited tissue regions of interest. The emitted light can be communicated to the fluorescence microscopic imaging system 100 via the fiber-optic bundle 30, where the emitted light is measured and processed to form images, and then, if desired, displayed on a display. The system software and image reconstruction software allow for the management of multiple acquisition sessions and the saving and loading of data associated with these sessions. Post processing of the image data is also enabled through the system software and the image reconstruction software.

As one skilled in the art will appreciate, the fluorescence microscopic imaging system 100 can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), and the like.

The software of the fluorescence microscopic imaging system can comprise executable instructions for implementing control and processing functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory), a digital versatile disc (DVD), and a portable compact disc read-only memory (CDROM). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory can include the image data obtained by the fluorescence microscopic imaging system and can also include raw data representative of the acquired light. A computer readable storage medium can be coupled to the processor for providing instructions to the processor to instruct and/or configure the processor to perform steps or algorithms related to the operation of the fluorescence microscopic imaging system. The computer readable medium can include hardware and/or software such as, by way of example only, magnetic disks, magnetic tape, optically readable media such as CD ROM's, and semiconductor memory such as PCMCIA cards. In each case, the media may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The fluorescence microscopic imaging system 100 can include a control subsystem to direct operation of various components of the fluorescence microscopic imaging system. The control subsystem and related components may be provided as software for instructing a general or special purpose processor or as specialized electronics in a hardware implementation. The control subsystem is connected to the light source to transmit the desired light at the desired wavelength to the fiber-optic bundle.

The fluorescence microscopic imaging system 100 can include an image construction subsystem for converting the electrical signals generated by the received emitted light to data that can be manipulated by the processor and that can be rendered into an image. In various exemplary aspects, it is contemplated that the imaging system can provide images with a resolution of between about 0.5 µm to about 100 µm. The image construction subsystem can be directed by the control subsystem to operate on the received emitted light data to render an image. In a further exemplary aspect, the control subsystem can also comprise a motor control subsystem that is configured to provide a motor control signal to a motor to control the movement of the distal end of the probe (and the dye carrier) to a desired a location on or within the subject.

In operation, it is contemplated that the distal end of the probe (and, consequently, the dye carrier) is steered through blood vessels or body cavities to a location adjacent to a selected tissue of the subject. Subsequently, the dye carrier is brought in contact with the selected tissue, and the florescent dye(s) are allowed to diffuse from the dye carrier into the tissue. The fluorescent dye is then excited by a light source, such as a focused laser beam, of appropriate wavelength to emit light of a different wavelength for transmission through the image transmission means of the probe. As one will appreciate, scanning through tissue by exciting the dye and measuring intensities of emitted light allows for two- and three-dimensional imaging via a fluorescence microscopic imaging system, such as described herein.

According to one aspect, a method for producing a fluorescence image of a selected tissue comprises generating light at a desired wavelength, transmitting the light into the image transmission means and through the objective lens of the probe onto a portion of the selected tissue of the subject into which the one or more fluorescent dyes have been introduced, thereby exciting the fluorescent dye therein the selected tissue. Subsequently, emitted light of a different wavelength is emitted by the excited fluorescent dye and is received therethrough the objective lens and into the image transmission means, which is operatively coupled to a conventional fluorescence microscopic imaging system such as described herein. From the measured intensities of emitted light, one-, two- or three-dimensional images of the selected tissue can be created using digital image processing techniques, such as, for example and without limitation, deconvolution, filtering, and segmentation. It is contemplated that the processor of the fluorescence microscopic imaging system can be configured to characterize tissue texture for a particular fluorescence image using Fourier decomposition and other known statistical methods, such as image moments for various orders.

It is contemplated that the fluorescence imaging devices and systems described herein can be configured for complementary use with any known devices and systems for discriminating among tissue types. It is further contemplated that the fluorescence imaging devices and systems described herein can be configured to be an integral part of tissue discrimination systems, including those tissue discrimination systems that are used intrasurgically.

It is also contemplated that the hybrid material comprising an open-cell polymer foam at least partially filled with a hydrogel, as described herein, can be configured for use in a variety of applications beyond the tissue imaging context, including, for example and without limitation, fluorescent imaging of materials and delivery of drugs and/or contrast agents.

An exemplary fluorescence imaging device and system is disclosed in U.S. Patent Publication No. 2011/0301438, the disclosure of which is hereby incorporated by reference in its entirety.

Exemplary Systems for Imaging of Cardiac Tissue

Described herein are systems and methods for fluorescence imaging of cardiac tissue. In one aspect, the system for fluorescence imaging can comprise means for dispensing at least one fluorescent dye into a selected region of a tissue. In exemplary aspects, the tissue of interest comprises cardiac tissue. It is contemplated that the at least one fluorescent dye can comprise any known fluorescent dye, such as, for example and without limitation, Alexa, Texas Red, FITC, Oregon Green, Rhodamine Green, Lucifer yellow, Fluo 3, Fluo 4, di-8-Anepps, Fluorescite, and the like. It is further contemplated that the at least one fluorescent dye can comprise at least one fluorescent calcium-sensitive dye, such as, for example and without limitation, fura-2, fluo-4, and the like. It is still further contemplated that the at least one fluorescent dye can be any known voltage-sensitive dye, including, for example and without limitation, ANNINE-6plus and di-8-anepps. In another aspect, the system for fluorescence imaging can comprise a light source configured to transmit light to the selected region of the tissue. In an additional aspect, the system for fluorescence imaging can comprise means for receiving emitted light from the at least one fluorescent dye. In this aspect, it is contemplated that the means for receiving emitted light can be configured to produce an image of the selected region of the tissue in which from about 1 µm to about 10 µm of cleft space is visible between cells within the tissue.

In a further aspect, the system for fluorescence imaging can comprise a processor in operative communication with the means for receiving emitted light. In this aspect, it is contemplated that the processor can be configured to process the received emitted light from the at least one fluorescent dye. In one aspect, the processor can be configured to process the received emitted light to generate a fluorescence image of the selected region of the tissue. In another aspect, the processor can be configured to process the received emitted light to characterize the microstructure of the imaged tissue. In this aspect, it is contemplated that the microstructure of the imaged tissue can be characterized as an electrical conduction profile within the selected region of the tissue. In another aspect, it is contemplated that the characterization of the tissue microstructure can be performed in real-time during the performance of surgical procedures. Optionally, in an additional aspect, the processor can be configured to identify conductive tissue within the selected region of the tissue. In this aspect, it is contemplated that the processor can generate a map of the electrical conduction pathways within the selected region of the cardiac tissue. It is further contemplated that the processor can be configured to graphically identify conductive tissue within a fluorescence image of the imaged tissue. In an exemplary aspect, the processor can be configured to generate a color-coded map of the various tissue types within the selected region of the tissue. In this aspect, it is contemplated that the color-coded map can graphically indicate regions of the imaged tissue that are acceptable for cutting during a surgical procedure, as well as those that should not be cut during a surgical procedure. It is further contemplated that the regions of the imaged tissue that are acceptable for cutting can exemplarily be shown as green on the map and that the regions of tissue that should not be cut can exemplarily be shown as red on the map. In various aspects, the processor can be configured to produce an output comprising both graphical and textual information, including, for example and without limitation, textually descriptive or qualitative information. For example, in one exemplary aspect, the processor can be configured to generate an image of the selected region of the tissue that includes textual identifications of one or more of the distinct tissue types displayed in the image. In another exemplary aspect, the processor can be configured to identify nodal tissue within the selected region of the imaged tissue. In a further exemplary aspect, the processor can be configured to produce an output comprising qualitative numbers that are indicative of the percentage of probability that a particular tissue area corresponds to a particular tissue type.

It is contemplated that the processor can be configured to identify conductive tissue within the selected region of the tissue using various image texture analysis methods. In an exemplary aspect, the processor can be configured to identify striations in the imaged tissue through first and higher-order gradient filtering. In this aspect, it is contemplated that image of the tissue can be processed to identify the gradient directions within the tissue. It is further contemplated that a distinct tissue type, such as, for example, nodal tissue, within the imaged tissue can correspond to the regions of the imaged tissue that have substantially varying gradient directions. In another exemplary aspect, it is contemplated that the processor can be configured to perform statistical analyses of signal intensity distributions in the image sequence. In this aspect, covariance tensors can be analyzed to identify variations in tissue micro-structure. In another exemplary aspect, it is contemplated that the processor can be configured to perform a multi-dimensional Fourier analysis on the image of the tissue to thereby produce a spectrum characterizing one or more of tissue alignment, tissue arrangement, tissue function, and tissue distribution. In this aspect, it is contemplated that Gaussian filters and methods of image deconvolution can be applied to the image prior to the Fourier analysis to thereby reduce noise and blurring in the image such that it is more easily analyzed by a user.

It is contemplated that the process can comprise multiple processor cores and be extended with one or more graphics processing units (GPUs) to facilitate real-time processing and analysis of image data.

Thus, it is contemplated that the disclosed system can be used to discriminate among electrically conductive and non-conductive tissue in real-time, thereby permitting a surgeon to avoid damage to nerves and other conduction pathways while also validating the function of such conduction pathways. It is further contemplated that the disclosed systems can be configured for complementary use with other imaging modalities, such as, for example and without limitation, magnetic resonance imaging (MRI), ultrasonic imaging (ultrasound), and computer tomographic (CT) imaging.

Referring to FIGS. 1-1C, 17, and 24-27, in one exemplary aspect, the means for receiving emitted light can comprise a fluorescence imaging device for use with the processor, which can be a part of a conventional confocal microscopic imaging system that is configured to produce a fluorescence image of a portion of a selected tissue of a subject. In one aspect, the fluorescence imaging device can comprise a probe and a dye carrier. Optionally, the fluorescence imaging device can have a probe 12 and dye carrier 70 as described herein. Another exemplary fluorescence imaging device is described in U.S. Patent Publication No. 2011/0301438, the disclosure of which is hereby incorporated by reference in its entirety.

In one embodiment, a subject is connected to electrocardiogram (ECG) electrodes to obtain a cardiac electrical signal from the subject. In one aspect, the cardiac signal from the electrodes can be transmitted to an ECG amplifier to condition the signal for provision to a fluorescence microscopic imaging system. It is recognized that a signal processor or other such device can be used instead of an ECG amplifier to condition the signal. If the cardiac signal from the electrodes is suitable as obtained, then use of an amplifier or signal processor could be avoided entirely.

In this aspect, the fluorescence microscopic imaging system can include an ECG signal processor that, if necessary, is configured to receive signals from an ECG amplifier. The ECG signal processor can be configured to provide signals to the control subsystem. The ECG signal can be used to trigger transmission by the source of light, e.g., a laser, of a single or a number of pulses of light (a pulse train). The fluorescence microscopic imaging system transmits and receives emitted light data, can provide an interface to a user to control the operational parameters of the fluorescence microscopic imaging system, and, in an exemplary aspect, can process data appropriate to formulate an ECG-triggered image.

In one example, the fluorescence microscopic imaging system can detect a trigger signal from the ECG signal processing module. The trigger signal is based on a subject's ECG signal, which is provided to the ECG signal processing module though use of ECG electrodes and, if necessary, the ECG amplifier. The ECG processing module of the fluorescence microscopic imaging system can be configured to automatically detect, the peak of a fixed and repeatable point on the ECG signal trace, such as, for example and without limitation, the R-wave, the P-wave, Q-wave, S-wave, and T-wave or features thereof, from which the transmission of radiation therethrough the probe to the selected tissue is triggered. Of course, other ECG features or signals of the subject's cardiac activity, such as, for example and without limitation, acoustic signals or signals measured with ultrasound can also be used to trigger the imaging system. Each feature referred to above can represent a reference point, which can trigger the image acquisition or provide a marker for selection of images.

In another aspect, it is contemplated that an ECG trace can comprise at least a first and a second of the above described wave peaks. Each peak can provide a reference point of the ECG signal for triggering transmission of radiation energy. When a peak of a given wave type is selected to trigger the transmission of light, subsequent peaks of the same wave type can be used to trigger subsequent transmissions of light.

In operation, it is contemplated that the means for dispensing the at least one fluorescent dye, such as, for example and without limitation, the probe (and, consequently, the dye carrier) is steered through blood vessels or body cavities to a location adjacent to a selected tissue of the subject. Subsequently, the fluorescent dyes are allowed to diffuse into the tissue. The fluorescent dye is then excited by a light source, such as a focused laser beam, of appropriate wavelength to emit light of a different wavelength. In exemplary aspects, the emitted light can be transmitted through the fiber optics bundle of the probe. As one will appreciate, scanning through tissue by exciting the dye and measuring intensities of emitted light allows for two- and three-dimensional imaging via a fluorescence microscopic imaging system, such as described herein.

According to one aspect, a method for producing a fluorescence image of a selected tissue comprises generating light at a desired wavelength, and transmitting the light into onto a portion of the selected tissue of the subject into which the one or more fluorescent dyes have been introduced, thereby exciting the fluorescent dye therein the selected tissue. Subsequently, emitted light of a different wavelength is emitted by the excited fluorescent dye and is received by the means for receiving the emitted light, which, in exemplary aspects, can comprise the objective lens and the fiber-optic bundle, and which can be operatively coupled to the fluorescence microscopic imaging system. From the measured intensities of emitted light, one-, two- or three-dimensional images of the selected tissue can be created using digital image processing techniques, such as, for example and without limitation, deconvolution, filtering, and segmentation. It is contemplated that the processor of the fluorescence microscopic imaging system can be configured to characterize tissue texture for a particular fluorescence image using Fourier decomposition and other known statistical methods, such as image moments for various orders as exemplarily described herein.

According to another embodiment, a method for producing an ECG-triggered image comprises generating light at a desired wavelength, repeatedly transmitting the light into a subject at a desired location within the subject, wherein a reference point of an ECG signal taken from the subject triggers each sequential light transmission, receiving emitted light emitted from the excited fluorescent dye at the desired location as a result of each light transmission, and processing the received emitted light data to form the fluorescence image. In one exemplary aspect, a high resolution fast multi-spectral fluorescence mapping technique and apparatus can be used.

EXPERIMENTAL EXAMPLES

Although the experiments described below were performed using probes and dye carriers that are different from some of those described and claimed herein, it is understood that the below-described experimental data provides general support for the ability of fluorescence imaging devices, such as those described herein, to perform similar experiments and produce fluorescence images of selected tissues of a subject, including, for example and without limitation, cardiac tissue. Additionally, the following examples are meant to provide an indication of the ability to characterize cardiac tissue using fluorescence imaging methods and should not be construed as limiting the scope of the claimed systems and methods.

Example One

Figure 9:
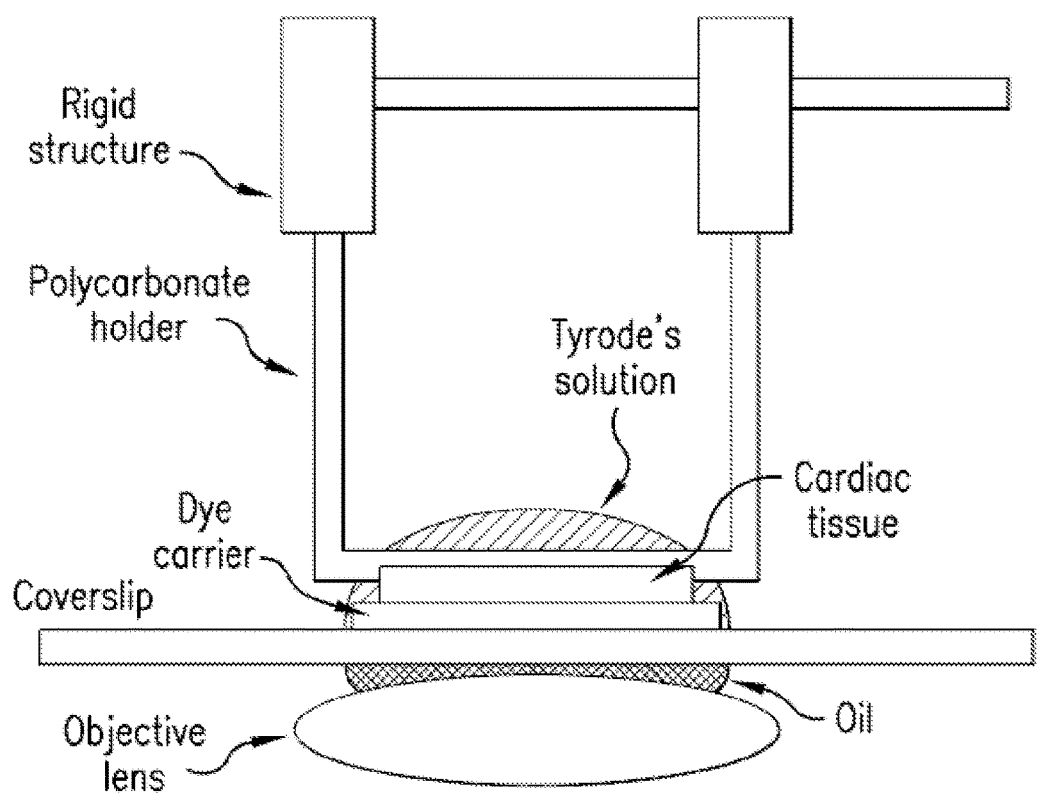
FIGS. 9-16 reflect experiments that were performed using probes and dye carriers that are different from the devices described herein and depicted in FIGS. 1-3. However, it is contemplated that the experiments described herein and depicted in FIGS. 9-16 could be similarly performed with the devices described herein and depicted in FIGS. 1-3. Thus, FIGS. 9-16 and the corresponding portions of the application provide support for the ability of the claimed devices to produce confocal images of the tissue of a subject.

In one experimental procedure, adult rabbits were anesthetized with pentobarbital (30 mg/kg) and anticoagulated with heparin (2500 USP units/kg). Following thoracotomy, the rabbit hearts were quickly excised and placed in a modified oxygenated Tyrode's solution (in mM: 126 NaCl, 11 Dextrose, 0.1 CaCl2, 13.2 KCl, 1 MgCl2, 12.9 NaOH, 24 HEPES) at room temperature. The hearts were dissected into tissue sections of three types: right ventricular papillary muscle (≈1 mm×1 mm×5 mm), subepicardial ventricular (≈6 mm×2 mm) and atrial tissue (≈6 mm×2 mm) The sections were secured to a polycarbonate holder with sutures as shown in FIG. 9 and stored in the solution until imaging.

The images were obtained within 6 h of heart isolation. Tissue sections were covered by oxygenated Tyrode's solution during the imaging (FIG. 9). Tissue sections were imaged on an 8-bit BioRad MRC-1024 laser-scanning confocal microscope (BioRad, Hercules, Calif.) with a 40× oil-immersion objective lens (Nikon, Tokyo, Japan). Three-dimensional image stacks with a spatial resolution of 200× 200×200 nm were obtained with a field of view (X×Y) of 204.8×153.6 µm extending up to 80 µm into the myocardium (Z direction). The Z-axis was substantially parallel to the laser beam direction.

Thin hydrogel slices (4 mm×4 mm×40 µm thick) were created using 6.5% agar (GenePure LE Agarose, ISC Bio-Express, Kaysville, Utah) in water. These slices were placed in solutions of fluorescent dyes and the dye was allowed to diffuse into the agar hydrogel. Dextran-conjugated, lysine fixable Texas Red with a molecular weight of 3 kDa and excitation/emission wavelengths of 595/615 nm was used at concentrations of 6-12 mg/mL (Molecular Probes, Eugene, Oreg.). This dye and other dextran-conjugated dyes allow for specific labelling of the extracellular space. An imaging chamber was created by cutting an aperture from the bottom of a polystyrene weighing dish and gluing a size #0 glass slide over the opening. The dye-loaded hydrogel slice was placed on the glass slide and dye was delivered by gently pressing the tissue onto the slide. Precautions were taken to ensure that the tissue sample was not compressed in the imaged region. Image regions with a distance of at least 10 µm between the glass slide and tissue surface were used. As shown in FIG. 9, images were acquired by imaging through the glass slide and hydrogel.

Image stacks were deconvolved with the iterative Richardson-Lucy algorithm using a measured point spread function (PSF). Briefly, the response g of an imaging system to given sources can be described by convolution of the source image f with the point spread function h:

$$g(x)=(f*h)(x)=\iiint_{-\infty}^{\infty} f(x')h(x-x')dx'$$

The iterative Richardson-Lucy algorithm was used to reconstruct the source image f:

$$g_{n+1} = g_n\left(\frac{g_0}{g_n * h} \otimes h\right)$$

with the cross-correlation operator $\otimes$ and $g_0=g$. The three-dimensional PSF was characterized by imaging 100 nm fluorescent beads embedded in agar. Images of fifteen beads were extracted, aligned and averaged to obtain the PSF, which allowed us to quantitatively characterize our imaging approach. Finally, the PSF was filtered by applying an average filter and re-sampled with a resolution of 200 nm×200 nm×200 nm. The PSF was applied to deconvolve the image stacks.

Figure 10:
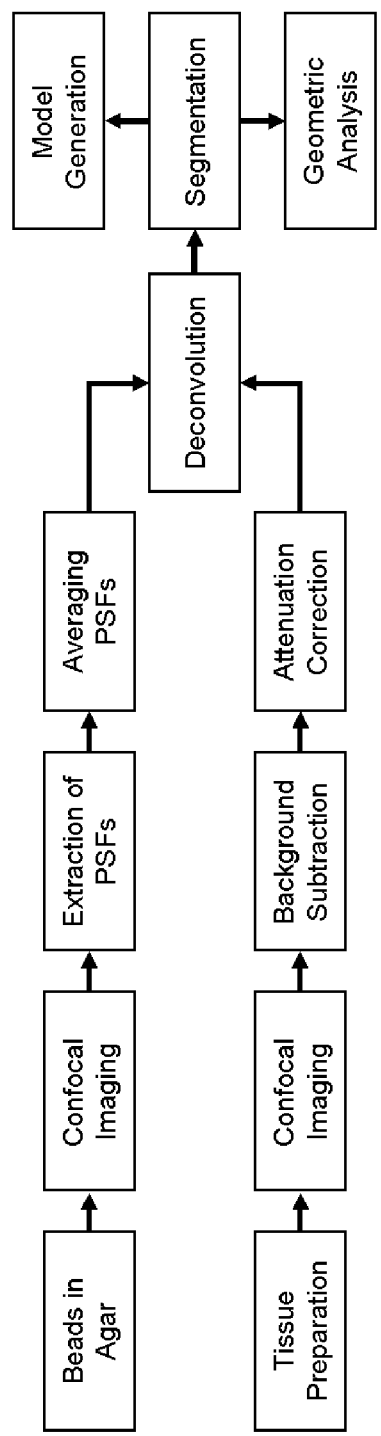

Signal-to-noise ratios in the raw images were estimated to characterize image stacks. Regions of 300 voxels were sampled inside myocytes to calculate variances of signal intensity and in the extracellular space to calculate mean signal intensity. The signal-to-noise ratio was calculated from the mean signal intensity divided by the variance. Raw image stacks were processed using a combination of C++ and MatLab software (MathWorks, Natick, Mass.) to remove background signals and correct for depth-dependent attenuation (FIG. 10). The background signal was estimated by averaging signals in small regions where the expected intensity is zero (i.e. inside myocytes). Depth-dependent attenuation of signal intensity was calculated by selecting lines in the Z-axis (laser beam) direction with the smallest standard deviation of the associated intensity. Intensities along these lines were fit to an exponential function using least square optimization to obtain a slice-wise scaling factor as a function of depth.

Figure 14:
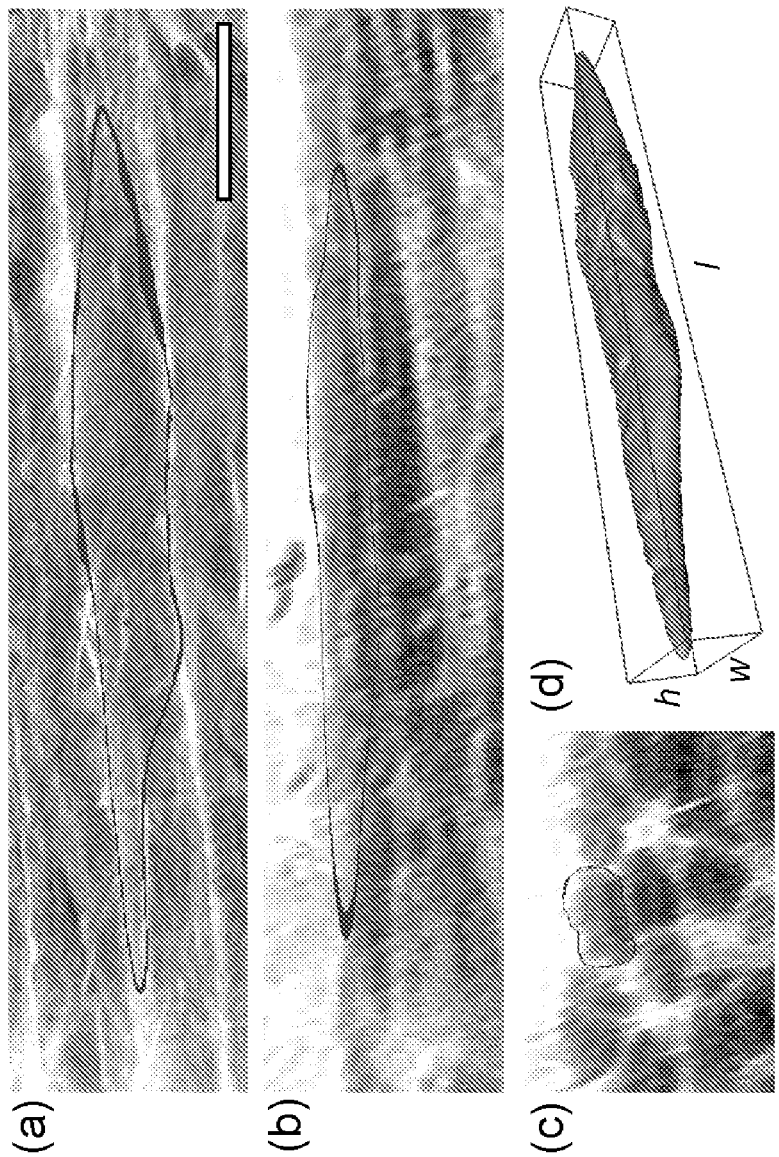

Myocytes were segmented by manually deforming a surface mesh followed by iterative thresholding. As shown in FIG. 14, an initially ellipsoid-shaped mesh comprised of 5120 triangles was wrapped around each myocyte in the field of interest. Histograms of voxel intensities were created for the volume enclosed by each mesh to calculate the mode and standard deviation of voxel intensities. The threshold values were chosen independently for each myocyte based on the calculated mode and standard deviation to distinguish between intra-myocyte and extracellular spaces.

After thresholding, geometric analysis was performed on the extracted whole myocytes. Principal component analysis (PCA) was used to determine the principal axis of each segmented myocyte. A bounding box was created around each myocyte based on the PCA as illustrated in FIG. 14(d). The bounding box dimensions in direction of the first, second and third principal axis were considered to be the myocyte length, width and height, respectively. Myocyte volume was calculated by counting the intra-myocyte voxels. Average cross-sectional area was determined by dividing cell volume by length. The volume fraction of tissue occupied by myocytes was determined by sampling random volumes of 300×300×30 voxels within regions of the image stack where all myocytes were segmented. Myocyte density was defined as mean of the myocyte volume fraction (MVF) divided by the volume of each cell (Vi):

$$\text{Myocyte Density} = \frac{1}{n}\sum \frac{MVF}{V_i}$$

Figure 4A:
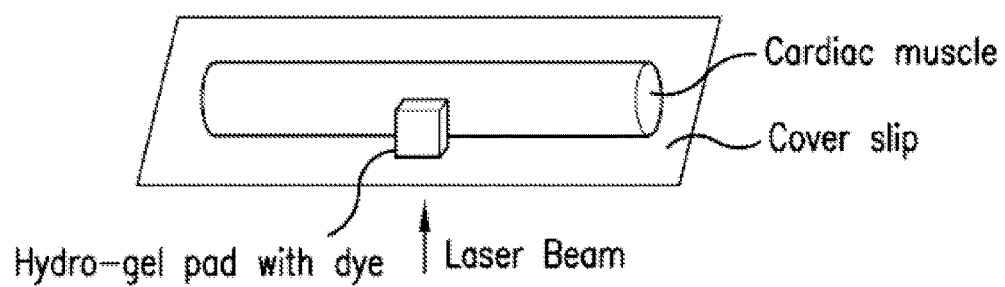
FIG. 4A shows a schematic view of an experimental setup up to study the dynamics of dye diffusion.
Figure 4B:
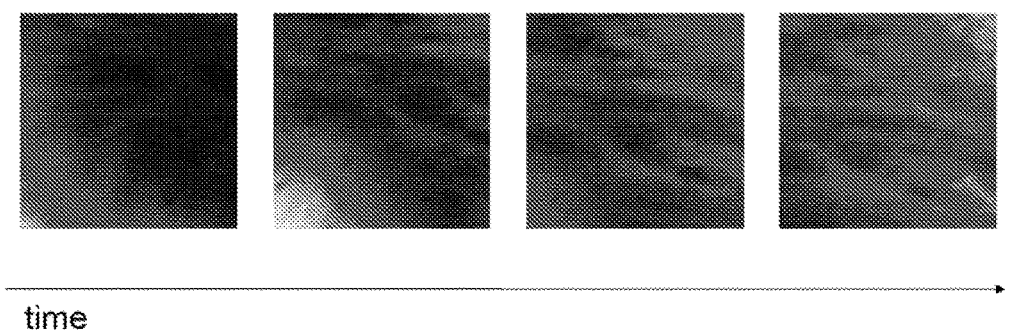
FIG. 4B shows the results from the diffusion study schematically shown in FIG. 4A. In the experimental study, the dye carrier (a hydrogel pad loaded with fluorescent dye Alexa 488 conjugated to dextran) was brought in contact with the surface of a rabbit papillary muscle. As shown in the time lapsed photographs, diffusion is capable of transporting dye from the carrier into the tissue region of interest. The resulting concentration of dye therein the region of interest is sufficient for fluorescence imaging.

For some imaging studies, excised hearts were mounted and perfused with the modified Tyrode's solution at 8 mL/min retrogradely through the aorta using the Langendorff method. Two-dimensional images with a field of view of 176.3×124.9 µm and a lateral resolution of 0.48 µm were acquired from the Langendorff preparation with a fiber-optics confocal system (FCM1000, Leica, Wetzlar, Germany) and a microprobe (M/30). The microprobe tip diameter was 4.2 mm and the working distance was 30 µm. A hydrogel dye carrier was configured as an agar sheath that fit over the micro-probe tip as shown in FIG. 4(a).

Figure 12:
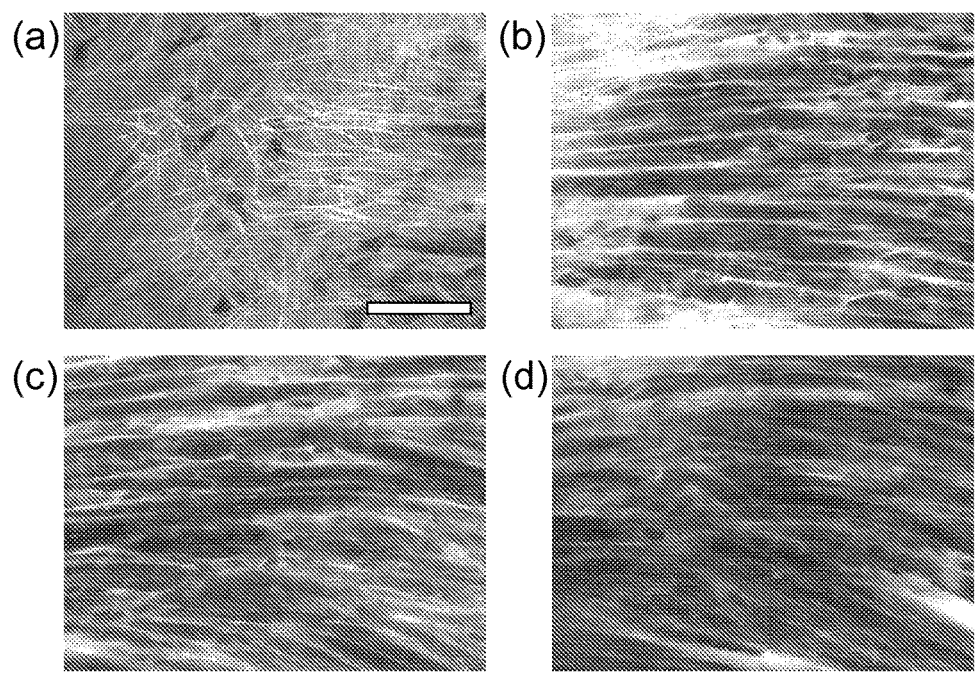
Figure 13:
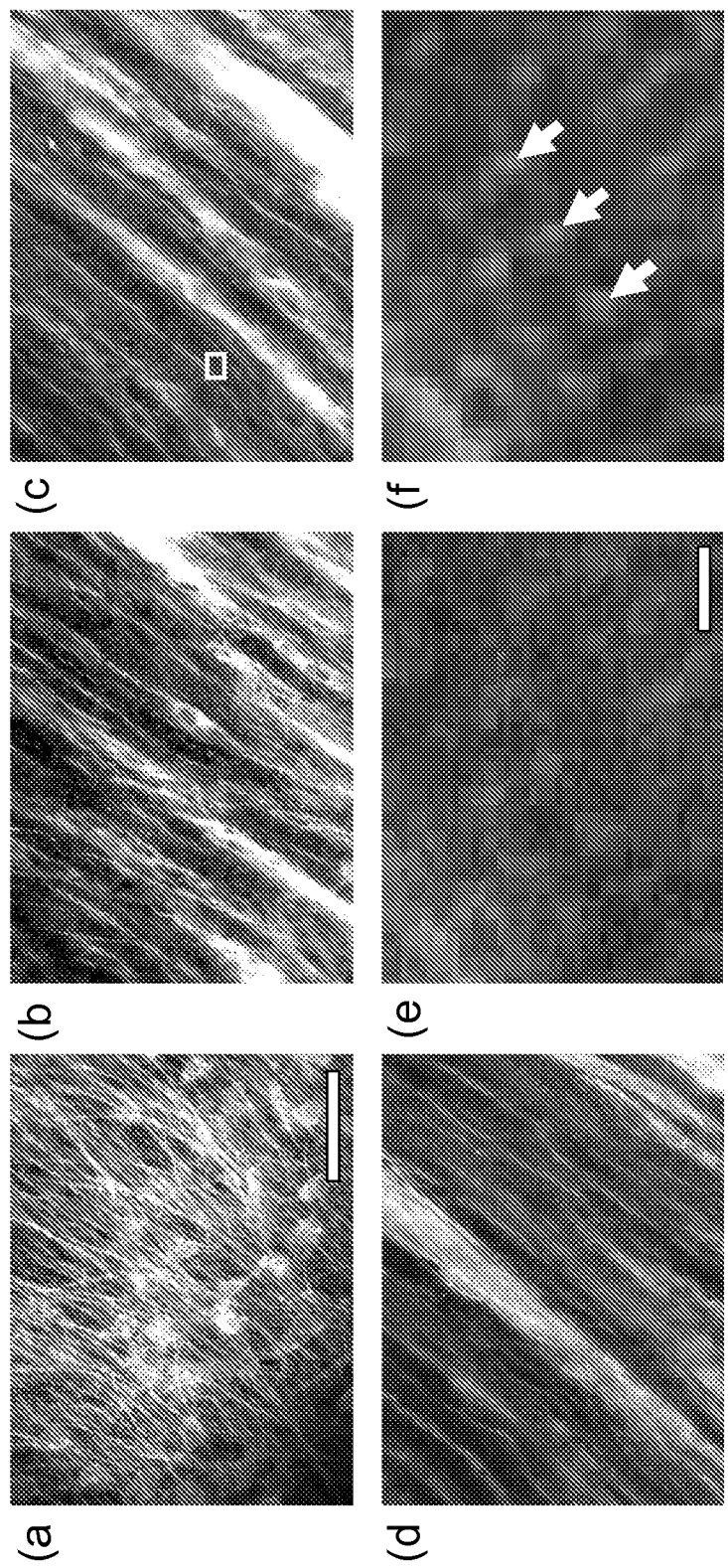

Upon pressing the tissue sections onto the hydrogel carrier, the dextran-conjugated Texas Red dye diffused rapidly through the endo- or epicardial layers and into the myocardium. The dye was immediately available insufficient concentration for confocal imaging of the cardiac microstructure. Exemplary two-dimensional images of atrial and ventricular tissue sections acquired with the BioRad confocal microscope are shown in FIGS. 12(a) and 13(d), respectively. These images originate from three-dimensional stacks covering approximately 1 µm outside of the tissue surface and up to 80 µm into the myocardium.

Fluorescence appeared to be associated with clefts between cells (interstitial space), collagen fibers, transverse tubules and capillary vessels; whereas darker regions appeared to be associated with cells. Image slices through the epicardial and endocardial network of thin collagen fibers in atrial and ventricular tissue are shown in FIGS. 12(a) and 13(a), respectively. The fibers are brighter than their surroundings and appear to be, to some degree, orientated parallel to the myocytes. The image through the ventricular endocardium (FIG. 13(a)) includes endothelial cells.

Figure 5:
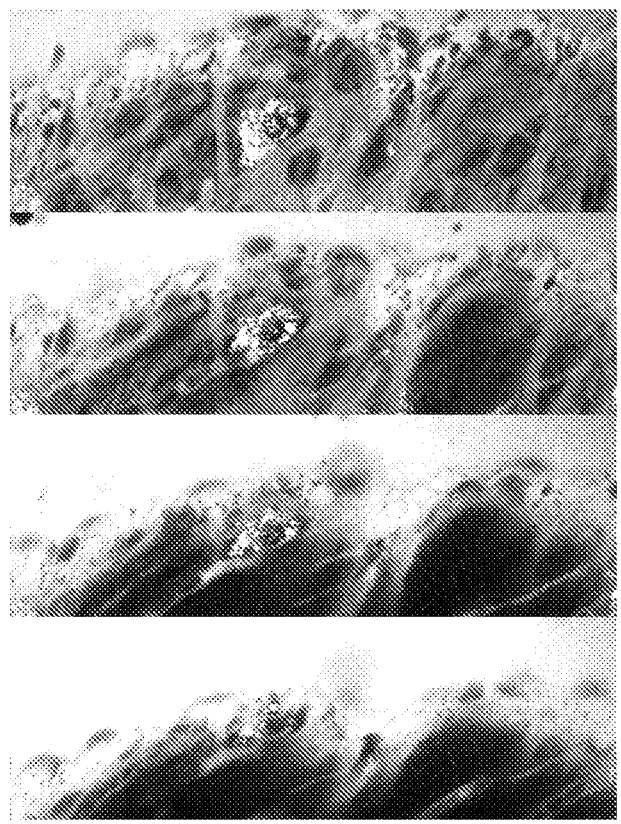
FIG. 5 displays a series of confocal microscopic images of tissue microstructure at different depths through a rabbit's left ventricular muscle. In this study, the dye (Alexa 488 conjugated to dextran) penetrated the epicardium and was diffused into the tissue region of interest.
Figure 6:
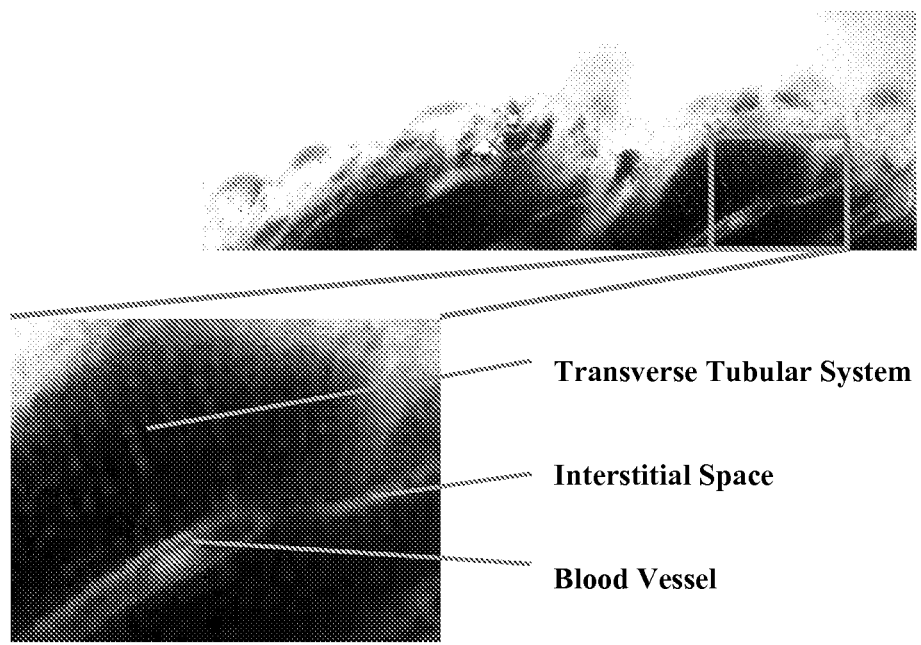
FIG. 6 shows an enlarged portion of a confocal microscopic image from the rabbit's left ventricular muscle. The exemplary images allow for the identification of ventricular myocytes and their transverse tubular system, the interstitial space, and blood vessels.
Figure 7:
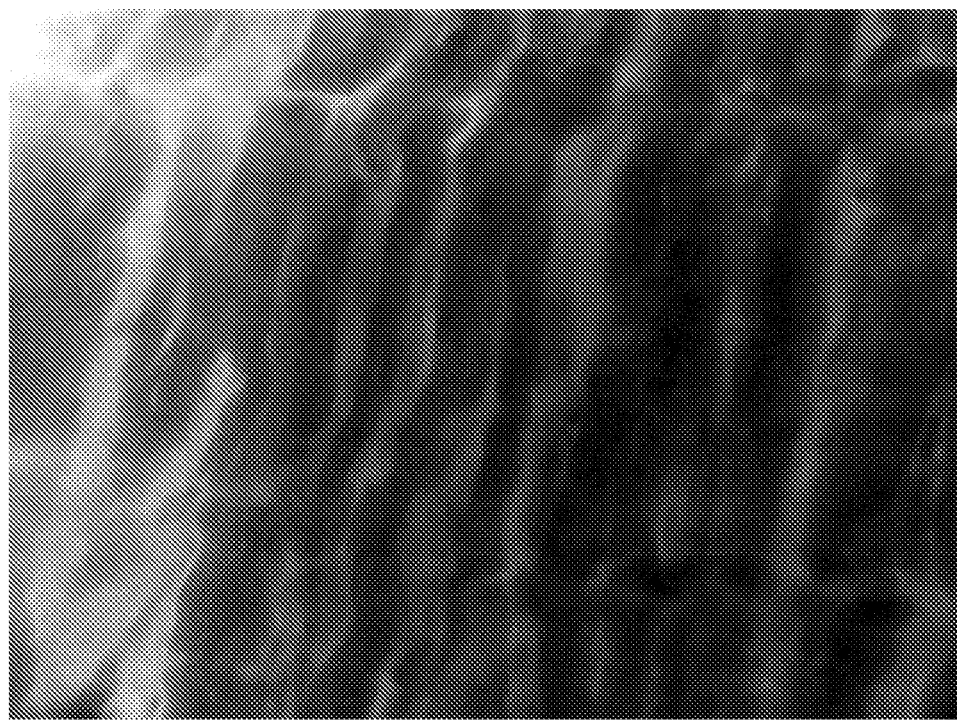
FIG. 7 shows an exemplary confocal microscopic image of tissue microstructure of a rabbit papillary muscle. The image is from a stack of 100 images and shows a dense arrangement of myocytes.

Image slices into atrial and ventricular myocardium are presented in FIGS. 12(b)-(d) and FIGS. 13(b)-(d), respectively. These image slices are from depths of 10, 20 and 30 µm into the myocardium with respect to the epicardial or endocardial surface layer (FIGS. 5(a) and 6(a)). The density of the network of collagen fibers appeared to be larger in the endo- and epicardium than within the myocardium. Furthermore, images extending further into the myocardium exhibited less overall fluorescence.

Optical properties of the BioRad confocal microscopy system were characterized by measurement of PSFs as described above. The PSF exhibited full widths at half maximum of 0.30 µm in the XY plane (transverse to the laser beam) and 1.85 µm in the Z direction (parallel to the laser beam).

Figure 11:
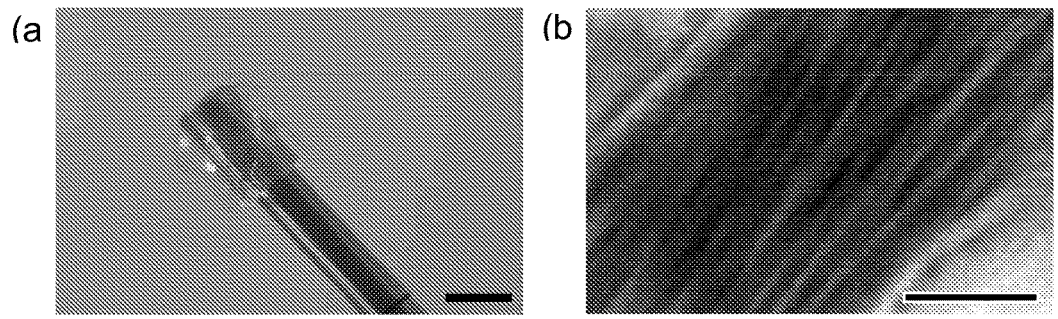

In another experiment, images were also acquired with a fiber-optics confocal microscope (FCM1000, Leica, Wetzlar, Germany). The dye carrier was attached to the microprobe tip and gently pressed on the epicardial surface of the atria and ventricles of a Langendorff-perfused heart. An exemplary two-dimensional image of atrial tissue is shown in FIG. 11(b). The dye was readily available for imaging. High and low fluorescence intensities were associated with the extra- and intracellular spaces, respectively.

Methods of digital image processing and analysis were applied to quantitatively describe and model cardiac tissue microstructure from three-dimensional image data. For this purpose, 19 image stacks were acquired from a total of 9 rabbits for subsequent analysis. Fourteen of these stacks were rejected from analysis due to low signal-to-noise ratios, discontinuities within the image stack by motion and/or poor tissue quality. Signal-to-noise ratios below 3 were considered low. Background signals were removed, corrected for depth-dependent attenuation, and deconvolved the image stacks. FIGS. 13(e) and (f) illustrate the effect of this processing on the image stacks. Processed image stacks exhibit fine details of myocytes such as the transverse tubular system (FIG. 13(f)), which were difficult to identify in the unprocessed image data (FIG. 13(e)).

Individual myocytes were segmented from three dimensional image stacks (FIG. 14), which allowed for subsequent spatial modeling (FIGS. 15 and 16) and quantitative analysis of myocytes (Tables I and II). Segmentation was performed on 50 atrial myocytes and 36 ventricular myocytes. Quantitative analysis was only performed on whole myocytes, which included 28 atrial myocytes and 20 ventricular myocytes.

Figure 15A:
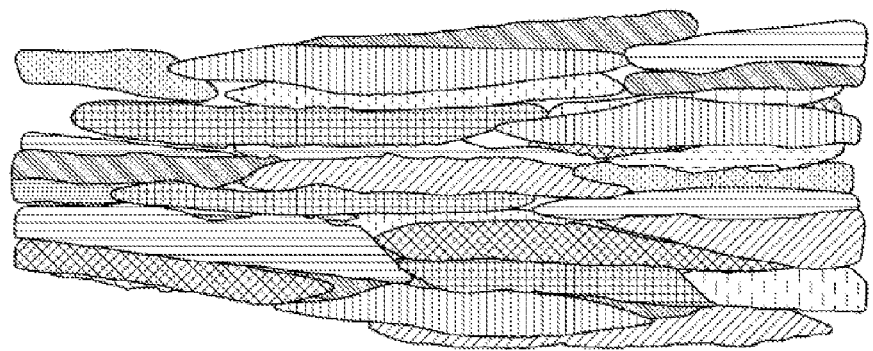
Figure 15B:
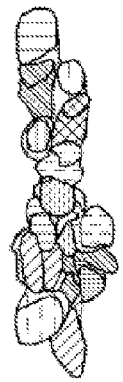
Figure 15C:
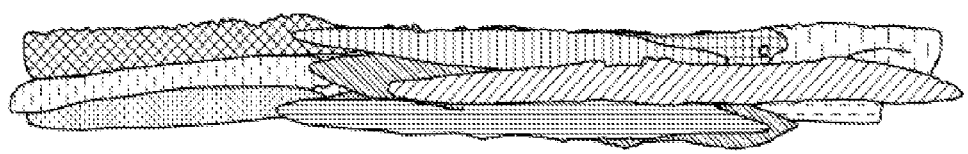
Figure 15D:
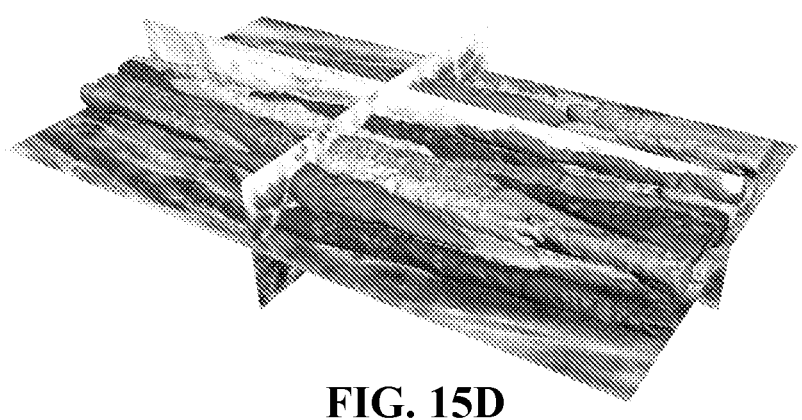
Figure 16:
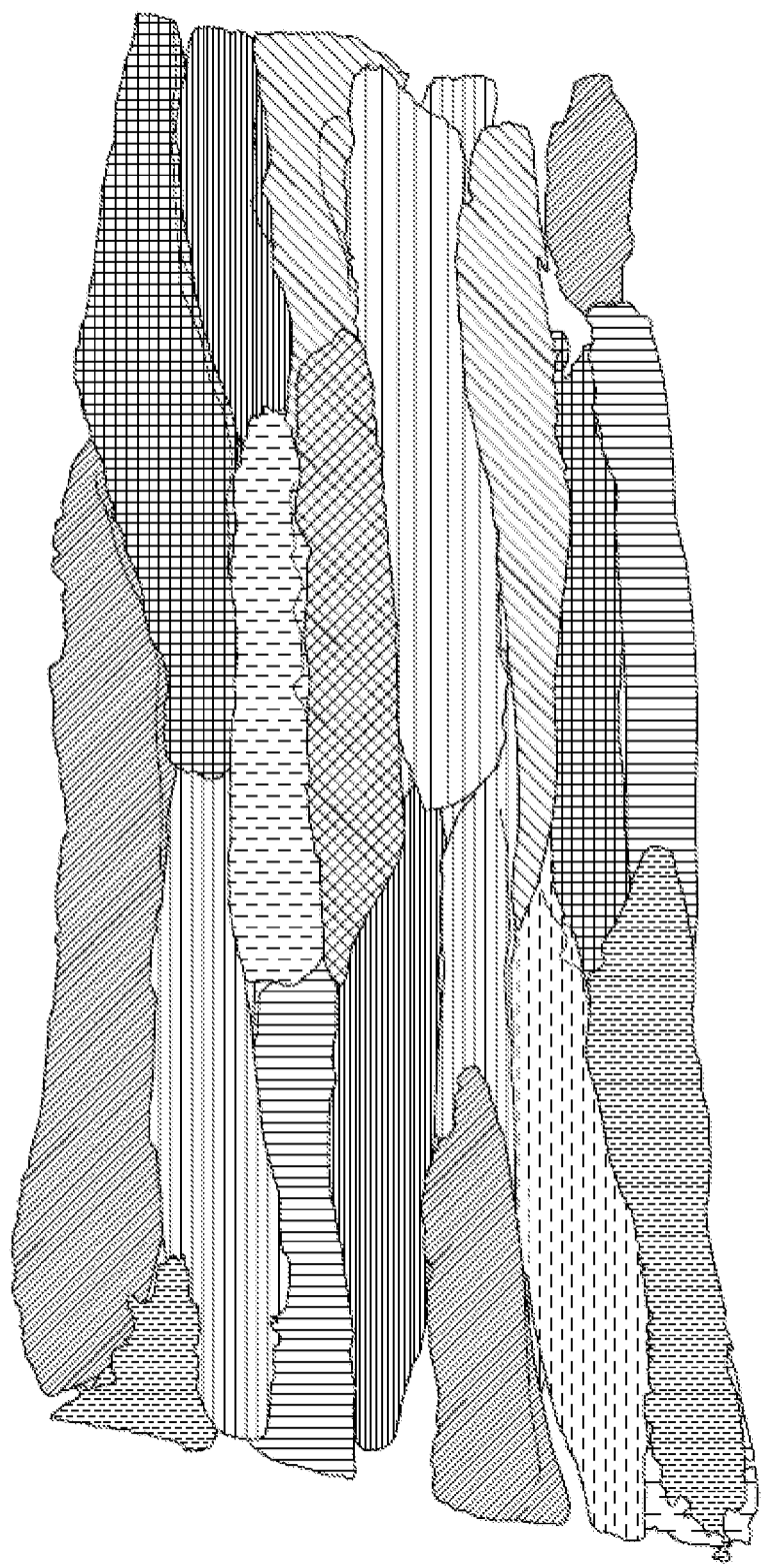

An exemplary segmentation of a single myocyte from a three-dimensional stack of atrial tissue is shown in FIG. 14. The manually deformed surface mesh is illustrated in three orthogonal planes in FIGS. 14(a)-(c). Threshold values to distinguish between intra-myocyte and extracellular space were chosen to be the mode plus 2 standard deviations of signal intensity for each segmented myocyte. FIG. 14(d) shows the segmented myocyte after thresholding and in a bounding box aligned to the principal axes of the myocyte. The dimensions of the bounding box determined the length, width and height of the myocyte. Three-dimensional spatial models of segmented myocytes from three-dimensional stacks of atrial and ventricular tissue are shown in FIGS. 15(a) and 16, respectively. FIG. 15(d) shows a three-dimensional visualization of the atrial model overlaid with orthogonal confocal images.

Quantitative analysis revealed mean and standard deviation (mean±sd) of lengths, widths and heights of atrial myocytes to be 105.0±10.6, 13.1±1.7 and 9.7±1.6 µm, respectively, and ventricular myocytes to be 112.3±14.3, 18.4±2.3 and 14.1±2.7 µm, respectively. Average volumes of atrial and ventricular myocytes were 4901±1713 and 10,299±3598 µm$^3$, respectively. Furthermore, the myocyte volume fractions for atrial and ventricular tissue were 72.4±4.7% and 79.7±2.9%, respectively. Myocyte density was 165,571±55,836 and 86,957±32,280 cells/mm$^3$ for atrial and ventricular tissue, respectively. Principal component analysis demonstrated that the long (first principal) axis of myocytes was parallel to the surface of atrial and ventricular tissue (FIGS. 15 and 16) within 6° and 3° deviation to the surface plane, respectively.

Furthermore, the majority of ventricular myocytes (70%) had their second principal axis approximately parallel)(<25° to the tissue surface. In contrast, atrial tissue did not show parallel orientation of the second principal axis with respect to the surface.

Example Two

Figure 17:
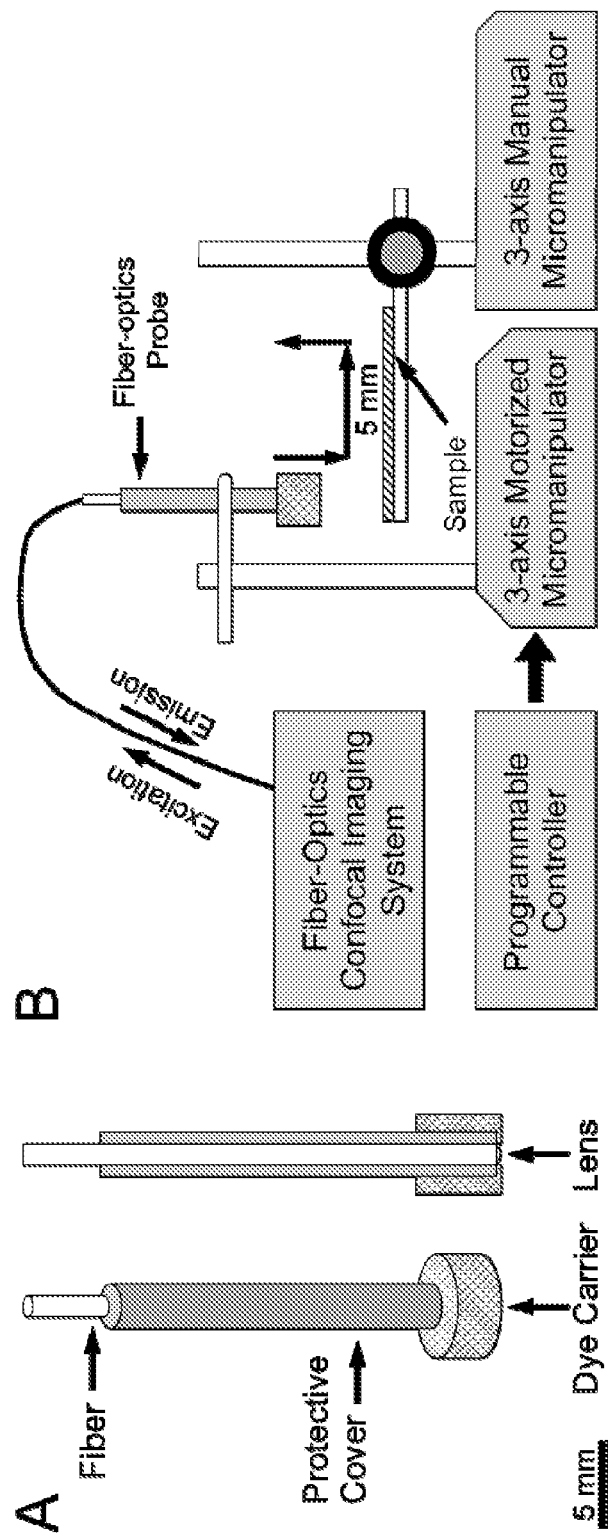
FIG. 17 depicts: (A) an exemplary dye carrier attached to an imaging microprobe and (B) an exemplary automated setup for running a line scan test to evaluate dye release.
Figure 20:
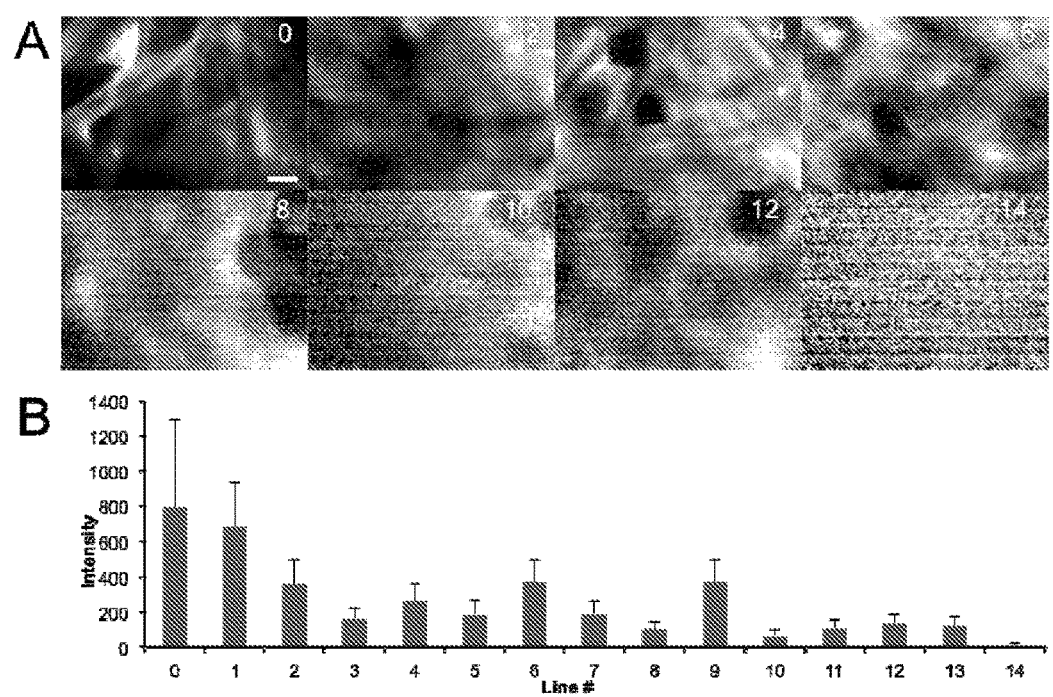
Figures 21, 22:
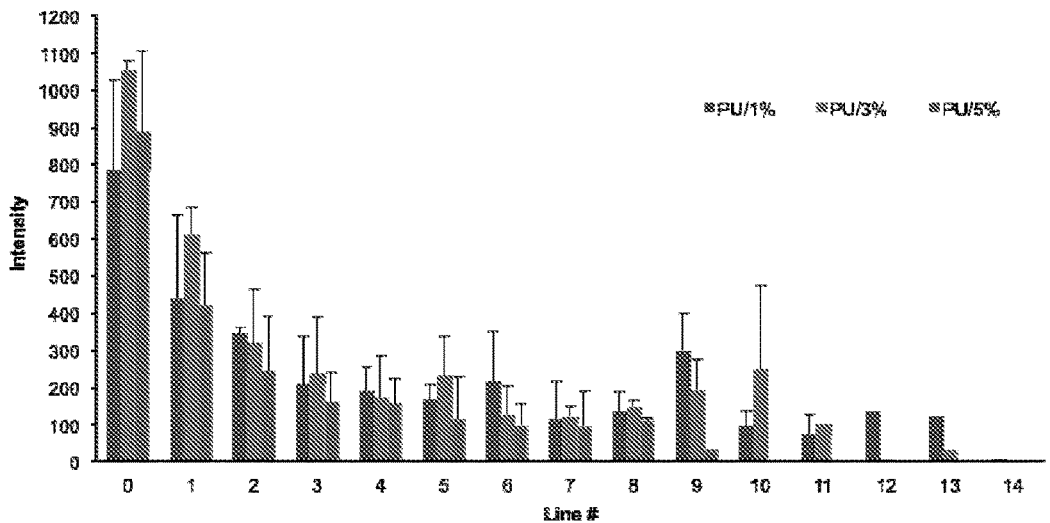
FIG. 22 displays exemplary dye carrier load and release characteristics for different materials and hybrids. Initial intensity and decay rates were determined from data presented in FIG. 21.

An exemplary setup for evaluating dye release in dye carriers of different materials and of hybrid materials is shown in FIG. 17. Dye carriers were loaded with fluorescent dyes and fixed to an imaging probe as described herein. A motorized micromanipulator was used to move the loaded dye carrier and probe to the surface of a tissue sample whereby the dye carrier and probe were moved along the tissue surface in one direction for a length of 5 mm. This line scan test was performed subsequently over several clean tissue samples using the same loaded dye carrier. Image recordings were taken for each line drawn to determine the dye release characteristics of each tested dye carrier over several lines (FIGS. 20 and 21). As shown in FIG. 21, release properties were similar for each concentration. An advantage of the PU/1% dye carrier versus the PU/3% and PU/5% carrier was that it caused commonly higher intensities in the second half of line scanning (line#8-14).

Figure 18:
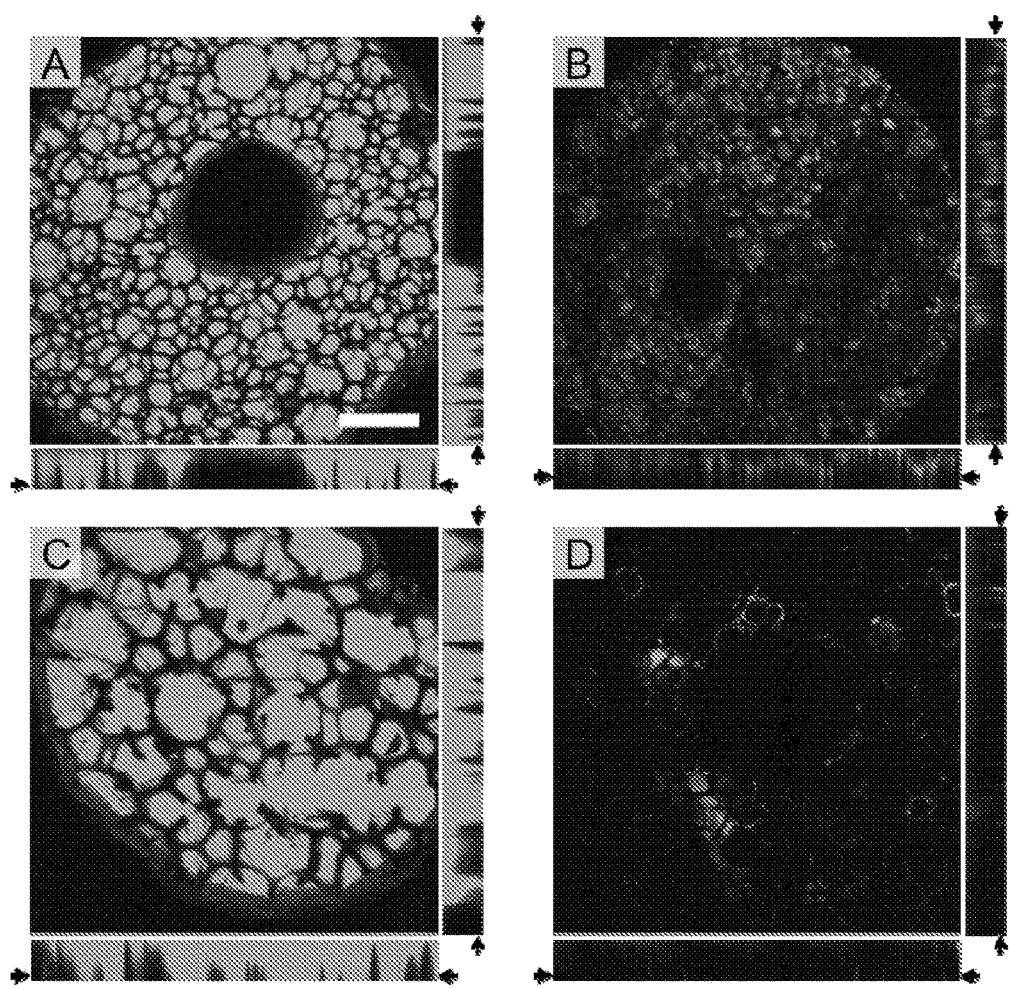
FIG. 18 displays cross-sectional views through image stacks acquired with confocal microscopy of exemplary dye carriers formed of different materials. The height of the image stacks is 0.5 mm. Evaluated materials include (A,D) polyurethane (PU), (B) high-density PU and (C) polyester foam. As shown in these Figures, different carrier materials have different characteristics that can allow a designer to optimize delivery profiles depending on desired carrier properties and release rates. Scale: 1 mm FIG. 19 displays cross-sectional views through image stacks acquired with confocal microscopy of an exemplary hybrid dye carrier before and after line scan test. A PU carrier loaded with 1% agar solution and dye (A) shows similar load characteristics as the PU foam alone (B). Dye is only partially released after scanning 11 lines of 5 mm length. Scale: 1 mm FIG. 20 displays: (A) image recordings of a test sample that were collected using an exemplary fiber-optics confocal microscope and a dye loaded PU/1% agar carrier during a line scan test at 12 frames per second (Example images of line 0-14 show a decreasing signal-to-noise ratio); and (B) mean and standard deviation of signal intensity that were calculated for each image frame and the mean and standard deviation intensity across all frames for each line. Scale: 20 μm FIG. 21 displays a statistical analysis of dye release from hybrid dye carrier with agar concentrations of 1, 3 and 5%. Mean and standard deviation of signal intensity were calculated from each image frame, averaged for each of these lines and averaged over 3 samples for each concentration.
Figure 19:
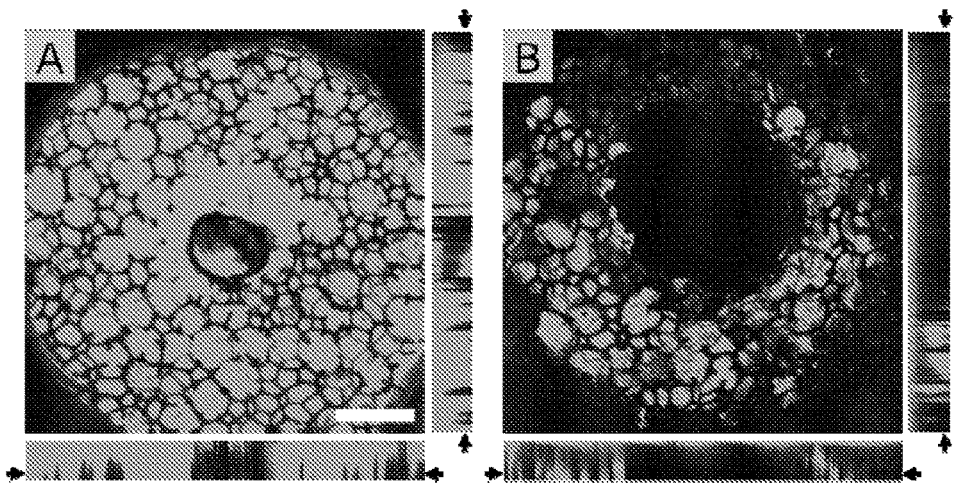

Different dye carriers were loaded with fluorescent dye for 15 minutes. Three-dimensional (3D) image stacks were taken of the carriers with a conventional confocal microscope before and after line scan tests at a spatial resolution of 20×20×20 μm with a 3.5× objective lens as shown in FIGS. 18 and 19.

Different dye carriers were weighed before and after dye was loaded for 15 minutes. The amount of dye absorption was thus calculated as shown in FIG. 22. Line scan tests were then performed whereby the maximum number of lines, initial intensity, and decay rates were determined for the different dye carriers.

Example Three

Figure 23:
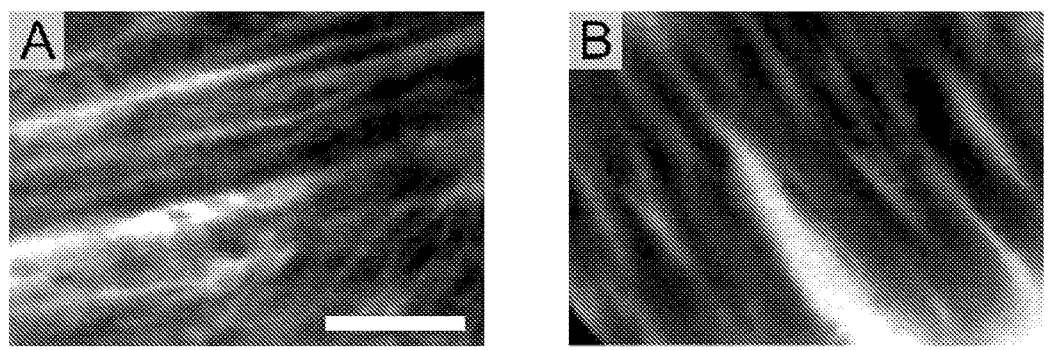
FIG. 23 displays image recordings collected using an exemplary fiber-optics confocal microscope and PU/1% agar dye carrier from living rat atrial (A) and ventricular sub-epicardial myocardium. Scale: 50 μm FIGS. 24A-24D display exemplary outer casings for a dye carrier and complementary probes as described herein.

In one example, hearts (n=4) were excised from adult male Sprague-Dawley rats (250 to 350 g) and Langendorff perfused with Tyrodes solution. A PU/1% agar hybrid dye carrier was evaluated with a fiber-optics confocal microscope using a manual micromanipulator on the surface of the rat hearts. Image recordings were taken of living atrial and ventricular sub-epicardial myocardium using this setup and exemplary images are shown in FIG. 23.

Example Four

Establishing hallmarks of the native myocardium in engineered tissue is essential for creating functional tissue that can serve as a surrogate for in-vitro testing or the eventual replacement of diseased or injured myocardium. Quantitative measures of structural and functional tissue characteristics form a technical cornerstone for the development and testing of engineered cardiac tissue. Native tissue is complex and exhibits a three-dimensional (3D) multi-cellular structure and function. This 3D microenvironment has profound effects on the properties, behaviour, and functions of resident cells. Furthermore, native tissue exhibits astonishing variation in the quantity, density, and morphology of cardiac cells during development, amongst species, between tissue types and in disease. Most engineered cardiac tissue aims to replicate left ventricular myocardium, which is heterogeneous and comprised of densely packed myocytes, fibroblasts and other cell types.

Fibroblasts account for the majority of cells in the heart and play important roles in normal cardiac function and disease. Although myocytes only account for 20-40% of cells that make up cardiac tissue, they occupy approximately 80-90% of the tissue volume and are the contractile cells solely responsible for pump function. Alterations in myocyte geometry and structure are known to occur during development and in disease states.

Myocyte structures that are critical for cardiac function include sarcomeres and gap junctions. Sarcomeres, the fundamental unit of contraction, occupy a large fraction of the intracellular volume and are highly aligned in healthy myocytes. Gap junctions allow for rapid electrical signaling between myocytes necessary for synchronous cardiac contraction. Connexin-43 (Cx43), the predominant isoform of gap junction channels in ventricular myocytes, has a half-life of 2 hours. The continuous turnover allows Cx43 to redistribute along the cell surface in response to environmental conditions. The distribution of Cx43 is known to vary during development and in disease states. For example, in rat cardiac tissue, Cx43 redistributes in response to tissue maturity. In neonatal tissue Cx43 clusters are found to be distributed over the myocyte membrane. As the tissue matures, Cx43 slowly becomes organized and at approximately 90 days after birth concentrates at the cell ends (i.e. polarized).

Gap junctions also remodel due to disease. For example, as human cardiac hypertrophy progresses into heart failure Cx43 expression decreases and accumulates at the lateral sides of myocytes instead of the ends (i.e. lateralized). Gap junctions can be coerced to rearrange in-vitro. A recent study in 2D monolayers of neonatal rat myocytes indicated polarization of Cx43 localization by stretching. The functional importance and dynamic nature of Cx43 makes it a target for analysis, and these types of responses may indicate some level of control over engineered cardiac tissue.

Several approaches have been developed to produce 3D engineered cardiac tissue including seeding preformed scaffold materials with cells, entrapping cells in a 3D environment, stacking cell sheets, and decellularizing and recellularizing tissue. The application of electrical stimulation, mechanical stimulation, or perfusion has been shown to aid in the tissue development. To investigate the structure of these engineered tissues, most reported methods rely on qualitative interpretation of 2D images. A more comprehensive analysis of structure can be accomplished through 3D confocal microscopy. Confocal microscopy is based on fluorescent labeling and has the ability to control the depth of field (slice resolution of <1 μm), reject out-of-focus light and collect sequential optical sections from thick specimens. The application of 3D confocal imaging to quantitatively characterize structure has not been widely performed on engineered tissue.

Methods 3D confocal imaging and image analysis were used to characterize hallmarks of cardiac tissue, including myocyte geometry and spatial distribution of Cx43, in engineered cardiac tissue with and without the application of electrical stimulation.

All animal procedures were performed in accordance with an approved protocol by the University of Utah Institutional Animal Use and Care Committee.

Cell Isolation

Ventricular cardiac cells were harvested from 1-day old Sprague-Dawley rats (Charles River, Mass.) using a protocol and supplies from Worthington Biochemical (Lakewood, N.J.). Briefly, hearts were aseptically removed and collected in calcium- and magnesium-free Hank's balanced salt solution (HBSS). Atria were removed and the ventricles were finely minced and digested in 50 μg/mL trypsin at 4° C. overnight. Further digestion was performed the following day with collagenase (1500 units) in Leibovitz L-15 media. Cell suspensions were triturated, filtered, centrifuged and resuspended in culture medium. Culture medium was made following Hansen et. al. using DMEM F12 (Thermo Fisher Scientific, Waltham, Mass.), 10% equine serum (Thermo Fisher Scientific, Waltham, Mass.), 2% chick embryo extract (Gemini Bioproducts, West Sacramento, Calif.), 50 μg/mL human insulin (Sigma-Aldrich, St. Louis, Mo.), 2 mM L-glutamine (Thermo Fisher Scientific, Waltham, Mass.), 20 U/mL penicillin (MP Biomedicals, Solon, Ohio), 50 μg/mL streptomycin (MP Biomedicals, Solon, Ohio), 63 μg/mL tranexamic acid (Sigma-Aldrich, St. Louis, Mo.) and 33 μg/mL aprotinin (Sigma-Aldrich, St. Louis, Mo.).

Sample Preparation and Culture

Figure 37:
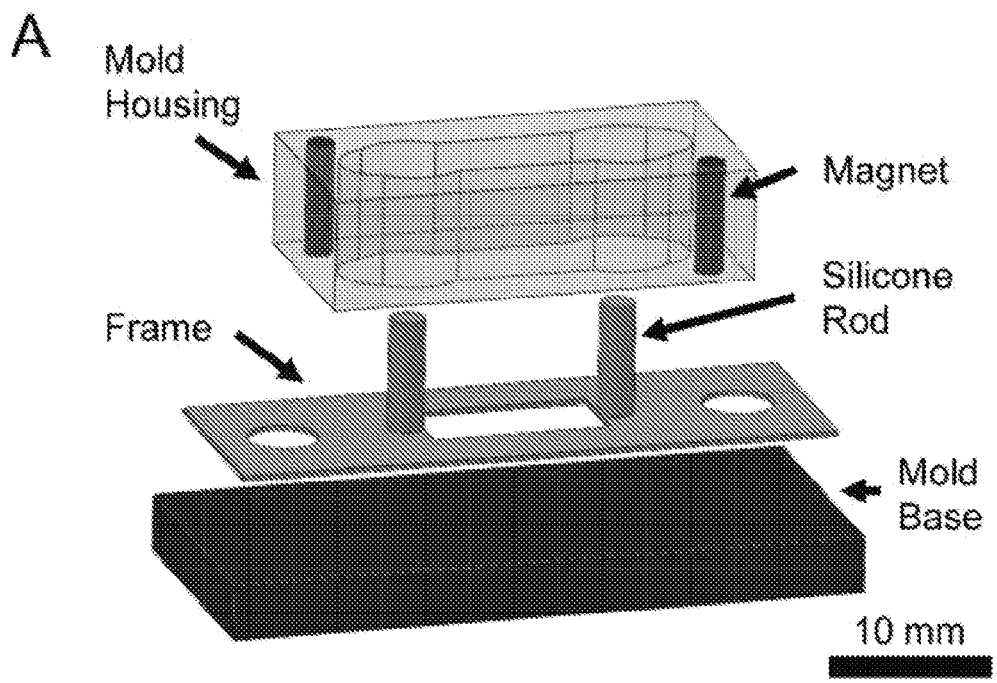
Figure 37:
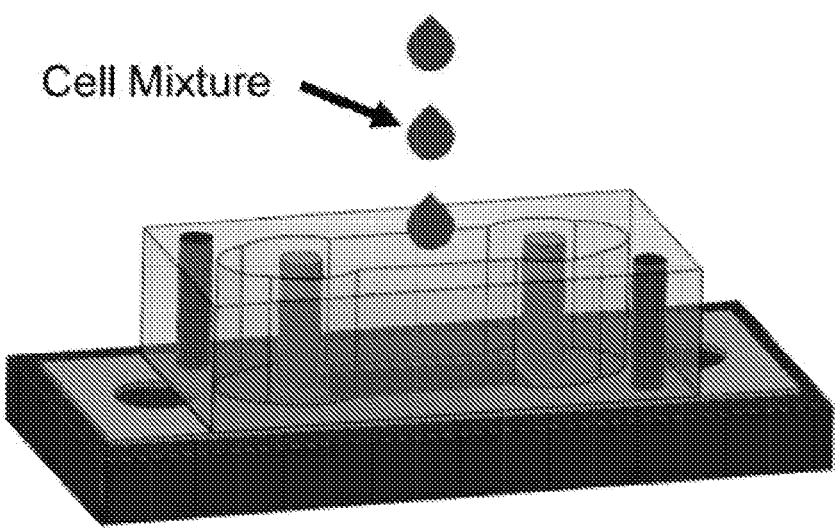

Fibrin-based engineered tissue samples were fabricated using methods described by Hansen et. al. Briefly, a reconstitution mixture was prepared on ice comprising of $4.1 \times 10^6$ cells/mL, 5 mg/mL bovine fibrinogen (Sigma-Aldrich, St. Louis, Mo.), and 100 μL/mL Matrigel (BD Biosciences, San Jose, Calif.). For each sample, 485 μL of reconstitution mixture was mixed with 15 μL thrombin (100 U/mL, Sigma-Aldrich, St. Louis, Mo.) and transferred to a custom mold (FIG. 37). The custom mold was contained in a Petri-dish and consisted of a Delrin® (McMaster-Carr, Los Angeles, Calif.) housing and base each containing two neodymium magnets (Applied Magnets, Plano, Tex.), which allowed for easy coupling and uncoupling of the mold and base. The housing had a center channel 4.8 mm in width and 20 mm in length with 6.35 mm holes centered with the silicone posts and contained cylinder-shaped (1.6 mm diameter×6.4 mm length) magnets. The base was 34×20 mm and contained disc-shaped (4.8 mm diameter×1.6 mm thick) magnets that aligned with the housing. Rectangular frames (34×12 mm) were cut from 0.30 mm thick polyester sheets (Mylar®, Fralock, Valencia, Calif.) using a cutting plotter (Graphtech FC7000, Irvine, Calif.) and AutoCAD (San Rafael, Calif.), and sandwiched between the housing and base. Frames had a rectangular center (10×4.8 mm) and two 4 mm through holes spaced 26 mm apart (center-to-center). Silicone rods (2 mm diameter×7 mm length) were fabricated from a platinum cured silicone elastomer (VST-50, Factor II, Lakeside, Ariz.) and attached to either side of the frame window (spaced 12 mm center-to-center). The silicone posts served to suspend the fibrin-based gel (FIG. 24D). Samples were allowed to polymerize at 37° C. for 90 min. After 30 min of polymerization, 500 μL of culture medium was added to keep the sample hydrated and aid in removal of the mold from the tissue sample. The frame was cut on both sides and the sample was elongated by 40% and secured with nylon screws into a custom bioreactor comprised of two Petri-dishes outfitted with carbon rods spaced 2 cm apart for electrical stimulation (FIG. 37C).

Engineered tissue samples were pre-cultured for 3 days before onset of electrical stimulation. Following pre-culture, samples were subjected to electrical field stimulation (2 ms symmetric biphasic square pulses, 4 V/cm, 1 Hz) for 9 days. Non-stimulated (NS) samples served as controls for stimulated (S) samples. Bright field images of central regions of the engineered tissue samples were obtained at days 3, 6, 9 and 12 of culture. The diameter was measured and the cross-sectional area was estimated assuming a cylindrical cross-section. The percent decrease in sample size was calculated normalized to the start of stimulation, i.e. day 3 of culture. At the end of culture samples were fixed with 4% paraformaldehyde and stored in PBS at 4° C.

ET and MCR

The excitation threshold (ET) and maximum capture rate (MCR) were measured at days 6, 9 and 12 of culture and for postnatal day 3 (P3) rat hearts following methods described previously. ET was defined as the minimum voltage required to elicit synchronous contractions over the entire sample and MCR as the maximum frequency for synchronous contractions at 150% of the ET. For engineered tissue samples, measurements were made following 30 min of media exchange. For P3 hearts, rats (n=4) were anesthetized with isoflurane inhalation. Following thoracotomy hearts were quickly excised and placed in a modified oxygenated Tyrode's solution (in mM: 126 NaCl, 11 Dextrose, 0.1 $CaCl_2$, 13.2 KCl, 1 $MgCl_2$, 12.9 NaOH, 24 HEPES) at room temperature. Strips of left ventricular myocardium (≈2×2×4 mm) were excised and placed in the same bioreactors used for tissue culture. For all samples, ET was measured by applying square 2 ms monophasic pulses starting at 0 V/cm and incrementally increasing until the sample was observed to beat synchronously. MCR was measured by setting the voltage to 150% of the ET and increasing the frequency until the contractions became asynchronous, irregular or ceased.

Native Tissue Preparation and Sectioning

P12 and adult rat hearts were used for comparison to the engineered tissue samples. Tissue was processed as previously described. Briefly, rats were anesthetized through methoxyflurane and hearts quickly removed. Hearts were perfused with a zero calcium Tyrode's solution for 5 min followed by 2% paraformaldehyde for 15 min for fixation using the retrograde Langendorff method. Whole hearts and engineered tissue samples were stored in 30% sucrose in preparation for sectioning. For adult hearts, biopsies were obtained with a 5 mm diameter biopsy punch through the left ventricular wall. P12 hearts were maintained as whole hearts. Biopsied adult hearts, whole P12 hearts and engineered tissue samples were frozen in tissue freezing medium (Triangle Biomedical Sciences, Durham, N.C.) and sectioned using a cryostat (Leica CM1950, Wetzlar, Germany). Adult heart biopsies were sectioned parallel to the epicardial surface and P12 hearts from the top of the ventricles to approximately 2 mm from the apex to produce 80-100 μm thick sections. Longitudinal and transverse cross-sections with a thickness of 100 μm were produced for engineered tissue samples.

Fluorescent Labeling

Fluorescent labeling was performed before sectioning for engineered tissue and after sectioning for native tissue samples. All labeling was performed on a laboratory platform rocker at room temperature (Thermo Fisher Scientific, Waltham, Mass.). Antibodies were diluted in blocking solution consisting of 4% goat serum (Invitrogen, Carlsbad, Calif.) and 0.5% Triton X-100 (Fisher Scientific, Pittsburgh, Pa.) diluted in PBS. Rinsing was performed between all incubation steps and included three 15 minute rinses. For quad-labeling samples were incubated for 16 h with WGA-conjugated CF488 (20-40 μg/mL in PBS, 29022, Biotium, Hayward, Calif.), 16 h with mouse $IgG_1$ anti-α-sarcomeric actinin (1:100, ab9465, Abcam, Cambridge, Mass.) followed by 6 h with goat anti-mouse $IgG_1$-conjugated Alexa Fluor 633 (1:200, A21126, Invitrogen, Carlsbad, Calif.), 1 h with Image-iT® FX signal enhancer (Alexa Fluor 555 Goat Anti-Rabbit SFX Kit, A31630, Invitrogen, Carlsbad, Calif.) to block nonspecific antibody binding, 16 h with rabbit anti-GJA1 (1:100, SAB4300504, Sigma-Aldrich, St. Louis, Mo.) followed by 6 h with goat anti-rabbit IgG-conjugated Alexa Fluor 555 (1:200, A31630, Invitrogen, Carlsbad, Calif.), and 3 h with 4',6-Diamidino-2-phenylindole dihydrochloride (DAPI) (1:500, Sigma-Aldrich, St. Louis, Mo.). For tri-labeling samples were incubated for 16 h with mouse $IgG_1$ anti-α-sarcomeric actinin (1:100, ab9465, Abcam, Cambridge, Mass.) followed by 6 h with goat anti-mouse $IgG_1$-conjugated Alexa Fluor 633 (1:200, A21126, Invitrogen, Carlsbad, Calif.), 16 h with mouse monoclonal anti-vimentin-conjugated Cy3 (1:50, C9080, Sigma-Aldrich, St. Louis, Mo.) and 3 h with DAPI (1:500, Sigma-Aldrich, St. Louis, Mo.). Tissue samples were stored in PBS.

Confocal Imaging

Three-dimensional image stacks were acquired for samples labeled with WGA, α-sarcomeric actinin, Cx43 and DAPI on a Zeiss LSM 5 Duo confocal microscope (Carl Zeiss, Jena, Germany) using a 40× oil-immersion objective lens with a numerical aperture of 1.3. Sectioned tissue samples were placed on a glass slide and surrounded by 15-30 μL of Fluoromount-G™ Slide Mounting Medium (Electron Microscopy Sciences, Hatfield, Pa.). The tissue sample was covered with a coverslip (#0) and placed on the imaging stage. The x-axis of the image stack was aligned with the long-axis of the myocytes by visual inspection and adjustment of the scan direction. For engineered tissue samples, sections were briefly scanned using a 10× objective lens to locate dense regions of myocytes. Only regions with high cell density were imaged in this study.

Image stacks were acquired with a spatial resolution of 200×200×200 nm and a typical field of view of 1024×768× 200 voxels using a multitrack protocol for quasi-simultaneous imaging of fluorophores in each 2D image slice. Laser lines with a wavelength of 364, 488, 543 and 633 nm were alternately applied to excite their associated fluorophores and collected using long pass 385 nm, band pass 505-555 nm, long pass 560 nm and band pass 630-650 nm filters, respectively. The dwell time was typically 1.3-1.5 µs/pixel resulting in a total imaging time of approximately 1 h per image stack. Signal-to-noise ratio (SNR) of each image stack was measured as described previously.[6] Image stacks with a SNR below 3 were rejected. For whole sample examination of engineered tissue, 2D images were acquired using a 10× objective of central transverse and longitudinal tissue sections stained with α-sarcomeric actinin, vimentin and DAPI. Higher magnification (40×) 2D images were also acquired for engineered and native tissue samples stained with α-sarcomeric actinin, vimentin and DAPI.

Image Processing

Image stacks were processed to improve image quality as previously described. Briefly, image stacks were processed to remove background, correct for depth-dependent attenuation and deconvolved using the iterative Richardson-Lucy algorithm with measured point spread functions. Cross-reactivity was corrected in image protocols where a primary antibody reacted with two secondary antibodies. The cross-reactivity was characterized by colocalization of Cy3 and α-sarcomeric actinin associated signal and removed by subtraction of Cy3-associated intensities. Individual myocytes were segmented using a manual deformable triangle mesh fitted in three image planes (XY, XZ and YZ) using the WGA, α-sarcomeric actinin, Cx43 and DAPI image data. The manual segmentation was refined using the WGA image data. Principal component analysis was performed for each segmented myocyte to yield eigenvectors $e_1$, $e_2$ and $e_3$. A bounding box was created for each segmented myocyte using the coordinate system spanned by the eigenvectors. Length, width and height were determined from the dimensions of the bounding box. Myocyte volume was defined as the volume of voxels within the segmented myocyte and surface area was estimated from the surface area of the triangle mesh.

Cx43 Analysis

Figure 38:
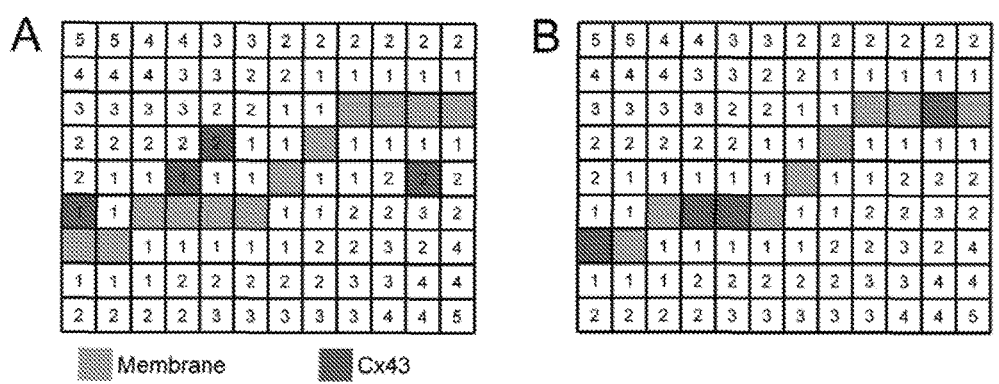

The percentage of the membrane stained positive with Cx43 was calculated for each segmented myocyte using projections of Cx43 intensities onto the myocyte surface. An illustration of this method is shown in FIG. 38. The membrane was approximated by surface voxels around the perimeter of the segmented myocyte. A 3D distance map was calculated from both the inside and outside of the membrane. Gradient vectors were calculated from the distance map. Cx43 intensities within 1 µm of the membrane were projected onto the membrane using the calculated distance map and vectors. The percentage of the membrane positive for Cx43 ($Mem_{Cx43Pos}$) was calculated for each myocyte:

$$Mem_{Cx43Pos} = \frac{nv_{Mem,Cx43>0}}{nv_{Mem}}$$

with the number of membrane voxels ($nv_{Mem}$) and the number of membrane voxels with non-zero Cx43 intensity ($nv_{Mem,Cx43>0}$).

The spatial distribution of Cx43 was characterized through projections of Cx43 intensities on the eigenvectors of the myocyte. Profiles were normalized with respect to total intensities and the range of arguments was transformed to [−1, 1] (i.e. centered with respect to the respective bounding box dimension). For each eigenvector, polarization ($Pol_{25\%}$) was characterized through summation of Cx43 intensities from 25% of either end of the myocyte. The minimal polarization ($Pol_{25\%\ min}$), maximum polarization ($Pol_{25\%\ max}$), and the sum of $Pol_{25\%\ min}$ and $Pol_{25\%\ max}$ ($Pol_{25\%\ total}$) were reported. Uniform Cx43 distributions for a profile would lead to $Pol_{25\%\ total}$ of 50%. Higher order statistical moments, skewness ($\gamma_1$) and kurtosis ($\gamma_2$), were calculated for the Cx43 intensity profiles. Skewness and kurtosis are measures of asymmetry and peakedness, respectively. A skewness of zero indicates that intensities are evenly distributed on both sides of the mean, whereas positive and negative values of skewness indicate that intensities are concentrated in the negative (x<0) and positive (x>0) domain, respectively. The kurtosis of a normal or uniform distribution is 0 and −1.2, respectively.

Myocyte Volume Fraction

The myocyte volume fraction (MVF) was calculated by down-sampling the processed 3D image data for the α-sarcomeric actinin labeling. Original voxels with dimensions of 0.2×0.2×0.2 µm were resampled to 1.6×1.6×1.6 µm using the maximum value in a 26-voxel neighborhood relation. This effectively "blurred" the sarcomeres and filled gaps between adjacent z-discs. Histograms of voxel intensities associated with actinin-positive regions were generated and thresholds were defined as mode intensity minus one standard deviation. Voxels above the threshold were considered actinin positive. MVF was defined as the sum of actinin positive voxels divided by the sum of all voxels within the image stack.

Statistical Analysis

Data were reported as mean±standard deviations. Statistical significance was determined with a one-way ANOVA for each measure, followed by post-hoc Tukey-Kramer tests with an α=0.05. Where appropriate, F-tests were performed to determine differences in variances with an α=0.05.

Results

Visual Inspection of Engineered Tissue Preparations

Figure 39:
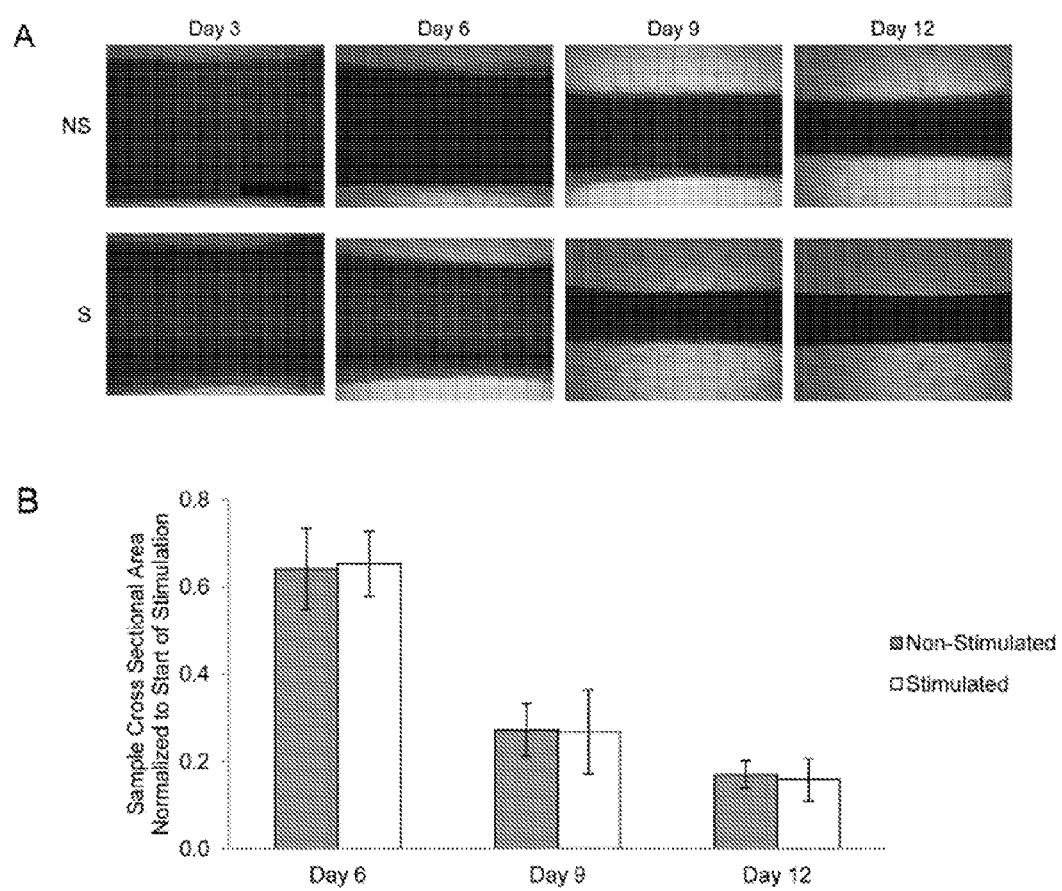
Figure 40:
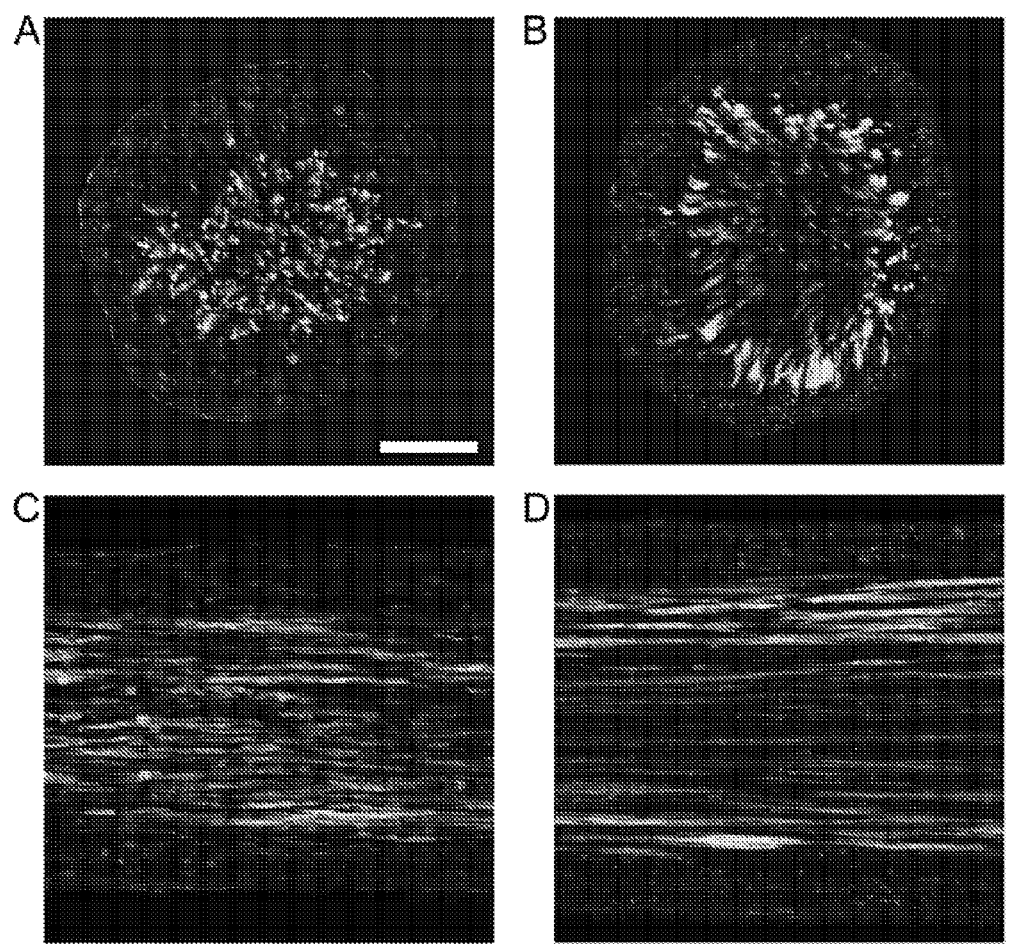
Figure 41:
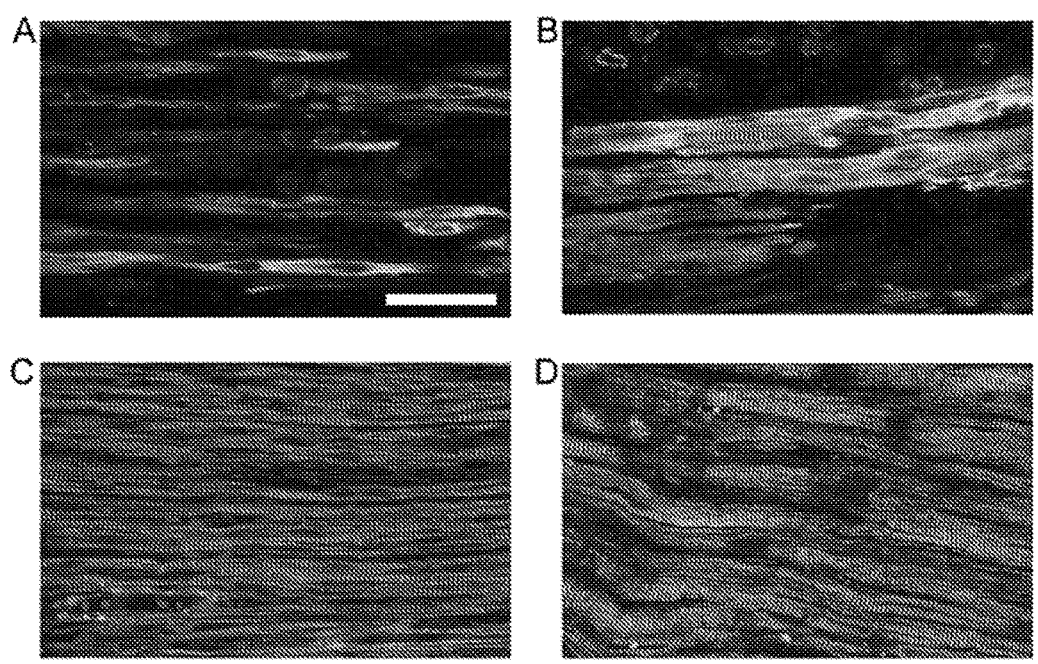

Bright field images of the engineered tissue samples showed that samples progressively condensed during culture (FIG. 39). Engineered tissue sample cross-sectional area estimated from the measured diameter was found to decrease to 17±3% and 16±5% for non-stimulated and stimulated samples at the end of culture from the onset of stimulation. No significant differences in cross-sectional area were observed between the non-stimulated and stimulated samples. Central transverse and longitudinal cross-sections of whole tissue samples exhibited dense regions of aligned myocytes and fibroblasts (FIG. 40). Although nuclei appeared to be homogeneously distributed through the sample thickness, elongated myocytes were located approximately 200 µm from the sample periphery. Higher magnification confocal images showed that fibroblasts were in close spatial proximity to myocytes, however, P12 and adult native tissue samples exhibited a higher density of fibroblasts and myocytes (FIG. 41).

Functional Analysis

Figure 28:
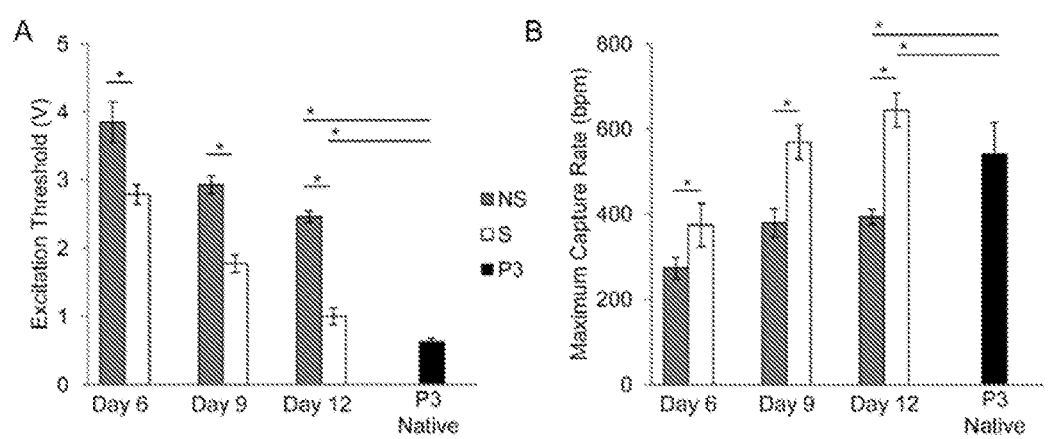
FIGS. 28-42 display the experimental results and setups used in various confocal imaging and analysis methods for quantitatively describing the structural features of cardiac tissues, as described herein.

ET and MCR were measured at days 6, 9 and 12 of culture and for isolated strips of P3 left ventricular myocardium. ET and MCR were not measurable at day 3 of culture as the samples did not respond to pacing. The ET decreased as a function of time in culture for both non-stimulated and stimulated samples, and the stimulated samples nearly approached the ET of P3 rat myocardium (FIG. 28). Stimulated samples had significantly lower ET at day 6 (2.79±0.15 vs. 3.85±0.29 V/cm), 9 (1.78±0.13 vs. 2.93±0.13 V/cm) and 12 (1.00±0.12 vs. 2.46±0.08 V/cm) of culture compared to non-stimulated samples (p<0.01). MCR increased as a function of time in culture for the stimulated group and exceeded that of P3 native myocardium by the end of culture (p<0.01). Non-stimulated samples exhibited an increase in MCR between days 6 and 9 (p<0.01), but not between days 9 and 12 (p>0.05). Furthermore, the stimulated samples had significantly higher MCR at days 6 (374±51 vs. 273±25 beats/min), 9 (569±40 vs. 379±33 beats/min) and 12 (645±39 vs. 393±18 beats/min) of culture compared to non-stimulated samples (p<0.01).

3D Confocal Imaging

Figure 42:
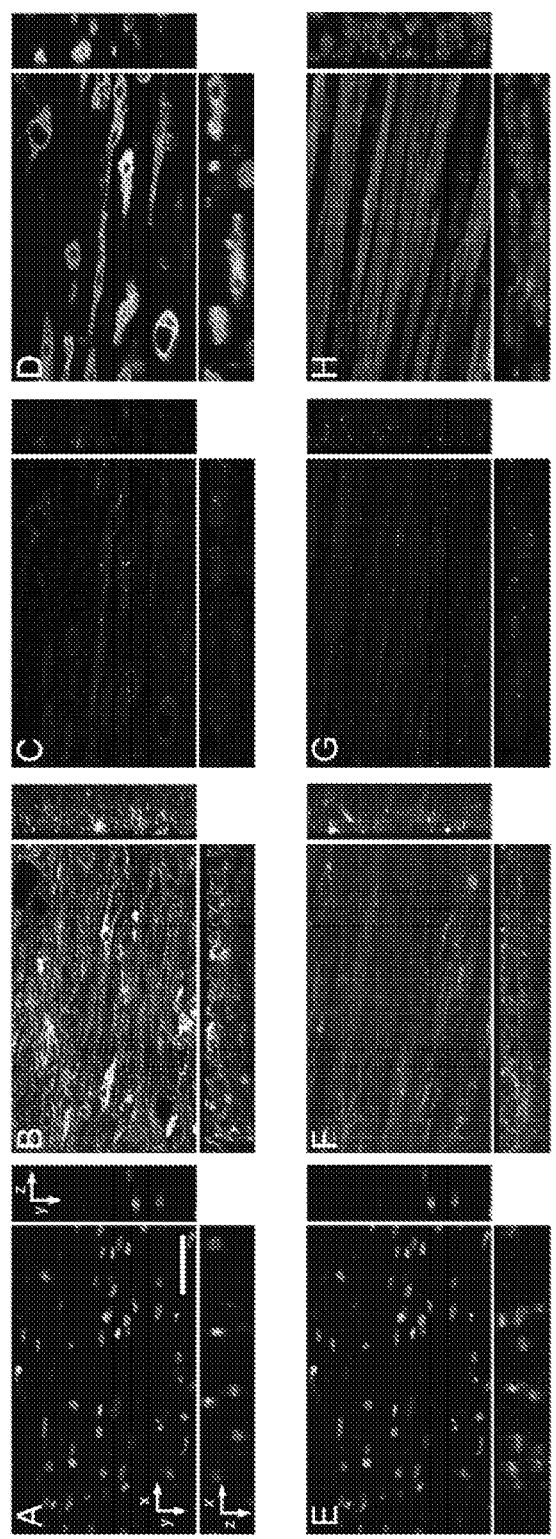

Three-dimensional confocal imaging and image analysis were applied to 9 non-stimulated and 12 electrically stimulated engineered tissue constructs and 5 P12 hearts and 7 adult hearts. The approach was applied to preparations stained with WGA, α-sarcomeric actinin, Cx43 and DAPI. Seventy-one image stacks from the 4 experimental groups were obtained. Image stacks with low SNR or motion artifact were removed for further analysis. Final data were obtained from 7 non-stimulated samples (n=11 image stacks), 7 stimulated samples (n=13 stacks), 5 P12 hearts (n=8 image stacks) and 7 adult hearts (n=13 image stacks). Raw image data for engineered tissue samples are presented in FIG. 42. These stacks originate from ~1 μm outside the tissue surface and extend ~50 μm into the tissue sample.

Figure 29:
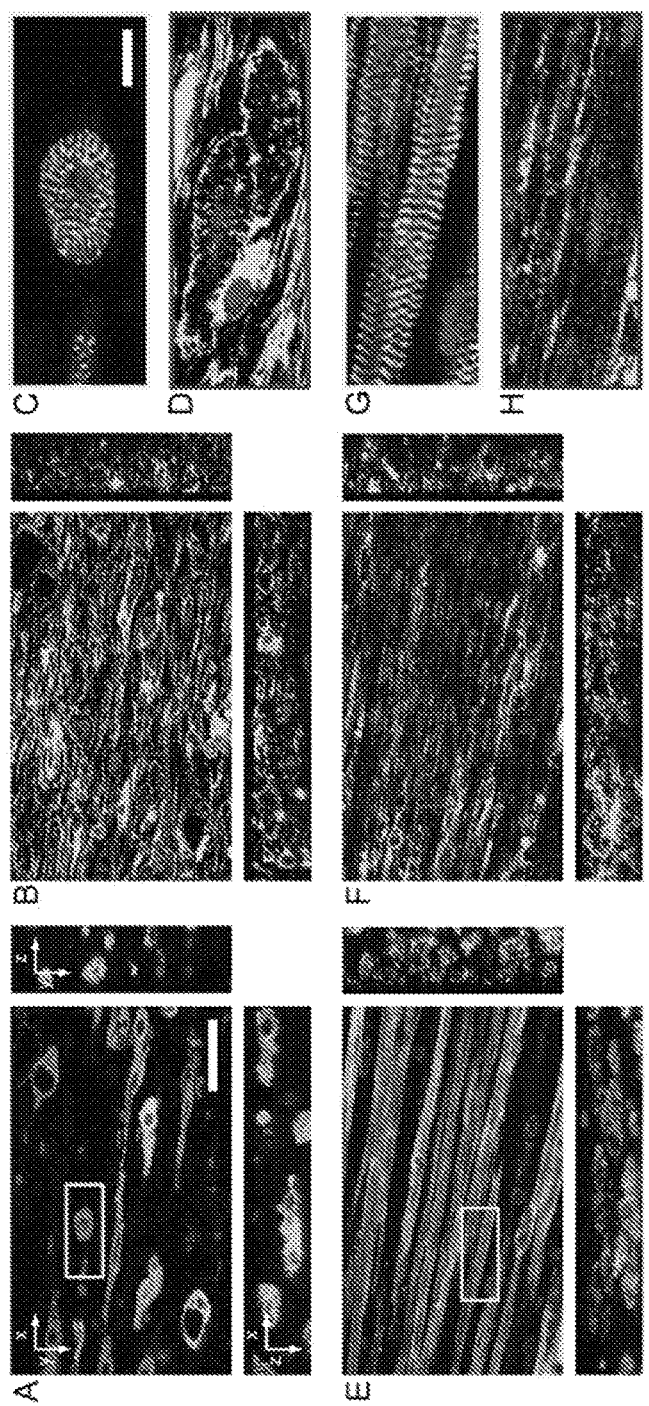
Figure 30:
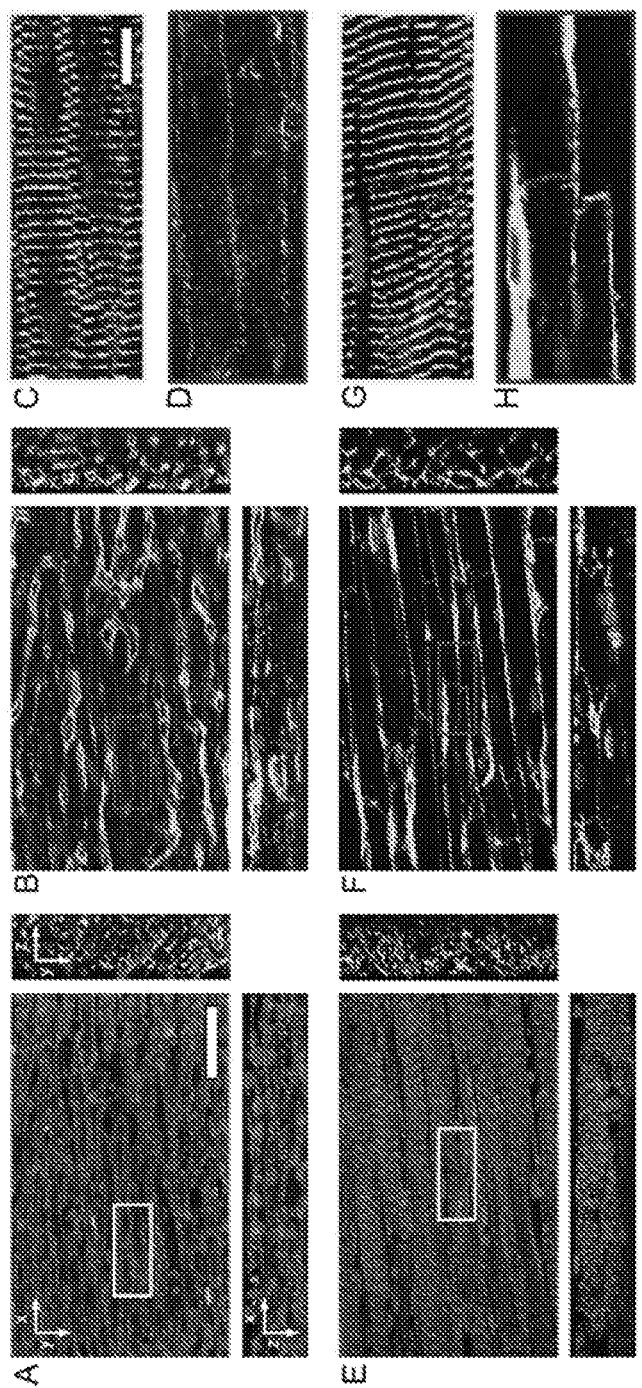

Processed image stacks from all groups confirmed that myocytes exhibited an elongated morphology (FIGS. 29 and 30). Marked differences between the non-stimulated and stimulated samples were visually noticeable in the 3D image stacks. The stimulated group exhibited more densely packed myocytes with a more pronounced elongated morphology (FIG. 29A, E), aligned sarcomeres in registry (FIG. 29C, G), and more Cx43 plaque formation on the myocyte membrane (FIG. 29D, H). Marked differences between P12 and adult tissue were also apparent by visual observation (FIG. 30). P12 myocytes appeared smaller in size (FIG. 30A, D) and had Cx43 plaque formation around the lateral sarcolemma (FIG. 30D), whereas adult myocytes had Cx43 plaque formation primarily at cell ends (FIG. 30H).

Myocyte Volume Fraction

Figure 31:
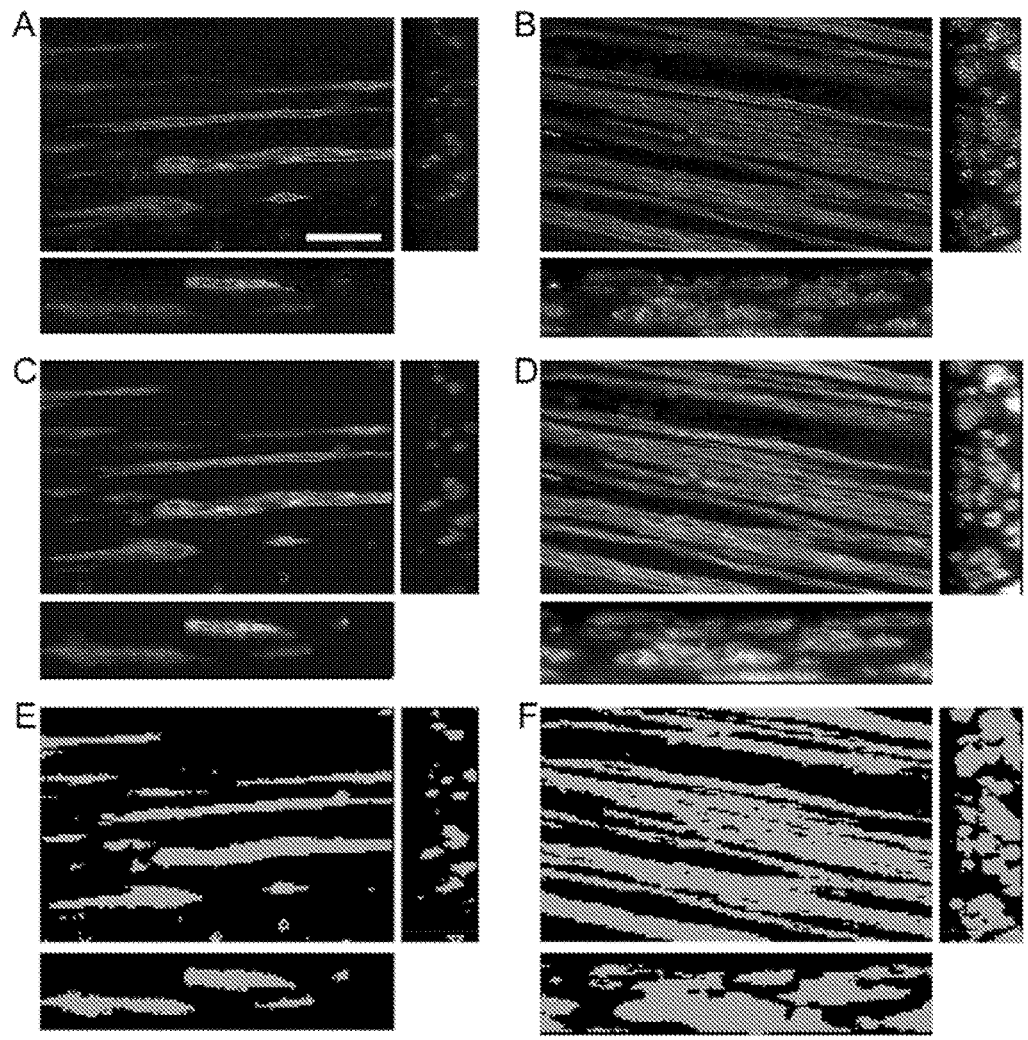

MVF was quantified by down-sampling the processed 3D image data for the α-sarcomeric actinin labeling (FIG. 31). Down-sampling of the original images (FIG. 31A-B) resulted in "blurring" of the actinin-associated intensities (FIG. 31C-D). Thresholding of the down-sampled images resulted in identification of the intracellular space of myocytes (FIG. 31E-F). The MVF was nearly double for the stimulated engineered tissue compared to non-stimulated (0.34±0.14 vs. 0.18±0.06, p<0.01). However, the MVF for both non-stimulated (0.18±0.06) and stimulated (0.34±0.14) engineered tissue was significantly lower than that of P12 (0.90±0.06) and adult (0.91±0.04) myocardium (p<0.01).

Myocyte Segmentation and Cx43 Analysis

Figure 32:
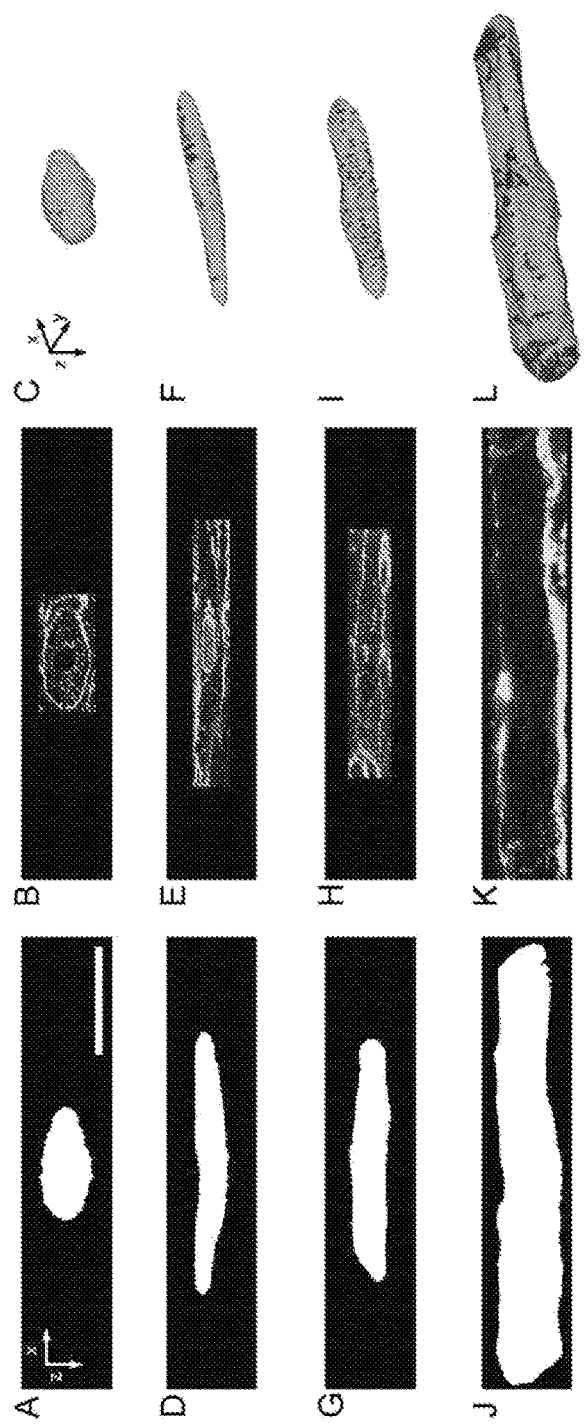
Figure 33B:
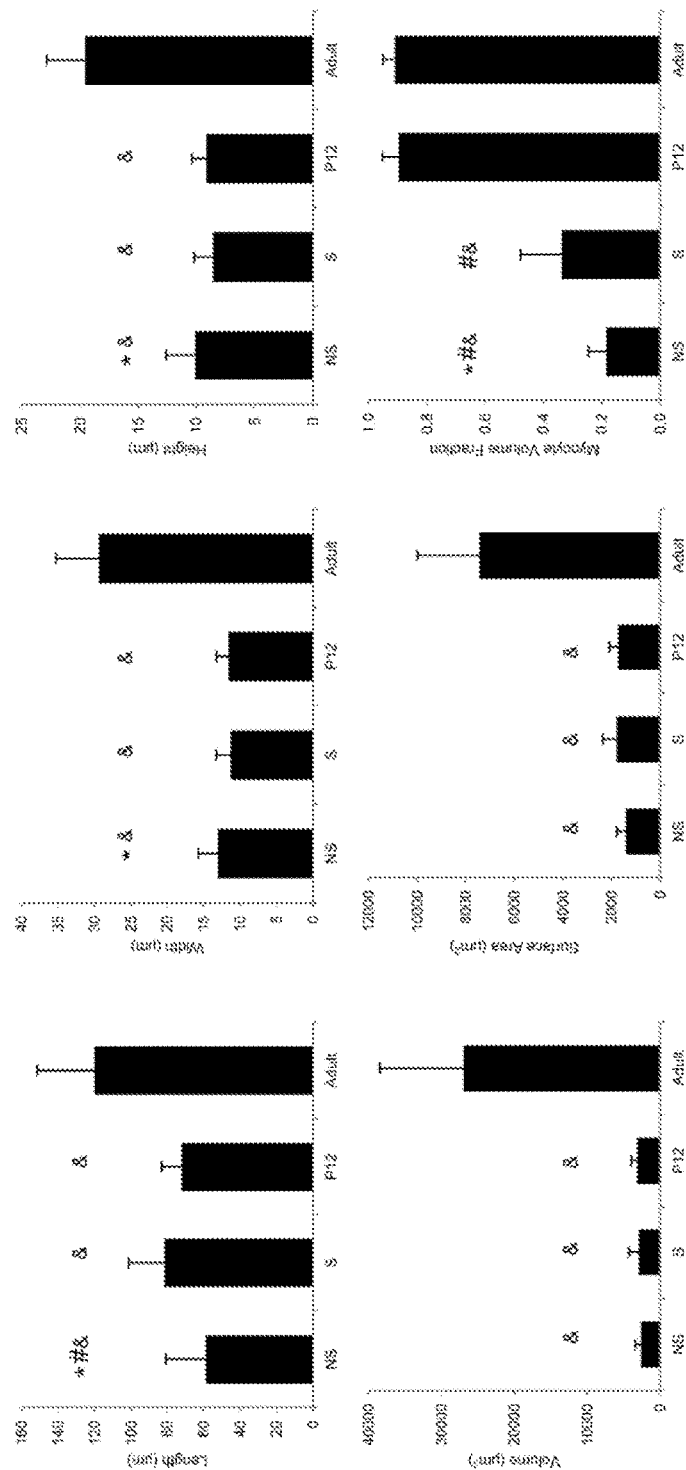

Myocyte geometry was quantified through segmentation of individual cells from the 3D image stacks. The segmentation process is shown in FIG. 32 with example myocytes from the four experimental groups. Manual manipulation of 3D triangle meshes and thresholding of the WGA channel were used to create 3D reconstructions of myocytes. Central cross-sections of the reconstructed myocytes (FIGS. 32A, D, G and J) served for masking the WGA and Cx43 image data (FIGS. 32B, E, H and K). 3D visualizations of the segmented myocytes and associated Cx43 labeling are shown in FIGS. 32C, F, I and L. Myocyte geometry was calculated from the segmented cells (FIG. 33). Adult myocytes were significantly larger in length, width, height, surface area and volume compared to non-stimulated and stimulated engineered tissue and P12 native rat myocardium. Length, width, height, surface area and volume were not statistically different between myocytes from electrically stimulated tissue samples and P12 native myocardium. However, non-stimulated myocytes had more often a rounded morphology as indicated by a smaller mean length compared to stimulated and P12 myocytes and higher widths and heights compared to stimulated myocytes.

Figure 34:
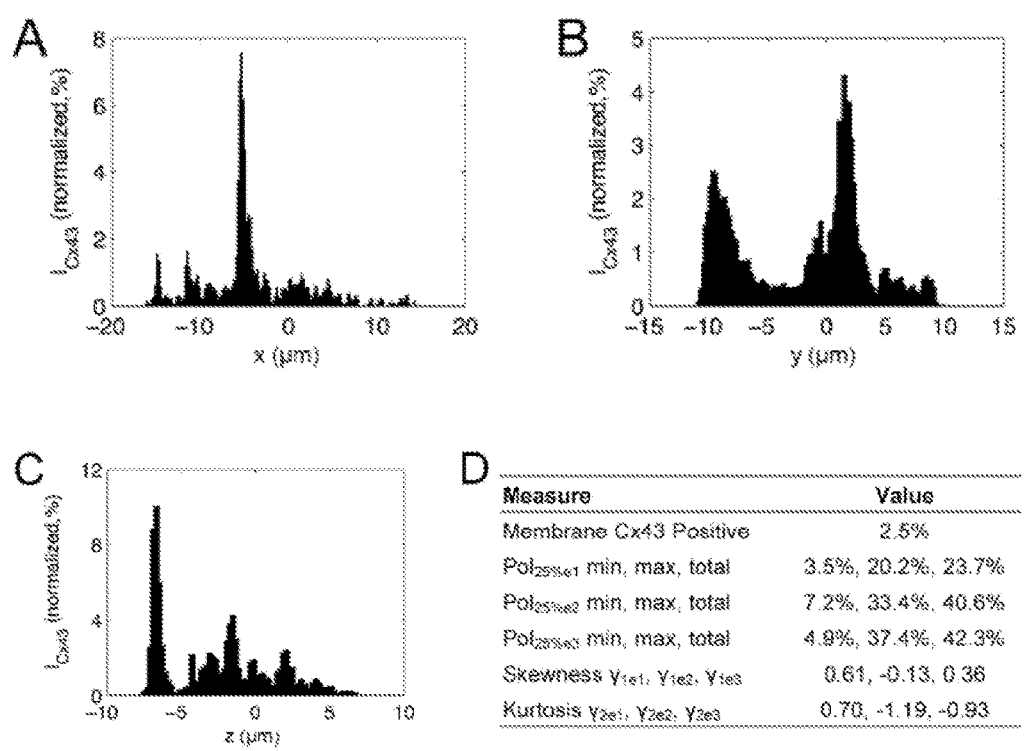

The spatial distribution of Cx43 was characterized through projections of Cx43 intensities on myocyte eigenvectors $e_1$, $e_2$ and $e_3$ and measures of polarization and higher-order statistical moments. FIG. 34 shows the profile projections for the segmented example cells in FIG. 32. In the non-stimulated myocyte there was little Cx43 plaque formation indicated by the low percent membrane positive for Cx43 (FIG. 34D), and a large plaque dominated the profiles as indicated by a sharp peak in the Cx43 projection profiles (FIGS. 34A-C). The stimulated myocyte had the majority of Cx43 plaque formation on one end of the cell as can be seen in the profile on eigenvector $e_1$ (FIG. 34D) and the large difference between $Pol_{25\%\ e1min}$ and $Pol_{25\%\ e1max}$ and strong negative skewness ($\gamma_{1e1}$) (FIG. 34H). The P12 myocyte had an approximately uniform distribution of Cx43 around the lateral membrane as can be seen in the profile for eigenvector $e_1$ (FIG. 34I). The distribution had a skewness ($\gamma_{1e1}$) near zero and a kurtosis near −1.2 which indicates a uniform distribution (FIG. 34L). Furthermore, the profile for eigenvector $e_3$ (FIG. 34K) for the P12 myocyte showed a bimodal distribution, which indicates that Cx43 plaques were concentrated on the lateral sarcolemma as opposed to cell ends as seen in the adult myocyte. The adult myocyte had the majority of Cx43 associated intensities at cell ends which can be seen from projections for eigenvector $e_1$ (FIG. 34M) and a $Pol_{25\%\ e1total}$ greater than 50%. The Cx43 distribution was weakly asymmetric as indicated by a small difference in $Pol_{25\%\ e1min}$ and $Pol_{25\%\ e1max}$ and a small positive skewness ($\gamma_{1e1}$).

Figure 35:
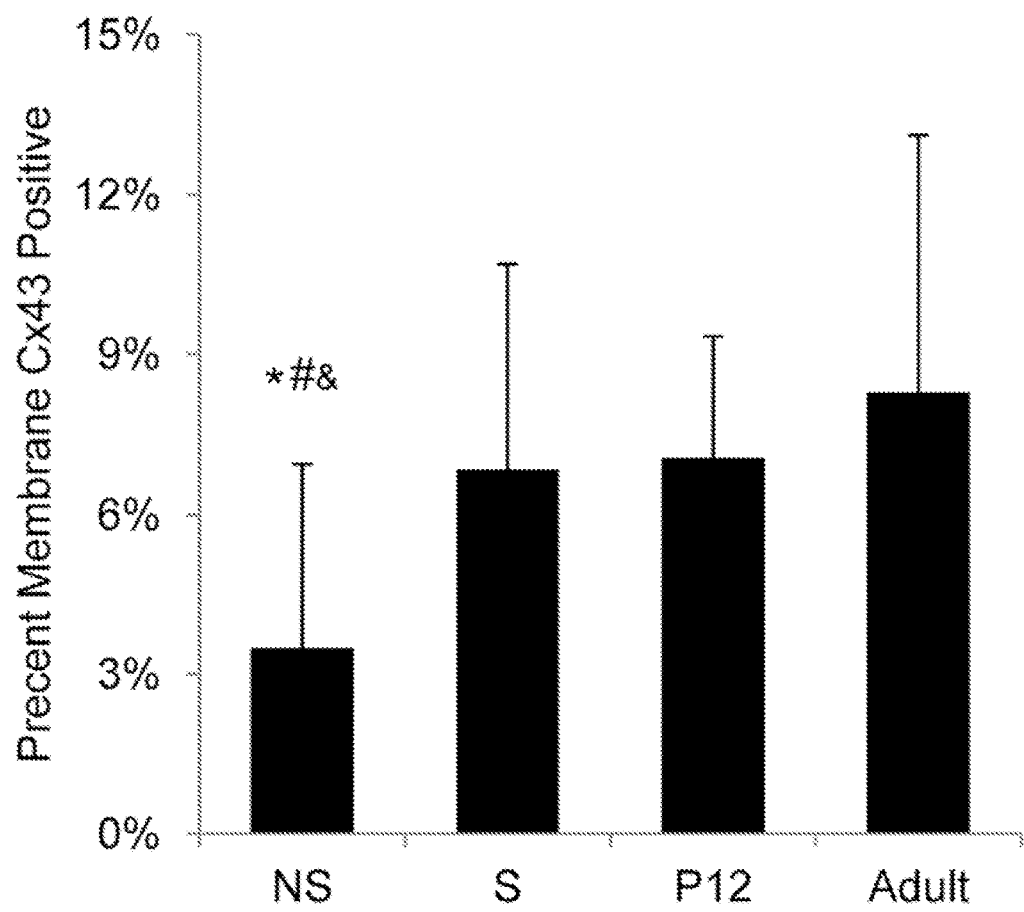

The extent of Cx43 plaque formation was assessed through calculating the percentage of membrane positive for Cx43 staining on segmented myocytes. Non-stimulated engineered tissue had a significantly lower percentage of the membrane area stained positive for Cx43 (3.5±3.4%) compared to stimulated engineered tissue (6.9±3.8%) and that of P12 (7.1±2.3%) and adult (8.3±4.8%) rat myocardium (FIG. 35) (p<0.01).

Figure 36:
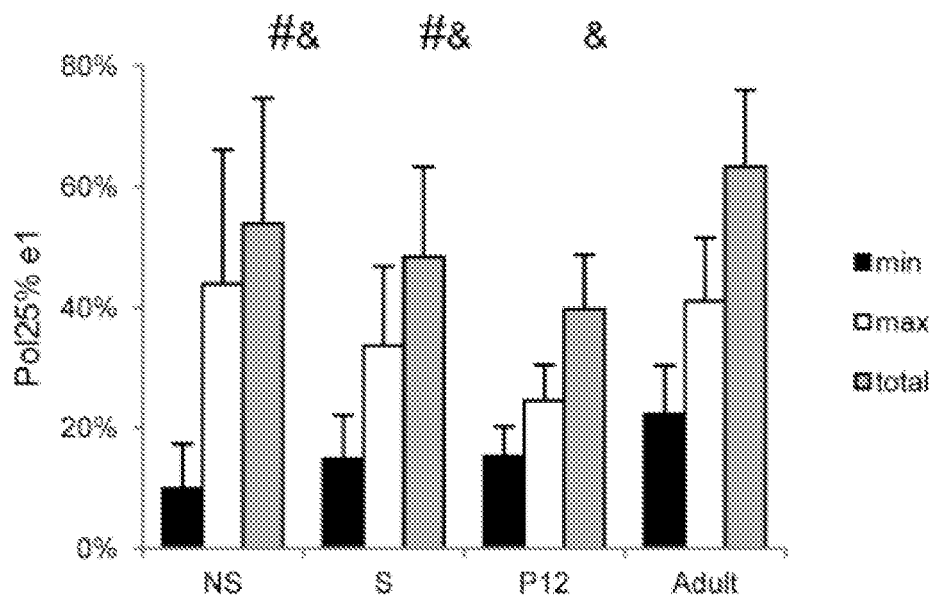
Figure 36:
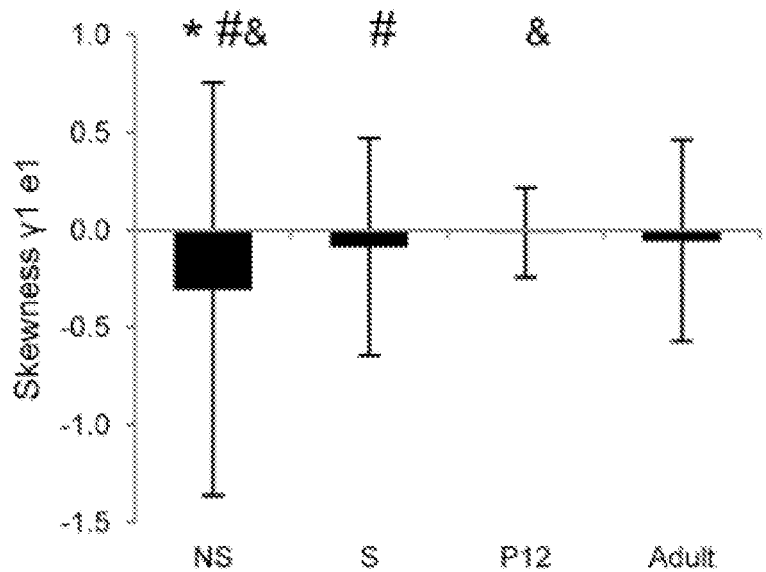

Statistical results of Cx43 profiles for all segmented cells are presented in FIG. 36. Myocytes from non-stimulated and stimulated engineered tissue and P12 native myocardium exhibited no polarization of Cx43, whereas adult myocytes had the majority of their Cx43 concentrated at cell ends (FIG. 36A). Non-stimulated myocytes had a large difference in $Pol_{25\%\ e1min}$ and $Pol_{25\%\ e1max}$ (FIG. 36A) and a high standard deviation of skewness (FIG. 36B) indicating that most cells had Cx43 plaques concentrated on one side of the myocyte. Furthermore, the measured skewness (FIG. 33B, E, H) and kurtosis (FIG. 33C, F, I) was highly variable for the non-stimulated group compared to all other groups for all three eigenvector profiles.

Example Five

The transverse tubular system (t-system) in mammalian ventricular cardiomycocytes has several functions. First, it enlarges the surface to volume ratio of the ventricular cell increasing the exposure of the cell interior to the interstitial fluid. This facilitates the cellular exchange of ions and metabolites. Second, it carries electrical excitation rapidly into the interior of the cell to enable near synchronous activation across the cell diameter. The t-system extends in close proximity to the sarcoplasmic reticulum, which allows their membrane proteins to form multimolecular complexes including L-type $Ca^{2+}$ channels in the sarcolemma and ryanodine receptors (RyRs) in the membrane of the sarcoplasmic reticulum apposed to the t-tubules. Initial remodelling of t-tubules and RyR clusters was investigated as a result of dyssynchronous heart failure (DHF) and cardiac resynchronization therapy (CRT). In addition to the description which follows, a complete description of the experimental methods and results are disclosed in Sachse et al., "Subcellular Structures and Function of Myocytes Impaired During Heart Failure are Restored by Cardiac Resynchronization Therapy," *Circulation Research*, scheduled for publication in 2012, which is hereby incorporated by reference herein in its entirety.

Isolated cardiac myocytes were labeled using wheat germ agglutinin (WGA) conjugated to Alexa Fluo-555 and monoclonal anti-RyR2 antibody with a secondary goat anti mouse IgG (H+L) antibody attached to Alexa Fluor 488. 3D image stacks of labeled cells immersed in glycerol were acquired using a confocal microscope (LSM 5 Live Duo, Carl Zeiss, Jena, Germany) equipped with a 63× oil immersion lens (Numerical aperture 1.4).

The cells were fixed for 10 min at room temperature with 1% paraformaldehyde and washed afterwards with phosphate buffered saline (PBS) solution. Cells were attached to a chamber using polylysine and permeabilized with PBS solution containing 0.3% Triton X-100 for 15 min. After washing with PBS, cells were bathed in Image-iT FX Signal Enhancer (Molecular Probes, Eugene, Oreg.) for 30 min. Subsequently, cells were washed and blocked for 60 min using a PBS solution containing 10% normal goat serum (NGS, Millipore, Billerica, Mass.) and 0.05% Triton X-100. Afterwards the cells were incubated overnight at 4° C. with the monoclonal anti-RyR2 antibody (C3-33) (Pierce Biotechnology, Rockford, Ill.) prepared in PBS-incubation solution containing 2% bovine serum albumin (BSA), 2% NGS and 0.05% Triton X-100. The cells were washed with PBS and incubated for 60 min with a secondary goat anti mouse IgG (H+L) antibody attached to Alexa Fluor 488 (Molecular Probes, Eugene, Oreg.). The next day the cells were washed and stored in PBS solution. ProLong Gold Antifade Reagent (Molecular Probes, Eugene, Oreg.) was added to the cells 24 h prior to imaging.

The confocal aperture was set to an Airy number of 1. Alexa Fluor 488 was excited with a 488 nm laser line and the emitted light was band-pass filtered at 505 to 530 nm. Alexa Fluor 555 was excited with a 543 nm laser and the emitted light long-pass filtered at 560 nm. A two-track protocol was used to provide for spatial registration of the WGA and RyR image stacks. With this protocol the imaging of WGA and RyR associated fluorescence was performed quasisimultaneously by alternating WGA and RyR imaging for each image of the 3D stack. The separation of excitation and emission spectra of the applied fluorophores assured that cross-talk between WGA and RyR signals was negligible. Image stacks covered transversal segments of myocytes with a typical dimension of 512 (width)×128 (length)×200 (height) voxels at a resolution of 100 nm in the x, y and z direction. Imaging of a cell segment required ~30 min. After acquisition of an image stack, a single image at half height was taken and visually compared to images in the stack. Image stacks were rejected if the visual inspection revealed that the image was shifted more than 5% of the height of the image stack. Visual inspection was also carried out to reject image stacks with insufficient WGA or RyR intensity and imaging artefacts, such as vibration and drift.

The processing of the confocal microscopic images included image analysis and deconvolution. The software was implemented in C++, Perl and Matlab 7.9 (The Mathworks, Inc., Natick, Mass.). In short, methods of noise reduction, removal of background signals, correction of depth-dependent attenuation, and deconvolution were applied. Deconvolution of the image stacks was based on the Richardson-Lucy algorithm5,6 with measured point spread functions (PSFs). The PSFs were obtained from images of fluorescent beads (diameter: 100 nm; excitation wave length: 505 nm; emission wavelength: 515 nm) (Molecular Probes, Eugene, Oreg.) suspended in 0.2% agarose. The PSFs (number of PSFs: 6) were aligned and averaged. The averaged PSF exhibited a full width at half maximum (FWHM) of ~260 nm in xy and ~750 nm in z direction. Measured PSFs in regions above 20 µm of the glass slide exhibited a small signal-to-noise ratio and were not used in this process. Based on this finding, further processing of the image data was restricted to regions within 12 µm of the glass slide.

The sarcolemma including the t-system was detected by thresholding of the WGA image stacks followed by median filtering. The threshold was calculated from image statistics and set to mode+stddev. Image stacks were segmented in outer sarcolemmal, t-system, intra- and extracellular regions by morphological operators. Euclidean distance maps were calculated from the sarcolemmal regions. RyR clusters were extracted by maxima search and region-growing methods from the image stacks of anti-RyR2 antibody labeled myocytes. The threshold was set to mode+4 stddev. Centers of RyR clusters were identified by the centers of mass of segmented regions. Density (number of clusters per unit volume) and distances between RyR cluster centers were calculated to quantify the spatial distribution of RyR clusters. Distances of RyR clusters to the sarcolemma (including t-system) were determined from probing the distance maps at cluster centers.

Figure 43:
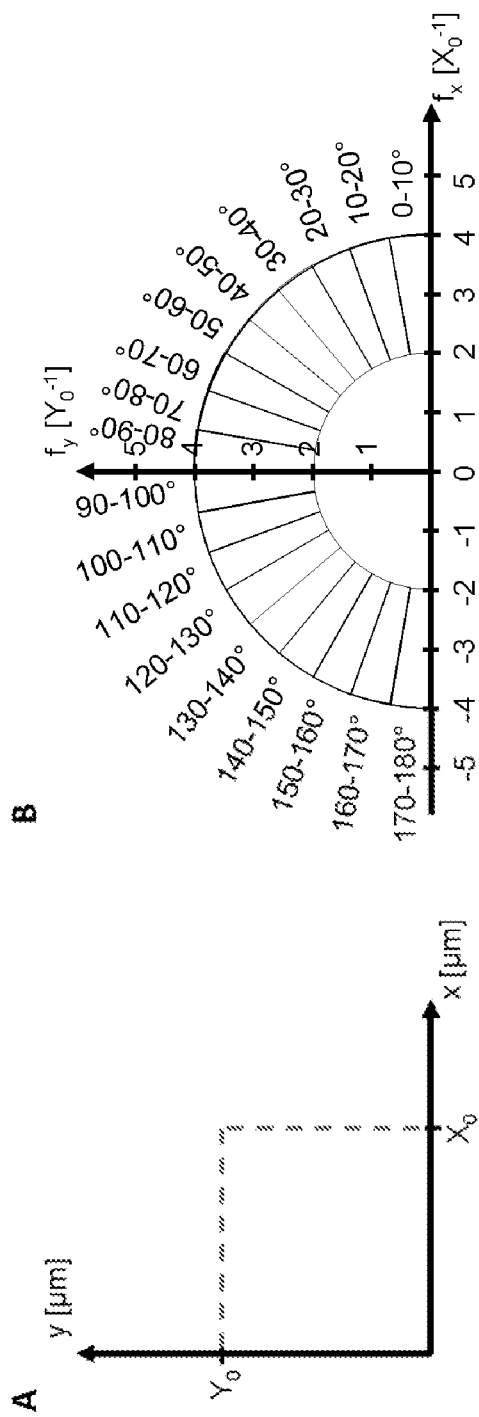
FIGS. 43-51 display an exemplary multidimensional Fourier analysis of image data as described herein. The displayed analysis was applied to tubular structures and protein distributions and consists of selection of specific lengths and orientation of waves extracted by a multidimensional Fourier transform.

Spatial distributions of the t-system and RyR protein distribution in 3D image stacks were characterized from their Fourier spectra. A discrete three-dimensional Fourier transform was applied on the image data after multiplying them with a Gaussian window function. The width of the Gaussian window was set to attenuate signals for regions with outer sarcolemma Intensities in spherical sectors with a central angle of 10° at spatial frequencies from 0.4 to 2 $\mu m^{-1}$ and 0.4 and 1 $\mu m^{-1}$ were integrated from the t-system and RyR spectra, respectively. Sectioning of a two-dimensional Fourier domain is illustrated in FIG. 43. As a measure of directionality of structures served the ratio of summed intensities within 12.5° to the (0,1,0) axis in the frequency domain to the overall sum of intensities in the spherical sectors.

Spatial Organization of T-Tubules and RyRs in Canine Ventricular Myocytes

Figure 44:
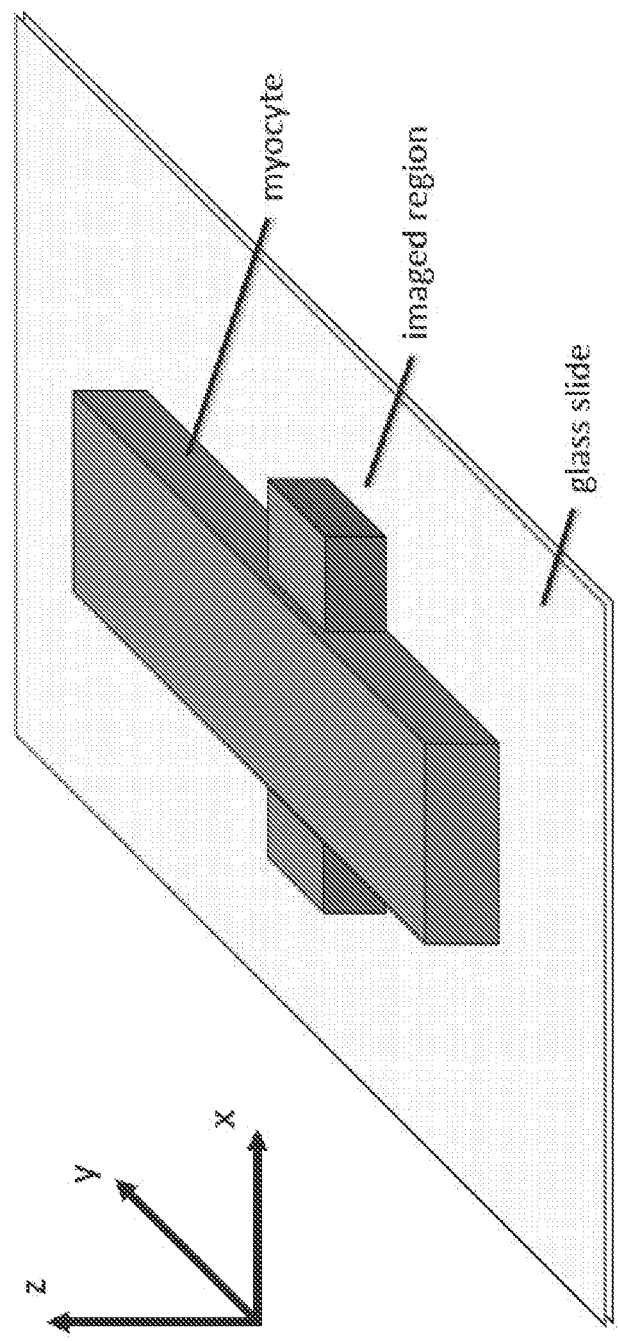
Figure 45:
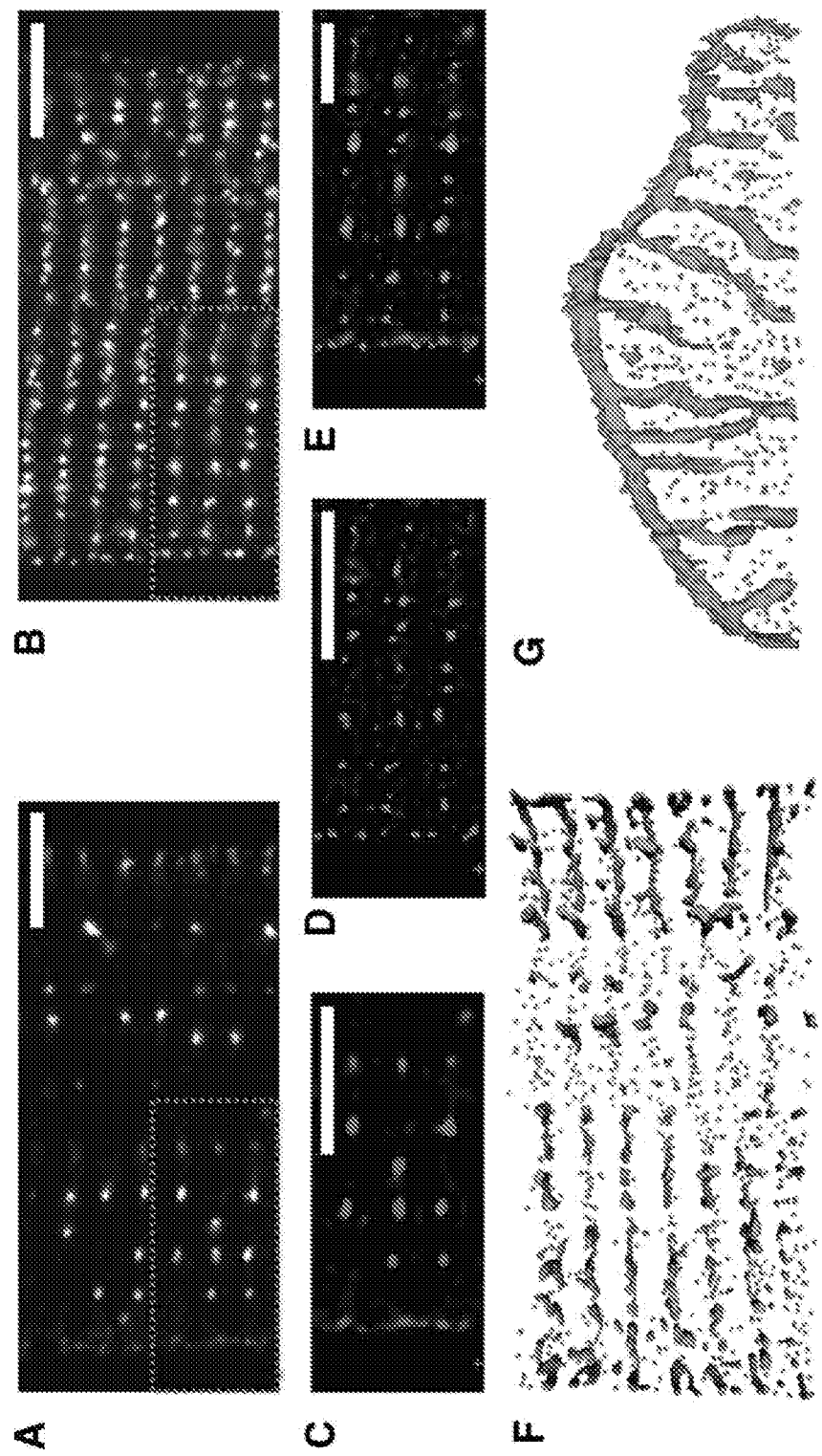
Figure 46:
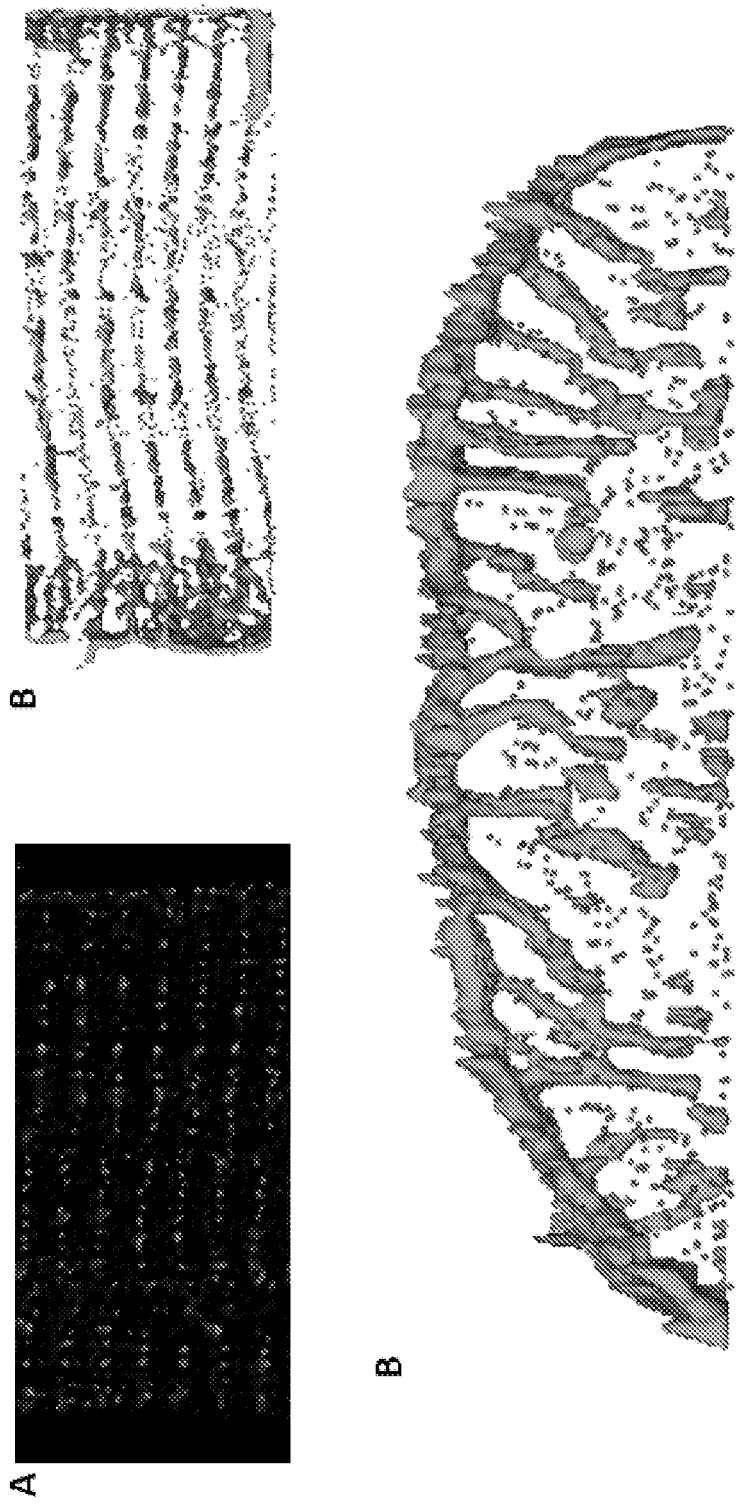
Figure 47:
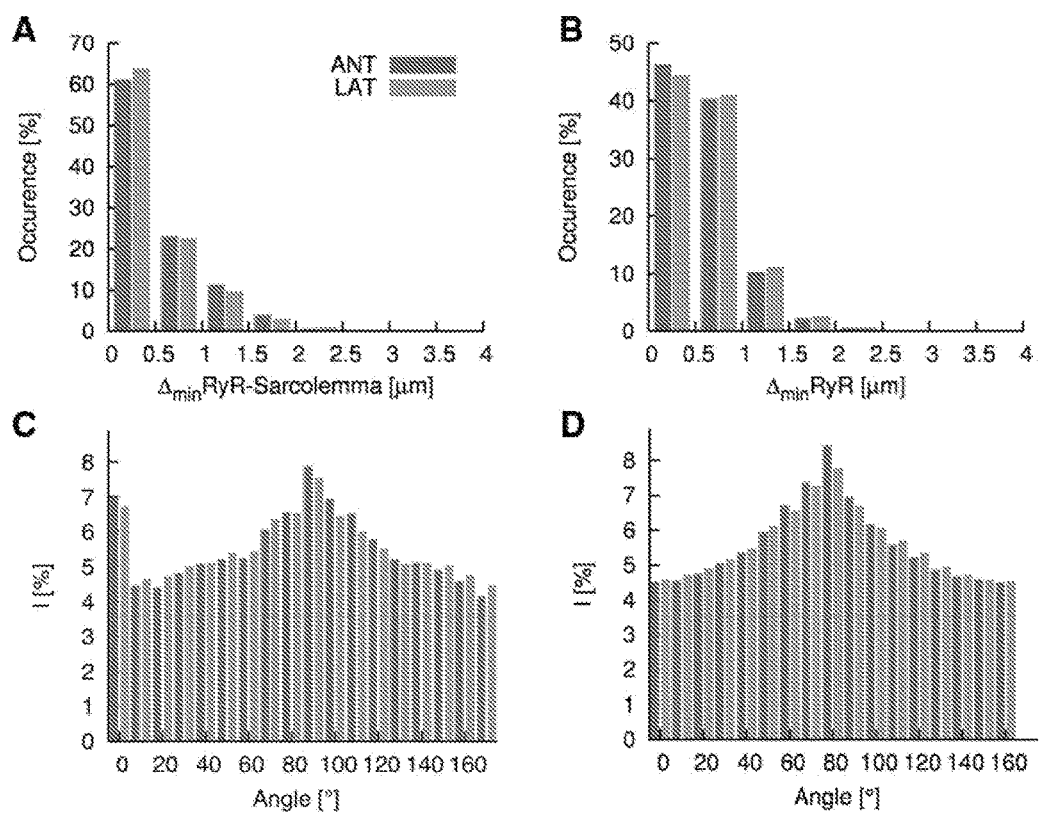

Control canine cells were isolated from both the anterior and lateral walls of the left ventricle. The sarcolemma, including t-tubules, and RyRs were labeled with WGA conjugate and monoclonal antibodies, respectively. Image stacks of myocyte segments (FIG. 44) were obtained. FIG. 45 displays the arrangement of t-tubules and RyR clusters in a segment of a myocyte isolated from the lateral wall of the left ventricle. T-tubules are arrayed regularly and appear in the vicinity of the z-disks as transverse rows (FIGS. 45A and 45C) in the y-axis. RyRs are clearly registered in the y-axis (FIGS. 45B and 45D), similarly to the t-tubules. This becomes clear in the overlay of WGA and RyR images (FIG. 45E), where many RyR clusters appear colocalized with t-tubules and presumably form couplons. The image indicates that a significant number of RyR clusters are not associated with t-tubules. This is clearer in FIGS. 45F and 45G, which display 3D reconstructions of RyRs and t-tubules in the myocyte segment. The t-tubules and RyRs tend to form sheets in the vicinity of the z disks. Reconstructions of t-tubules and RyR clusters in control anterior cells displayed similar features (FIG. 46). A detailed analysis of the 3D reconstructions from anterior and lateral ventricular cells (FIG. 47) revealed distances between centers of RyR clusters and the sarcolemma that are similar in both cell types ($0.44 \pm 0.51$ μm and $0.41 \pm 0.49$ μm, respectively). Also, a nearest-neighbor analysis of RyRs did not show significant differences in anterior and lateral cells ($0.62 \pm 0.37$ μm versus $0.63 \pm 0.38$ μm). We used Fourier analysis to characterize the spatial distribution of t-tubules and RyRs in 3D. The analysis was constrained to spatial frequencies corresponding to spatial periodicities of z-disks ($2.0 \pm 0.5$ μm). Intensity histograms were calculated in sectors with an opening angle of 10° (FIG. 43). Maxima in the Fourier histogram from RyRs and WGA images appeared at the sectors to 90° (FIGS. 47C and 47D), which indicated regular arrangement of the labeled structures along the y-axis. A local maximum in the WGA Fourier histogram at 0-10° indicated regular arrangement of the t-tubules along the x-axis. The Fourier histograms were almost identical in both anterior and lateral cells.

Characterization of T-Tubules and RyRs in A6 Myocytes

Figure 48:
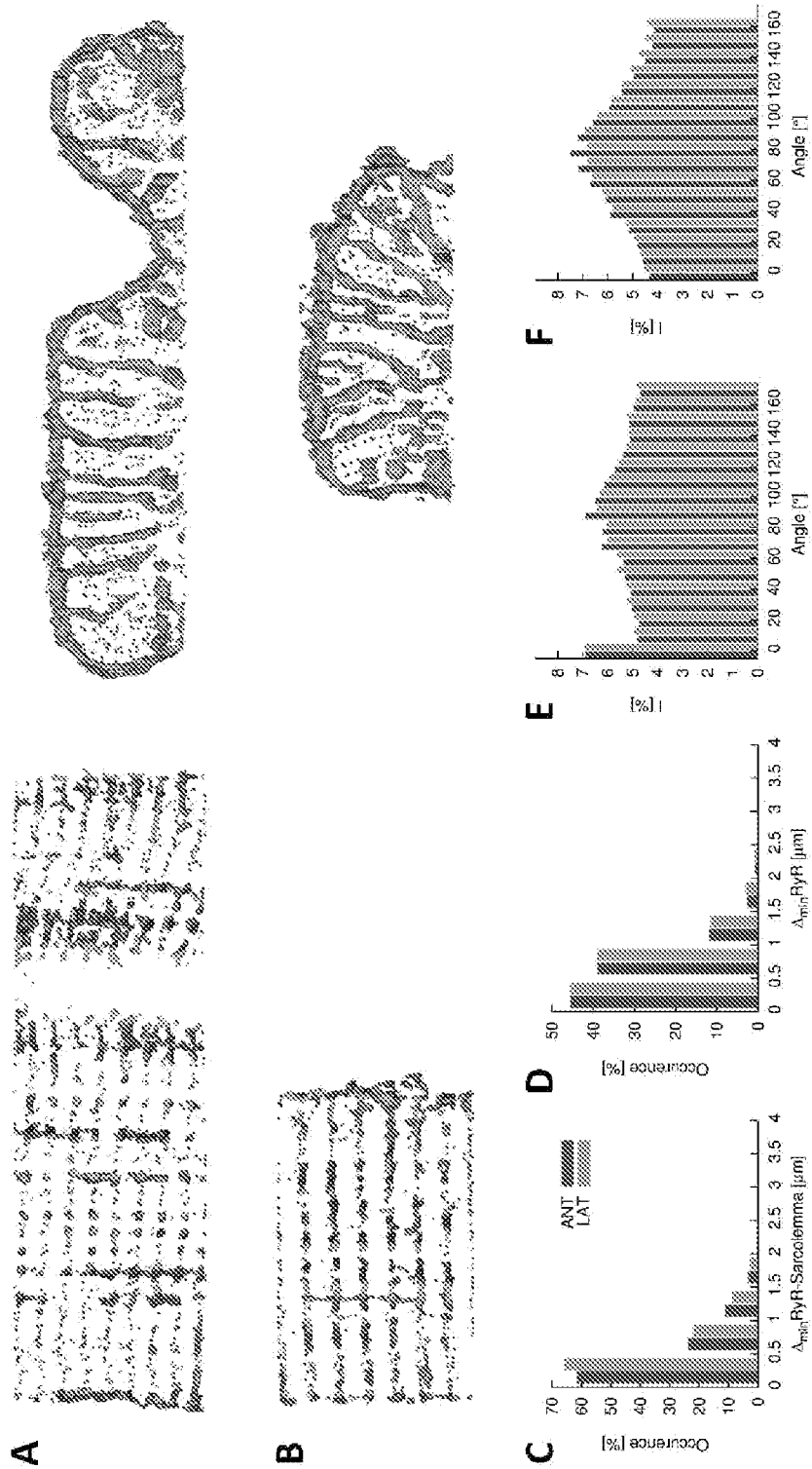

A6 cells were analyzed using the same methods as applied to control cells. Reconstructions of t-tubules and RyR clusters in A6 cells displayed features similar to control cells (FIG. 48). Differences of the RyR cluster-sarcolemma distance between anterior and lateral cells were not significant ($0.45 \pm 0.49$ μm and $0.41 \pm 0.47$ μm, respectively). Similarly, differences of the nearest neighbor distance of RyR clusters in both cell types were not significant ($0.64 \pm 0.40$ μm and $0.64 \pm 0.40$ μm, respectively). Control and A6 lateral cells exhibited insignificant differences for the RyR cluster density ($0.44 \pm 0.08/\mu m^3$ versus $0.50 \pm 0.06/\mu m^3$).

Remodeling of T-Tubules and RyR Distributions in Myocytes after DHF

Figure 49:
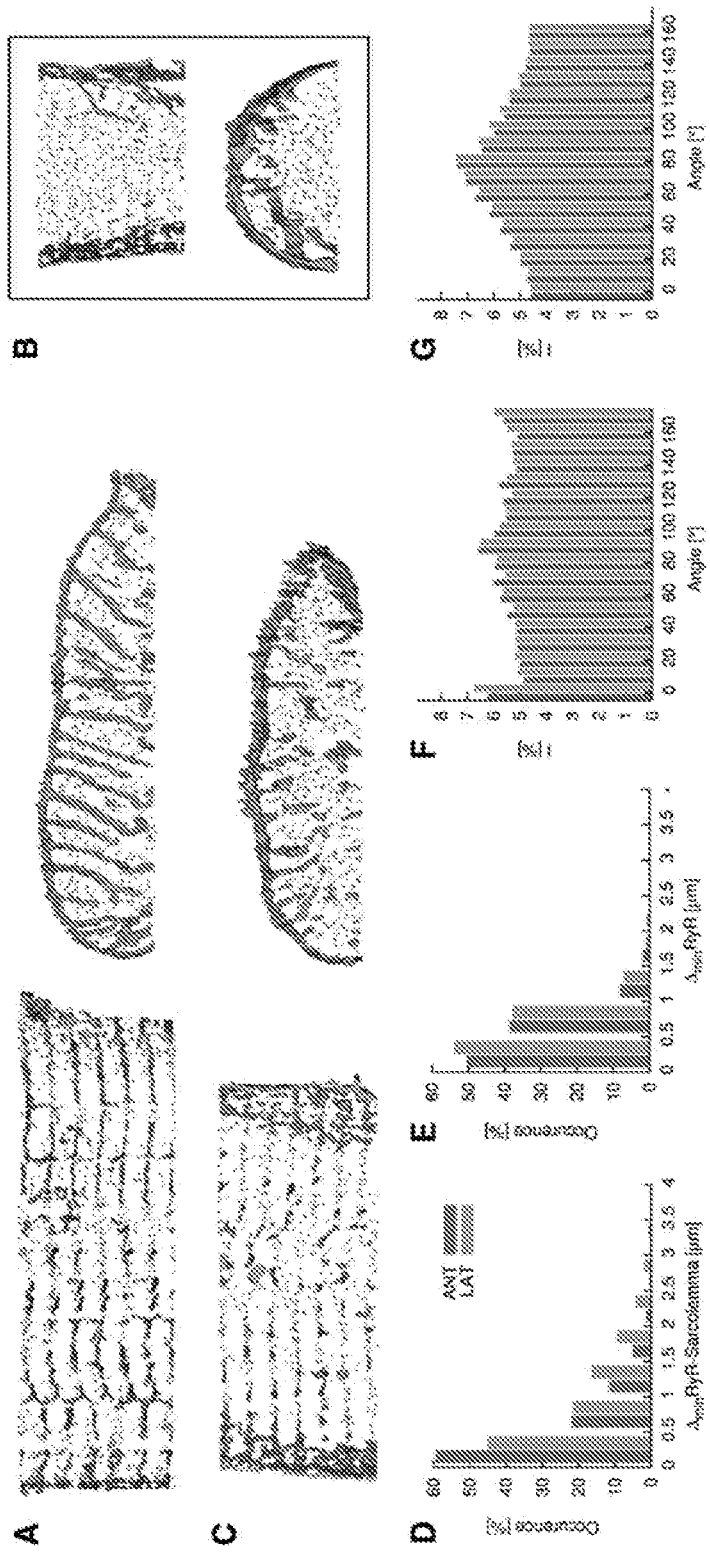

The described methods were used to study the alterations in distribution of t-tubules and RyRs in isolated left ventricular cells taken from dog hearts 6 weeks after left bundle-branch ablation and rapid atrial pacing. Using this protocol, the hearts had exhibited severe systolic dysfunction and the animals were in HF. Cells from both the lateral and anterior ventricular walls were examined Anterior cells from DHF ventricles did not show striking alterations when they were visually compared with control cells. This was apparent in the deconvolved images and reconstructions displayed in FIG. 49A. However, in lateral ventricular cells, it was immediately apparent that the t-tubular system was dramatically remodeled. An example is presented in FIG. 49B, in which the t-system was sparse centrally and the T-tubules in the cell periphery exhibited longitudinal components. Furthermore, the cell showed a loss of alignment of RyRs. A less extreme case of t-tubule remodeling is shown in FIG. 49C. These consequences of DHF are apparent in the 2D optical slices, the 3D reconstructions viewed from above the myocyte, and along the major axis of the myocyte. An effect of t-system remodeling in DHF is that the majority of RyRs are not associated with sarcolemmal structures. In comparison to control and A6, distances between RyR clusters and the nearest sarcolemma increased significantly in DHF lateral cells ($0.66 \pm 0.72$ μm) but not in anterior cells ($0.48 \pm 0.58$ μm) (FIG. 49D). The nearest-neighbor distance of RyR clusters showed little change between anterior and lateral cells ($0.63 \pm 0.38$ μm and $0.59 \pm 0.35$ μm, respectively) and when compared with control and A6 cells (FIG. 49E versus FIG. 47B and FIG. 48D). A Fourier analysis was again used to characterize the spatial distribution of t-tubules and RyRs from anterior and lateral DHF cells (FIGS. 49F and 49G). Maxima in the Fourier histogram from WGA images appeared for sectors at 0-10° and 90-100° for both cell types (FIG. 49F). In comparison to normal cells (FIG. 47C), maxima indicating regular arrangement of the t-tubules along they-axis were reduced. The Fourier histograms from RyR images indicated that the arrangement of RyR clusters was similar in normal and DHF cells of both types (FIG. 49G versus FIG. 47D). Changes in the distribution of RyRs and t-tubules was described in DHF cells both before and after the cells were subjected to CRT.

Partial Restoration of T-Tubules and RyR Distributions after CRT

Figure 50:
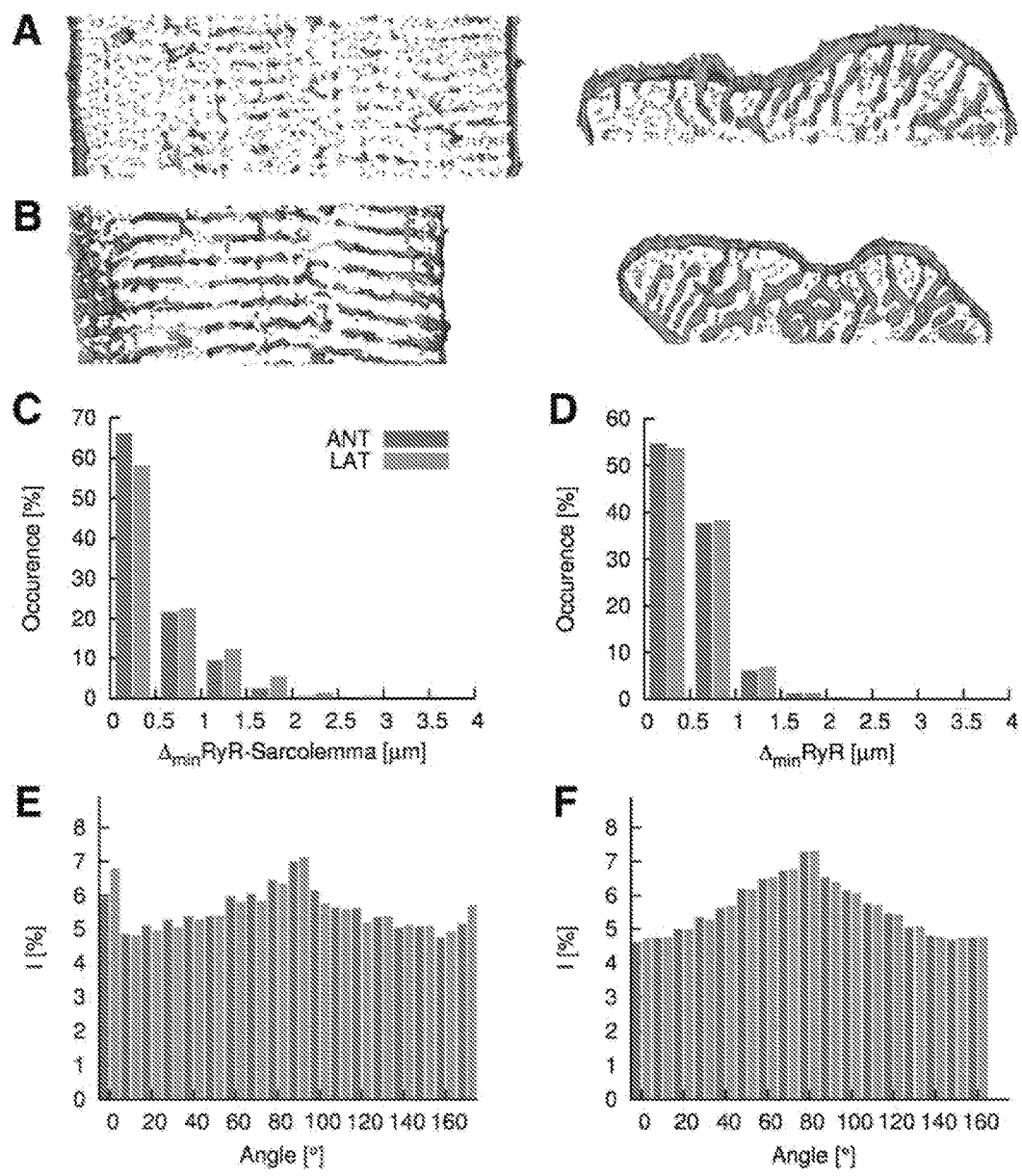

The spatial distributions of t-tubules and RyRs in myocytes were investigated after they had been paced to induce DHF for 3 weeks and were then subject to rapid pacing CRT for 3 weeks. The effects on these structures were not distributed uniformly throughout the heart. There was little effect of CRT on these cell types (see FIG. 50A). However, there was a remarkable reverse structural remodelling of t-tubules after CRT in lateral cells. This is obvious from visual inspection of FIG. 50B and is particularly apparent in the 3D reconstruction of the cell segment viewed from the z-direction (middle panel) and y-direction (right panel). RyR-nearest sarcolemma distances were $0.40 \pm 0.50$ μm and $0.48 \pm 0.57$ μm for anterior and lateral cells, respectively. Measurements of RyR-nearest sarcolemma distances (FIG. 50C versus FIG. 49D) indicated that the t-system was not completely restored, but the remodeling included t-tubules assuming a more normal distribution, that is, resembling controls. Some longitudinal components of the t-system remained but were reduced. CRT did not affect the nearest-neighbor distance of RyR clusters in anterior and lateral cells ($0.59 \pm 0.35$ μm and $0.61 \pm 0.36$ μm, respectively) (FIG. 50D), which was also not altered in DHF in both cell types. Maxima in the Fourier histogram from WGA images appeared at similar sectors for images from CRT and DHF cells (FIG. 50E). Also, the Fourier histograms from RyR images indicated that the arrangement of RyR clusters was similar in CRT and DHF cells of both types (FIG. 50F versus FIG. 49G).

Quantitative Analysis of the Effects of DHF and CRT on Subcellular Structure

Figure 51:
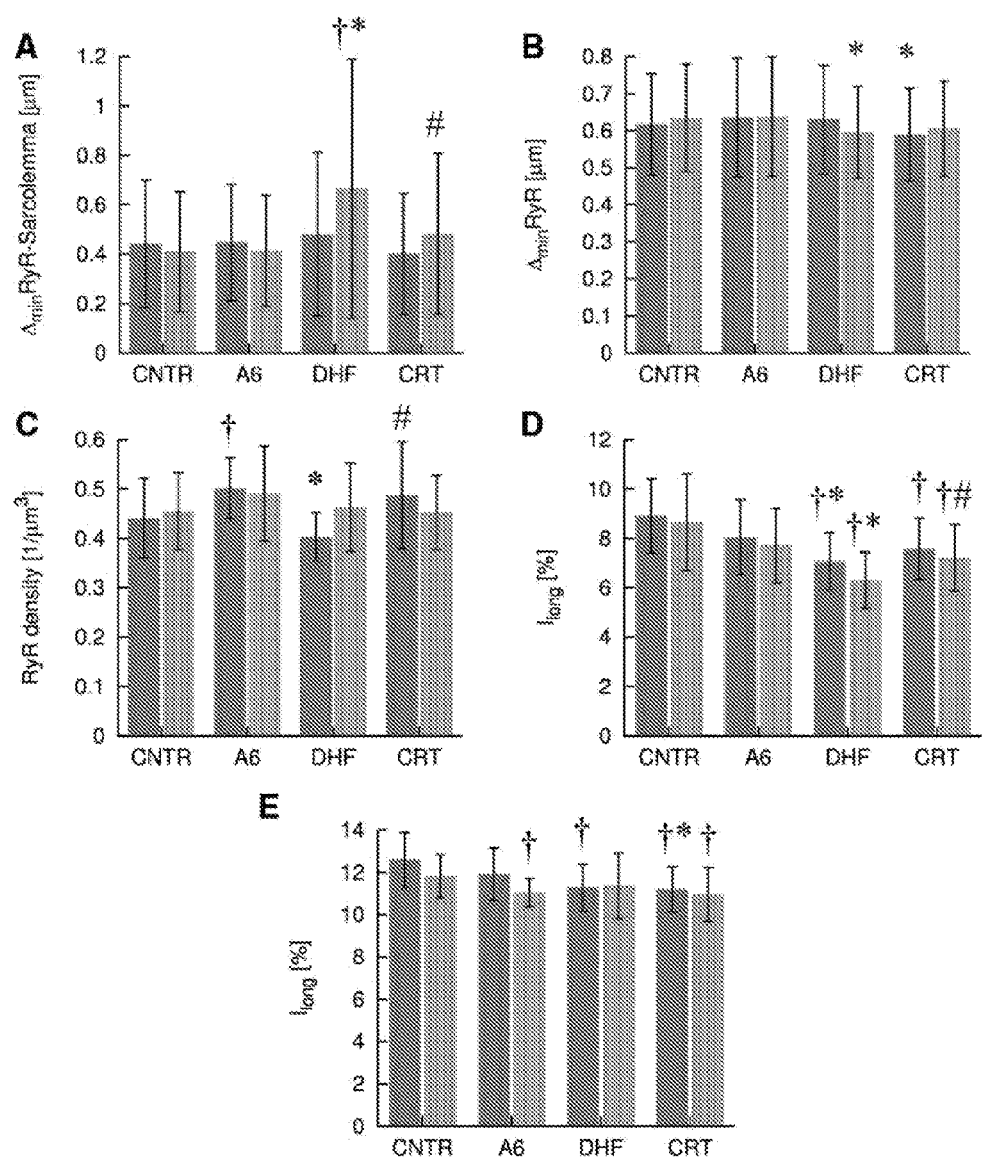

A summary and statistical analysis of the results is presented in FIG. 51. A marker of t-system remodeling was the RyR-sarcolemma distance (FIG. 51A). In lateral myocytes, a significant increase was associated with DHF, which was substantially restored by CRT. Compared with control, neither DHF nor CRT caused alterations of the nearest-neighbor distance (FIG. 51B). Differences of the density of RyR clusters were not significant for control versus DHF as well as A6 versus CRT (FIG. 51C). The spatial arrangement of the t-system and RyR was characterized by the ratio of intensities associated with the longitudinal axis of cells to the overall intensities in the WGA and RyR image stacks, respectively. In comparison to control and A6, DHF was associated with a reduced longitudinal intensity ratio of WGA signals in both lateral and anterior cells (FIG. 51D).

This reduction indicated a less regular longitudinal spacing of the t-system in DHF. After CRT, the longitudinal intensity ratio was partially restored in lateral and anterior cells. However, in comparison to control, the longitudinal intensity ratio remained at reduced levels after CRT. DHF was associated with a slightly reduced longitudinal intensity ratio of RyR signals in anterior cells but not in lateral cells (FIG. 51E). CRT cells exhibited a significant albeit small reduction of longitudinal intensity ratios of RyR signals in both cell types versus control. The differences between DHF and CRT cells were not significant, indicating that CRT was not able to restore the spatial arrangement of RyR clusters.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

Various publications are referenced in this document. These publications in their entireties are hereby incorporated by reference into this application in order to more fully describe the state of the art to which the disclosed system and method pertains. The references disclosed are also individually and specifically incorporated by reference herein for the material contained in them that is discussed in the sentence in which the reference is relied upon.

What is claimed is:

1. A device comprising:
a probe defining a central bore, the probe having an outer surface, a distal end, an opposed proximal end, and a longitudinal axis extending between the distal end and the proximal end of the probe, the distal end defining a distal tip configured to contact a selected tissue of a subject, the outer surface of the probe extending away from the distal tip in a proximal direction and defining an outer diameter of the probe along a longitudinal length of the probe, the probe comprising:
image transmission means positioned therein the central bore of the probe and configured for communication with a light source; and
an objective lens positioned therein the central bore of the probe proximate the distal tip of the probe; and
an annular dye carrier comprising an open-cell polymer foam filled at least partially with a hydrogel, the dye carrier being loaded with at least one fluorescent dye, the dye carrier having a bottom surface, the dye carrier being detachably coupled thereto at least a portion of the outer surface of the distal end of the probe such that the entire bottom surface of the dye carrier is radially spaced from the longitudinal axis and the objective lens of the probe to permit direct transmission of light between the objective lens of the probe and the selected tissue, wherein the bottom surface of the dye carrier is configured to selectively contact the selected tissue of the subject to diffuse the at least one fluorescent dye through the bottom surface of the dye carrier and into the selected tissue of the subject,
wherein, following diffusion of the at least one fluorescent dye into the selected tissue, the image transmission means and the objective lens are configured to transmit light to the selected tissue and to receive emitted light from the selected tissue.

2. The fluorescence imaging device of claim 1, wherein the at least one fluorescent dye is suspended in a buffer solution.

3. The fluorescence imaging device of claim 2, wherein the at least one fluorescent dye and the buffer solution together comprise at least 95% by weight of the dye carrier.

4. The fluorescence imaging device of claim 1, wherein the dye carrier comprises at least one antibody agent.

5. The fluorescence imaging device of claim 1, wherein the at least one fluorescent dye is selected from a group consisting of: Alexa, Texas Red, FITC, Oregon Green, Rhodamine Green, Lucifer yellow, Fluo 3, Fluo 4, Fluorescite and di-8-Anepps.

6. The fluorescence imaging device of claim 1, further comprising means for steering the probe such that the bottom surface of the dye carrier contacts a desired region of the tissue of the subject.

7. The fluorescence imaging device of claim 1, wherein the probe has a longitudinal length, and wherein the central bore of the probe has a constant diameter along the longitudinal length of the probe.

8. The fluorescence imaging device of claim 1, wherein the probe has a longitudinal length, and wherein the central bore of the probe has a variable diameter along the longitudinal length of the probe.

9. The fluorescence imaging device of claim 8, wherein the diameter of the central bore is reduced proximate the distal tip of the probe.

10. The fluorescence imaging device of claim 9, wherein the outer diameter of the probe remains constant along the longitudinal length of the probe.

11. The fluorescence imaging device of claim 9, wherein the outer diameter of the probe varies along the longitudinal length of the probe.

12. The fluorescence imaging device of claim 11, wherein the outer diameter of the probe is reduced proximate the distal tip of the probe.

13. The fluorescence imaging device of claim 1, wherein the outer surface of the probe defines one or more protrusions proximate the distal end of the probe, and wherein the dye carrier comprises one or more channels configured to receive corresponding protrusions of the probe, the one or more protrusions of the probe configured to engage the dye carrier such that the dye carrier is detachably secured thereto the probe.

14. The fluorescence imaging device of claim 13, wherein the one or more protrusions comprise a rim extending circumferentially around the probe along at least a portion of the outer surface of the probe.

15. The fluorescence imaging device of claim 1, further comprising an outer casing that surrounds the dye carrier and is configured to limit the dispensing of the at least one fluorescent dye to a distal portion of the dye carrier that includes the bottom surface of the dye carrier.

16. The fluorescence imaging device of claim 1, wherein the image transmission means of the probe comprises a fiber-optic bundle, and wherein the objective lens and the fiber-optic bundle have a common longitudinal axis parallel to the longitudinal axis of the probe.

17. The fluorescence imaging device of claim 15, wherein the casing comprises an attachment means configured for engagement with the probe.

18. The fluorescence imaging device of claim 1, wherein the foam of the dye carrier comprises polyurethane foam.

19. A system for fluorescence imaging of tissue, comprising:
- a processor;
- a light source; and
- a fluorescence imaging device that is operatively coupled to the processor and comprises:
  - a probe defining a central bore, the probe having an outer surface, a distal end, an opposed proximal end, and a longitudinal axis extending between the distal end and the proximal end of the probe, the distal end defining a distal tip configured to contact a selected tissue of a subject, the outer surface of the probe extending away from the distal tip in a proximal direction and defining an outer diameter of the probe along a longitudinal length of the probe, the probe comprising:
    - an image transmission means positioned therein the central bore of the probe and placed in communication with the light source and the processor; and
    - an objective lens positioned therein the central bore of the probe proximate the distal tip of the probe; and
  - an annular dye carrier comprising an open-cell polymer foam filled at least partially with a hydrogel, the dye carrier being loaded with at least one fluorescent dye, the dye carrier having a bottom surface, the dye carrier being detachably coupled thereto at least a portion of the outer surface of the distal end of the probe such that the entire bottom surface of the dye carrier is radially spaced from the longitudinal axis and the objective lens of the probe to permit direct transmission of light between the objective lens of the probe and the selected tissue, wherein the bottom surface of the dye carrier is configured to selectively contact the selected tissue of the subject to diffuse the at least one fluorescent dye through the bottom surface of the dye carrier and into the selected tissue of the subject,
- wherein, following diffusion of the at least one fluorescent dye into the selected tissue, the image transmission means and the objective lens are configured to transmit light to the selected tissue and to receive emitted light from the selected tissue.

20. The system of claim 19, wherein the processor is configured to process received emitted light from the at least one fluorescent dye to form a fluorescence image.

21. The system of claim 20, wherein the processor is configured to characterize the micro-structure of tissue within the fluorescence image.

22. The system of claim 21, wherein the processor is further configured to identify conductive tissue within the selected tissue.

23. The system of claim 19, further comprising packaging for the dye carrier, wherein the packaging defines:
- a chamber configured to receive the dye carrier for storage; and
- a removal feature positioned vertically above the chamber, wherein after lateral insertion of the dye carrier into the chamber using the probe, the removal feature is configured to engage the dye carrier and promote detachment of the dye carrier from the probe as the probe is vertically withdrawn from the packaging.

24. A method of fluorescence imaging of selected tissue of a subject, comprising:
- using a fluorescence imaging device comprising:
  - a probe defining a central bore, the probe having an outer surface, a distal end, an opposed proximal end, and a longitudinal axis extending between the distal end and the proximal end of the probe, the distal end defining a distal tip, the outer surface of the probe extending away from the distal tip in a proximal direction and defining an outer diameter of the probe along a longitudinal length of the probe, the probe comprising:
    - a fiber optic bundle positioned therein the central bore of the probe and positioned in communication with a light source; and
    - an objective lens positioned therein the central bore of the probe proximate the distal tip of the probe; and
  - an annular dye carrier comprising an open-cell polymer foam filled at least partially with a hydrogel, the dye carrier being loaded with at least one fluorescent dye, the dye carrier having a bottom surface, the dye carrier being detachably coupled thereto at least a portion of the outer surface of the distal end of the probe such that the entire bottom surface of the dye carrier is radially spaced from the longitudinal axis of the probe and the objective lens of the probe to permit direct transmission of light between the objective lens of the probe and the selected tissue;
- selectively contacting the selected tissue of the subject with the bottom surface of the dye carrier to diffuse the at least one fluorescent dye through the bottom surface of the dye carrier and into the selected tissue of the subject;
- following diffusion of the at least one fluorescent dye into the selected tissue, using the fiber optic bundle and the objective lens to transmit light to the selected tissue and to receive emitted light from the selected tissue; and
- using a processor coupled to the fiber optic bundle, processing received emitted light from the selected tissue to form a fluorescence image.

25. The method of claim 24, further comprising using the processor to characterize the micro-structure of tissue within the fluorescence image, wherein the characterization of the micro-structure of the tissue comprises identifying conductive tissue within the tissue.

* * * * *